(12) United States Patent
Lavoie et al.

(10) Patent No.: US 8,518,928 B2
(45) Date of Patent: Aug. 27, 2013

(54) THERAPEUTIC COMPOUNDS

(75) Inventors: Edmond J. Lavoie, New Brunswick, NJ (US); Joseph E. Rice, New Brunswick, NJ (US); Leroy F. Liu, Somerset, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/308,197

(22) Filed: Nov. 30, 2011

(65) Prior Publication Data

US 2012/0071527 A1 Mar. 22, 2012

Related U.S. Application Data

(63) Continuation of application No. 12/258,208, filed on Oct. 24, 2008, now Pat. No. 8,093,235, which is a continuation of application No. PCT/US2007/009862, filed on Apr. 24, 2007.

(60) Provisional application No. 60/794,525, filed on Apr. 25, 2006.

(51) Int. Cl.
*A61K 31/35* (2006.01)
*C07D 245/00* (2006.01)

(52) U.S. Cl.
USPC .......................................... 514/183; 540/460

(58) Field of Classification Search
None
See application file for complete search history.

(56) References Cited

U.S. PATENT DOCUMENTS

| | | | |
|---|---|---|---|
| 4,559,157 | A | 12/1985 | Smith et al. |
| 4,608,392 | A | 8/1986 | Jacquet et al. |
| 4,820,508 | A | 4/1989 | Wortzman |
| 4,851,524 | A | 7/1989 | Brois et al. |
| 4,938,949 | A | 7/1990 | Borch et al. |
| 4,992,478 | A | 2/1991 | Geria |
| 8,093,235 | B2 | 1/2012 | Lavoie et al. |
| 2009/0156627 | A1 | 6/2009 | Lavoie et al. |
| 2011/0230531 | A1 | 9/2011 | Lavoie et al. |
| 2012/0046234 | A1 | 2/2012 | Lavoie et al. |

FOREIGN PATENT DOCUMENTS

| | | |
|---|---|---|
| CA | 2436942 | 6/2002 |
| EP | 1350794 | 10/2003 |
| EP | 1602659 | 12/2005 |
| JP | 11-180997 | 7/1999 |
| JP | 2006316008 | 11/2006 |
| WO | WO 97/48708 | 12/1997 |
| WO | WO 02/48153 A1 | 6/2002 |
| WO | WO 2005/000880 | 1/2005 |
| WO | WO 2007/127173 A2 | 11/2007 |
| WO | WO 2007/127173 A4 | 11/2007 |
| WO | WO 2009/018549 | 2/2009 |
| WO | WO 2009/018551 A2 | 2/2009 |
| WO | WO 2011/057126 | 5/2011 |

OTHER PUBLICATIONS

Han. TiPS, 2000, 21, 136-142.*
Barbieri, C.M., et al., "Defining the mode, energetic and specificity with which a macrocyclic hexaoxazole binds to human telomeric G-quadruplex DNA", Nucleic Acids Res., 35(10), 3272-86, (2007) (Epub Apr. 22, 2007).
Bertram et al., "Concise synthesis of stereodefined, thiazole—containing cyclic hexa- and octapeptide relatives of the Lissoclinums, via cyclooligomerisation reactions", Tetrahedron vol. 59, No. 35, pp. 6979-6990, 2003.
Binz, "Telomerase inhibition, telomere shortening, cell growth suppression and induction of apoptosis by telomestatin in childhood neuroblastoma cells", Eur. J. Cancer, 41, 2873-2881, 2005.
Chattopadhyay, "Efficient Construction of Doubly Functionalized Trisoxazole Derivative Relevant to the Synthesis of the Novel Telomerase Inhibitor Telomestatin and its Analogues", Synthesis, 1289-1294, 2006.
Chattopadhyay, "Convergent synthesis of a 24-membered macrocyclic hexaoxazole derivative related to the novel telomerase inhibitor telomestatin", Tetrahedron Letters, 47, 7897-7900, 2006.
Database Accession No. 2006:1228832, Database Caplus [Online] Chemical Abstracts Service, Columbus, Ohio, US; XP002659478, 9 pages, 2006.
Deeley, "Synthesis and establishment of stereochemistry of the unusual polyoxazole-thiazole based cyclopeptide YM-216391 isolated from Streptomyces nobilis", Chem. Communications, 797-799, 2005.
Doi, "Total Synthesis of (R)-Telomestatin", Organic Letters, 8, 4165-4167, 2006.
Endoh, "Useful Synthesis of Longer Array Oxazole Rings for Telomestatin", Heterocycles, 60, 1567-2572, 2003.
International Search Report and the Written Opinion of the International Search Authority, PCT/US07/09862, 9 pages, Oct. 3, 2008.
Jantos, "Oxazole-Based Peptide Macrocycles: A New Class of G-Quadruplex Binding Ligands", J. Am. Chem. Soc., 128, 13662-13663, 2006.

(Continued)

Primary Examiner — Noble Jarrell
(74) Attorney, Agent, or Firm — Viksnins Harris & Padys PLLP

(57) ABSTRACT

The invention provides compounds of formula I:

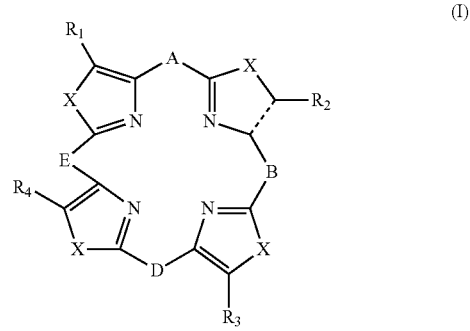

wherein A, B, D, E, $R_1$, $R_2$, $R_3$, $R_4$, $R_5$, X, and - - - have any values defined herein, as well as salts thereof. The compounds have activity as G-quadruplex DNA stabilizers and as antiproliferative agents.

16 Claims, No Drawings

(56) References Cited

OTHER PUBLICATIONS

Kim, "The Different Biological Effects of Telomestatin and TMPyP4 Can Be Attributed to Their Selectivity for Interaction with Intramolecular or Intermolecular G-Quadruplex Structures", *Cancer Res.*, 63, 3247-3256, 2003.

Kim, et al. "Telomestatin, a potent telomerase inhibitor that interacts quite specifically with the human telomeric intramolecular g-quadruplex", *J. Am. Chem. Soc.*, 124, pp. 2098-2099, 2002.

Liu, "Binding of G-quadruplex-interactive agents to distinct G-quadruplexes induces different biological effects in MiaPaCa cells", *Nucleosides, Nucleotides, and Nucleic Acids*, 24, 1801-1815, 2005.

Lucke et al., "Designing scaffolds structures from models of cyclic peptide scaffolds with heterocyclic constraints", *Journal of Molecular Graphics and Modeling*, vol. 21, pp. 341-355, 2003.

Marson, C.M. and M. Saadi, "Synthesis of the penta-oxazole core of telomestatin in a convergent approach to poly-oxazolemacrocycles", Organic & Biomolecular Chemistry, 4(21), 3892-3893, (2006).

Minhas et al., *Biorganic and Medicinal Chemistry Letters*, 16, 3891-3895, 2006.

Nakajima, "Telomerase inhibition enhances apoptosis in human acute leukemia cells: possibility of antitelomerase therapy", *Leukemia*, 17, 560-567, 2003.

Satyanarayana, M., et al., "Ring-closing metathesis for the synthesis of a highly G-quadruplex selective macrocyclic hexaoxazole having enhanced cytotoxic potency", Bioorg. Med. Chem. Lett., 18(13), 3802-4 (Jul. 1, 2008) (Epub May 15, 2008).

Satyanarayana, et al., "Macrocyclic hexaoxazoles: Influence of aminoalkyl substituents on RNA and DNA G-quadruplex stabilization and cytotoxicity", Bioorg. Med. Chem. Lett., vol. 20, pp. 3150-3154, 2010.

Shin-ya, "Telomestatin, a Novel Telomerase Inhibitor from *Streptomyces annulatus*", *J. Am. Chem. Soc.*, 123, 1262-1263, 2001.

Singh et al., "Novel cylindrical, conical, and macrocyclic peptides from the cyclooligomerization of functionalized thiazole amino acids", *J. Am. Chem. Soc.*, vol. 123, pp. 333-334, including 13 supplemental pages, 2001.

Sohda, K, et al., "YM-216391, a Novel Cytotoxic Cyclic Peptide from *Streptomyces nobilis*. I. Fermentation, Isolation and Biological Activities", J. Antibiotics, 58(1), 27-31, (2005).

Sohda, K., et al., "YM-216391, a novel cytotoxic cyclic peptide from *Streptomyces nobilis*. II. Physico-chemical properties and structure elucidation", J. Antibiot. (Tokyo), 58(1), 32-36, (Jan. 2005).

Supplementary European Search Report and European Search Opinion, Application No. EP 07755933.4, 9 pages, Oct. 18, 2011.

Tauchi, "Activity of a novel G-quadruplex-interactive telomerase inhibitor, telomestatin (SOT-095), against human leukemia cells: involvement of ATM-dependent DNA damage response pathways", Oncogene, 22, 5338-5347, 2003.

Wang, "First Total Synthesis of Leucamide A", *J. Org. Chem.*, 68, 1636-1639, 2003.

* cited by examiner

THERAPEUTIC COMPOUNDS

PRIORITY OF INVENTION

This application is a continuation of U.S. patent application Ser. No. 12/258,208, filed on 24 Oct. 2008, now U.S. Pat. No. 8,093,235, which is a continuation of International Patent Application Number PCT/US2007/009862, filed 24 Apr. 2007, which claims priority from U.S. Provisional Application No. 60/794,525, filed 25 April 2006, which applications are incorporated by reference herein in their entirety.

BACKGROUND OF THE INVENTION

A diverse array of compounds, including anthraquinones, acridines, cationic porphyrins, perylenes, thidium derivatives, fluorenones, pentacyclic acridinium salts, fluoroquinophenoxazines, and other specific miscellaneous polycyclic compounds, have been reported to stabilize G-quadruplex DNA. Most of these compounds have little or no selectivity for G-quadruplex vs. duplex DNA.

Telomestatin is a natural product isolated from Streptomyces anulatus 3533-SV4 (Shin-ya et al., *J. Am. Chem. Soc.*, 2001, 123, 1262-1263). At the time of its discovery, telomestatin was viewed as the most potent inhibitor of telomerase. In vitro, telomestatin stabilizes G-quadruplex vs. duplex DNA in a 70:1 ratio (Kim et al., *Cancer Res.*, 2003, 63, 3247-3256). It has been suggested that telomestatin also inhibits telomerase function in vivo, since cells treated with the natural product exhibit a cellular senescence phenotype. Like telomere dysfunction, telomestatin activates the ATM signaling pathway. While the precise mechanism by which telomestatin interacts with a G-quadruplex has not been definitively elucidated, telomestatin does suppress the plating efficiency of K62 leukemia cells but has a much lesser effect on burst-forming units-erythrocyte (BFU-E) and colony-forming units-granulocyte/macrophage (CFU-GM) from natural bone marrow CD34-positive cells (Tauchi et al., *Oncogene*, 2003, 22, 5338-5347).

The anticancer potential of telomestatin resides in its telomerase inhibitory activity ($IC_{50}$ 5 nM) and in its ability to enhance apoptosis. Telomestatin has been evaluated for cytotoxicity in the human neuroblastoma cell lines SK-N-AS, LAN5, WAC2, and LAN1 with $IC_{50}$ values of 0.8, 2.5, 3.2, and 4.0 μM respectively (Binz et al., *Eur. J. Cancer*, 2005, 41, 2873-2881) and in the human pancreatic carcinoma MiaPaCa with an $IC_{50}$ value of 0.5 μM (Liu et al., *Nucleosides, Nucleotides, and Nucleic Acids*, 2005, 24, 1801-1815).

Currently, there is a need for novel therapeutic agents and therapeutic methods that are useful for treating diseases such as cancer. Such agents may have improved binding affinity for G-quadruplex DNA and/or they may have advantageous drug-like properties.

SUMMARY OF THE INVENTION

The present invention provides compounds that stabilize G-quadruplex DNA and that possess anti-cancer properties. Accordingly there is provided a compound of the invention which is compound of formula I:

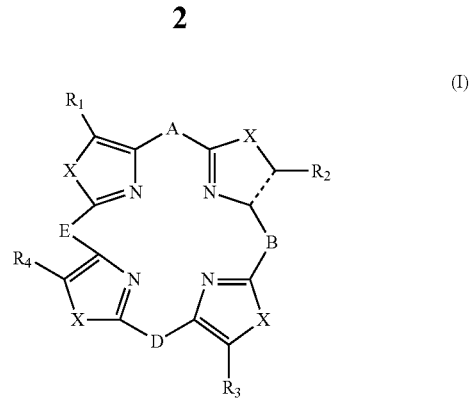

wherein:
each A, B, D, and E is independently —C(=O)NH—CH($R_a$)—, —C(=O)—NH—C(=O)—, or a group of the formula:

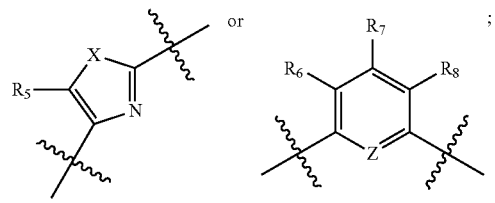

each $R_1$, $R_2$, $R_3$, $R_4$, and $R_5$ is independently H, ($C_1$-$C_6$) alkyl, or ($C_1$-$C_6$)alkoxy, wherein each ($C_1$-$C_6$)alkyl and ($C_1$-$C_6$)alkoxy is optionally substituted with OH, ($C_1$-$C_6$)alkoxy, ($C_1$-$C_6$)alkylthio, aryl, $NR_cR_d$, or —C(=O)$NR_cR_d$;

each $R_6$, $R_7$, and $R_8$ is independently H; or each $R_6$ and $R_7$ together with the atoms to which they are attached form a benzo ring and $R_8$ is H; or $R_6$ is H and $R_7$ and $R_8$ together with the atoms to which they are attached form a benzo ring;

each X is independently NH, S, or O;
each Z is independently N or CH;
the bond represented by — is a single or a double bond;
each $R_a$ is independently H, aryl, or ($C_1$-$C_6$)alkyl that is optionally substituted with OH, ($C_1$-$C_6$)alkoxy, ($C_1$-$C_6$) alkylthio, aryl, $NR_eR_f$, or —C(=O)$NR_eR_f$;

each $R_c$ and $R_d$ is independently H or ($C_1$-$C_6$)alkyl; or $R_c$ and $R_d$ together with the nitrogen to which they are attached form a pyrrolidino, piperidino, piperazino, morpholino, thiomorpholino, or azepino ring; and each $R_e$ and $R_f$ is independently H or ($C_1$-$C_6$)alkyl; or $R_e$ and $R_f$ together with the nitrogen to which they are attached form a pyrrolidino, piperidino, piperazino, morpholino, thiomorpholino, or azepino ring;

or a salt thereof;

provided the compound of formula I is not telomestatin or dehydrotelomestatin.

The invention also provides a pharmaceutical composition comprising a compound of formula I, or a pharmaceutically acceptable salt thereof, in combination with a pharmaceutically acceptable diluent or carrier.

Additionally, the invention provides a therapeutic method for treating cancer comprising administering to a mammal (e.g., a human male or female) in need of such therapy, an effective amount of a compound of formula I, or a pharmaceutically acceptable salt thereof.

The invention provides a compound of formula I or a pharmaceutically acceptable salt thereof for use in medical therapy (e.g., for use in treating cancer), as well as the use of a compound of formula I or a pharmaceutically acceptable salt thereof for the manufacture of a medicament useful for the treatment of cancer in a mammal, such as a human.

The invention also provides processes and intermediated disclosed herein (e.g., novel intermediate compounds included in compounds 100-177) that are useful for preparing compounds of formula (I) or salts thereof.

DETAILED DESCRIPTION

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, iso-propoxy, butoxy, iso-butoxy, sec-butoxy, pentoxy, 3-pentoxy, or hexyloxy; and aryl can be phenyl, indenyl, or naphthyl.

A specific group of compounds are compounds wherein A and D are each independently a group of the following formula:

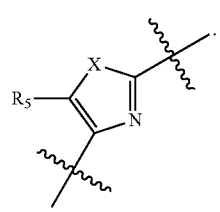

A specific value for X is O.

A specific value for the bond represented by — is a double bond.

A specific group of compounds are compounds wherein B and E are each independently —C(=O)NH—CH($R_a$)—.

A specific value for $R_a$ is H, methyl, isopropyl, 2-methyl-propyl, benzyl, 3-(N,N-dimethylamino)propyl, or 4-(N,N-dimethylamino)butyl.

A specific group of compounds are compounds wherein A, B, and D are each independently a group of the following formula:

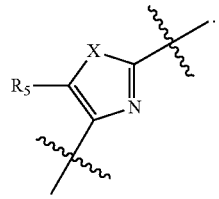

A specific value for E is —C(=O)NH—CH($R_a$)—.

A specific group of compounds are compounds wherein A, B, D, and E are each independently a group of the following formula:

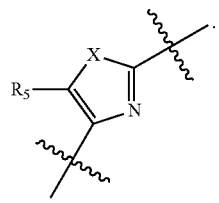

A specific value for each $R_1$, $R_2$, $R_3$, $R_4$, and $R_5$ is independently H or $(C_1-C_6)$alkyl that is substituted with OH, $(C_1-C_6)$alkoxy, $(C_1-C_6)$alkylthio, aryl, $NR_cR_d$, or —C(=O)$NR_cR_d$.

A specific value for each $R_1$, $R_2$, $R_3$, $R_4$, and $R_5$ is independently H or $(C_2-C_6)$alkyl that is optionally substituted with OH, $(C_1-C_6)$alkoxy, $(C_1-C_6)$alkylthio, aryl, $NR_cR_d$, or —C(=O)$NR_cR_d$.

A specific group of compounds are compounds wherein each B and E is independently a group of the formula:

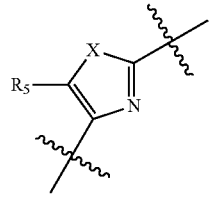

and each A and D is independently group of the formula:

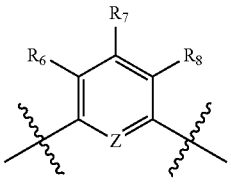

A specific value for Z is N.
A specific value for Z is CH.
A specific group of compounds are compounds wherein each A, B, D, and E is independently a group of the formula:

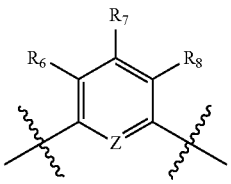

A specific group of compounds are compounds wherein A and D are each independently a group of the following formula:

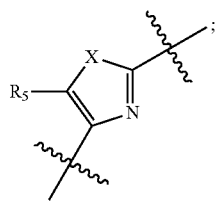

B is —C(=O)—NH—C(=O)—; and
E is —C(=O)NH—CH($R_a$)—.

A specific group of compounds are compounds wherein A and D are each independently a group of the following formula:

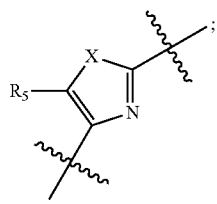

and
B and E are each independently —C(=O)NH—CH($R_a$)—.

A specific compound of the invention is a compound of formula (II):

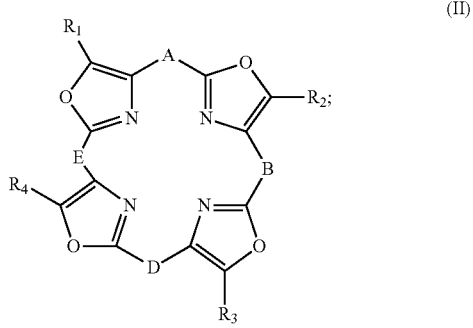

(II)

or a pharmaceutically acceptable salt thereof.

Processes for preparing compounds of formula I are provided as further embodiments of the invention and are illustrated by the following procedures in which the meanings of the generic radicals are as given above unless otherwise qualified.

Methods of Preparation

Hexa-Oxazoles

This series of compounds can be prepared by using intermediates comprised of alternating oxazole and amino acid units as outlined in Scheme 1. Initially, cyclic tetraoxazole intermediates are synthesized from which further interconnected oxazole rings can be generated. Such intermediates can be prepared by condensation of the N-Boc derivatives of amino acids such as valine, leucine, alanine or an appropriately substituted α-amino acid (assuming that appropriate protecting groups are employed) and an O-protected serine methyl ester employing either 1-(3-dimethylaminopropyl)-3-ethylcarbodiimide hydrochloride (EDC) in the presence of 1-hydroxybenzotriazole (HOBt) and base, or benzotriazol-1-yloxytris(dimethylamino)phosphonium hexafluorophosphate (BOP) with triethylamine. In this manner, the resulting amides 101 can be prepared in good yield. Cyclodehydration can be achieved using (diethylamino)sulfur trifluoride (DAST) giving the corresponding oxazolines 102. Dehydrogenation to the oxazole derivatives 103 can be performed using bromotrichloromethane in the presence of 1,8-diazabicyclo[5.4.0]undec-7-ene (DBU). One portion of each of the oxazoles can then be hydrolyzed to carboxylic acids 104 using lithium hydroxide in aqueous methanol or THF. Another portion can be treated with equal amounts of trifluoroacetic acid (TFA) in methylene chloride to afford the deprotected amines 105. Oxazoles having a free amino group, such as 105, can be coupled with others having a 4-carboxylic acid moiety, such as 104, using BOP to provide the key structural intermediate 106 possessing two oxazole rings separated by an α-amino acid residue. Again, portions of these intermediates can be treated with either LiOH to give the 4'-carboxylic acid derivatives 107 or with TFA to give the unprotected amino derivatives 108. Coupling of 107 and 108 with BOP will provide 109, which can be deprotected sequentially with TFA, and then LiOH to provide 110. Macrocyclization of 110 can be achieved using BOP in the presence of diisopropylethylamine (DIPEA) in DMF/acetonitrile (7:1) under high dilution (0.007M) conditions to yield the appropriately substituted tetra-oxazole, 111.

Scheme 1.

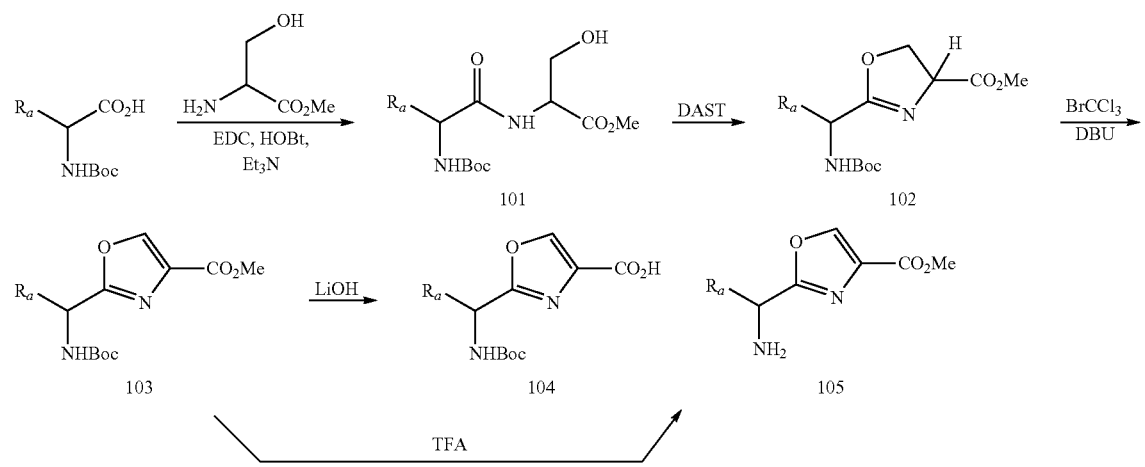

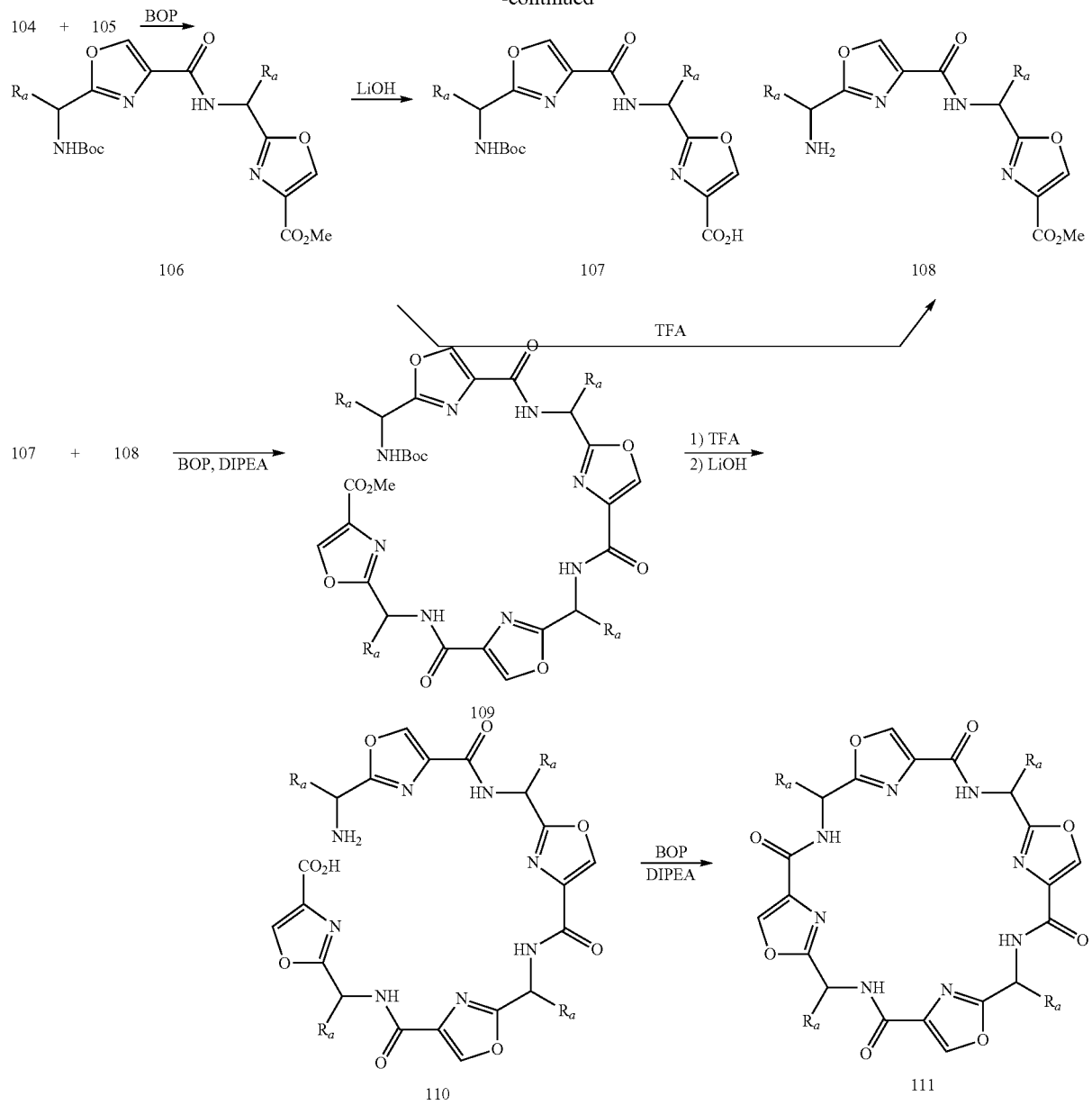

Hexa-oxazole compounds can be prepared from tetra-oxazoles where two of the R-substituents consist of a hydroxymethyl group as outlined in Scheme 2. The hydroxyl group in such instances can be protected by the formation of tert-butyldiphenylsilyl (TBDPS) ethers as represented by the specific intermediate 111a. Methods for the preparation of 114a and 114b illustrate the general method by which one can convert such tetra-oxazoles intermediates into hexa-oxazoles. Treatment of 111a with HF will efficiently remove the tert-butyldiphenylsilyl (TBDPS) ethers. The resulting diol 112a can then be cyclodehydrated using DAST to give the resulting bis-oxazoline 113a, which can be aromatized to 114a upon treatment with bromotrichloromethane and DBU. The macrocycle 111b, which is illustrated with two different silyl ether protecting groups on the hydroxymethyl groups designated as $R_1$ and $R_2$ can be treated with camphorsulfonic acid (CSA) in methanol and methylene chloride to selectively remove the tert-butyldimethylsilyl (TBS) groups to give diol 112b. Treatment of 112b with DAST can provide 113b. Aromatization of the two oxazoline rings would yield 114b.

Scheme 2.

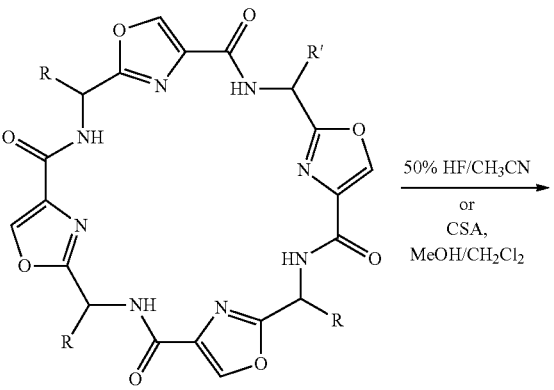

111a R = iPr, $R^2$ = CH$_2$OTBDPS
111b R = CH$_2$OTBPS, $R^2$ = CH$_2$OTBS

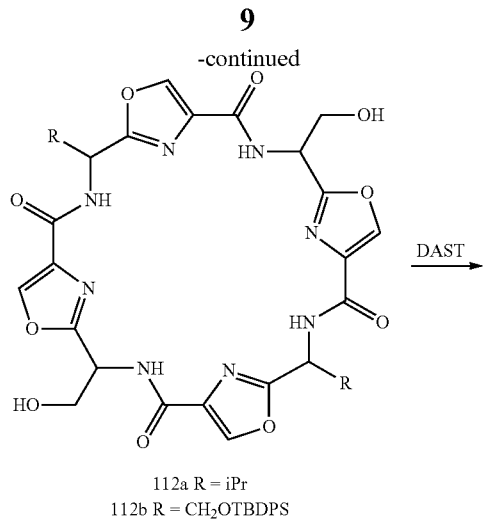

112a R = iPr
112b R = CH₂OTBDPS

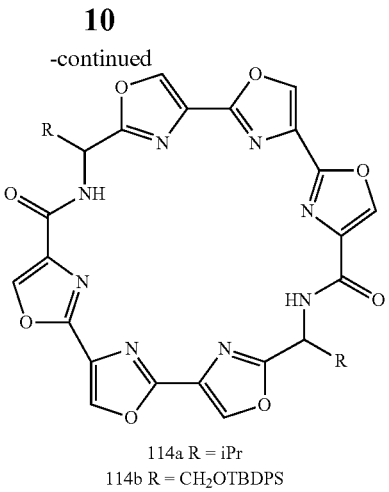

114a R = iPr
114b R = CH₂OTBDPS

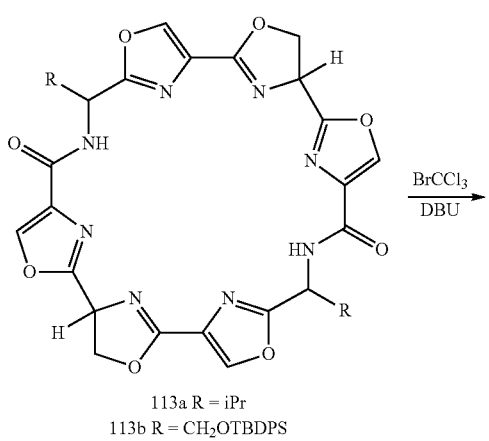

113a R = iPr
113b R = CH₂OTBDPS

Hepta-Oxazoles

Macrocyclic dihydroheptaoxazoles 120 and heptaoxazoles 121 containing varied R substituents can be prepared as illustrated in Scheme 3. When $R^4$ is a benzyl ether on intermediate 108 (whose synthesis was described in Scheme 1) one has intermediate 108a, which can be hydrogenolyzed over palladium hydroxide to give its corresponding alcohol derivative. Such hydroxymethyl groups upon treatment with DAST will cyclize to a dihydrooxazole which can be dehydrogenated with bromotrichloromethane to give the teroxazole 115, where R is a number of varied alpha-substituents, which have standard protecting groups as required. Treatment of 115 with TFA will remove the Boc-protecting group and provide the amine 116. Hydrolysis of 115, where R=tert-butyldiphenylsilyl (TBDPS) with LiOH will provide 117. Treatment of a mixture of 116 and 117 with BOP provides the amide 118. The Boc group can then be removed with TFA, the ester hydrolyzed and the resulting compound macrocyclized using BOP to give lactam 119. The TIPS group can be removed by treatment with concentrated HCl in methanol and methylene chloride to give the alcohol. The alcohol can be oxidized to an aldehyde using Dess-Martin periodinate and cyclized to hepatoxazole 121 using triphenylphosphine and iodine with triethylamine.

Scheme 3.

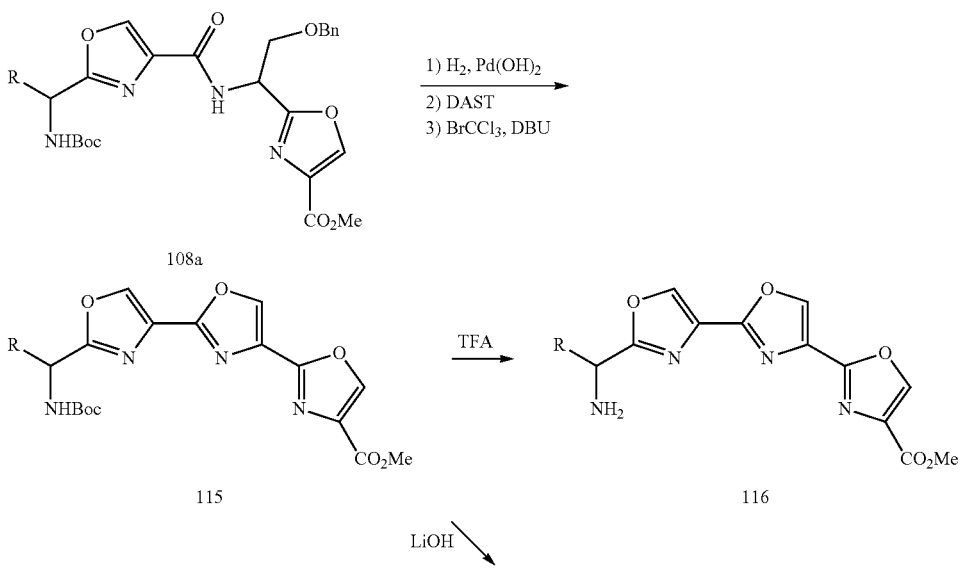

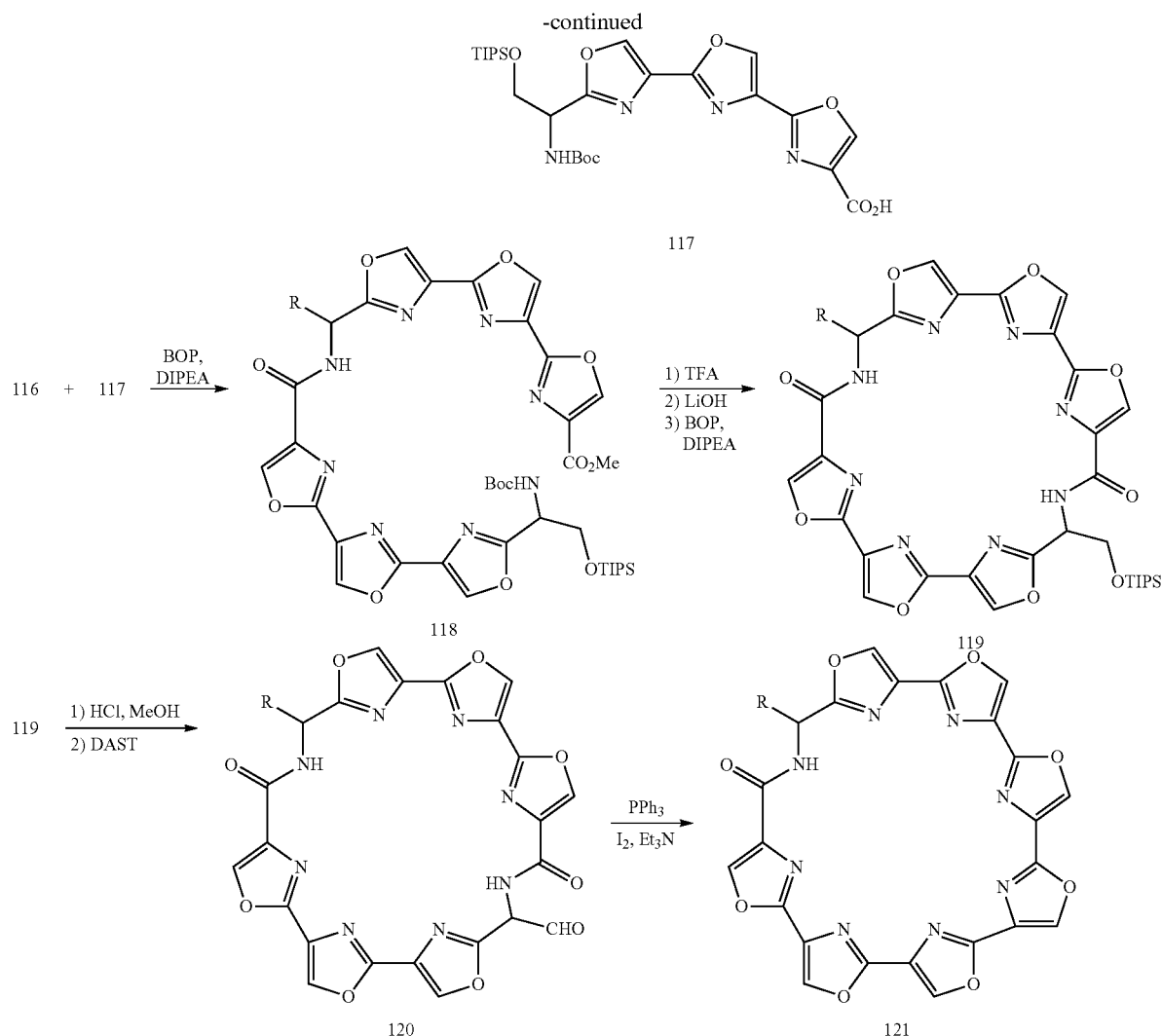

Octa-Oxazoles

A convergent approach to the synthesis of octa-oxazoles can be employed as outlined in Scheme 4. Teroxazole 122 (which was prepared by forming the benzyl ester from acid 117) will be treated with HF-pyridine complex to remove the TIPS group. The resulting alcohol will be oxidized with $RuCl_3/NaIO_4$ to give a carboxylic acid that will then be converted into methyl ester 123. A portion of 123 will be treated with TFA to remove the Boc group to give amine 124. Another portion of 123 will be converted into carboxylic acid 125 by selective hydrogenolysis of the benzyl ester. Coupling of 124 and 125 will give amide 126. Treatment with TFA followed by hydrogenolytic removal of the remaining benzyl ester, and macrocyclization with BOP will form bislactam 127. After ester hydrolysis, warming with acetic anhydride and then treatment with triflic anhydride will give the bis (triflate) derivative 128. The same series of reactions employed above for heptaoxazoles herein will be used to prepare disubstituted octaoxazole torands 129a-c.

Scheme 4.

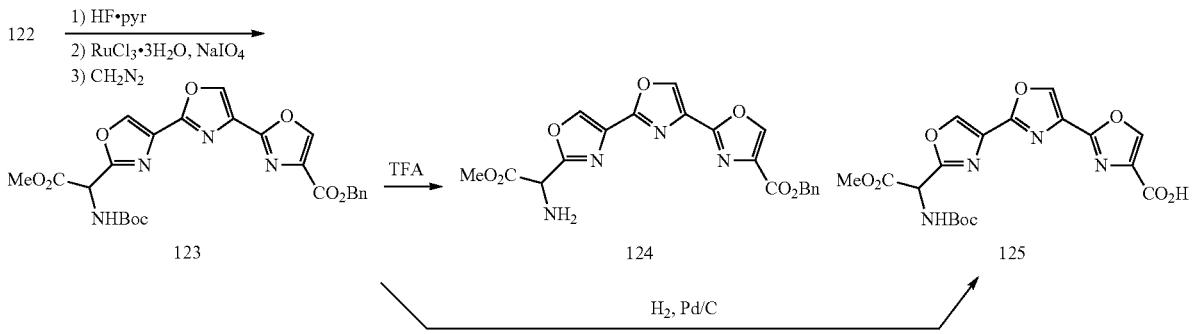

-continued
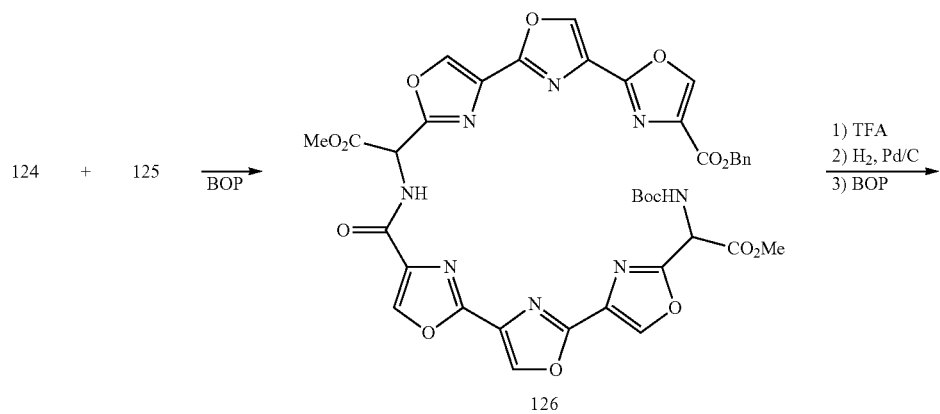
126
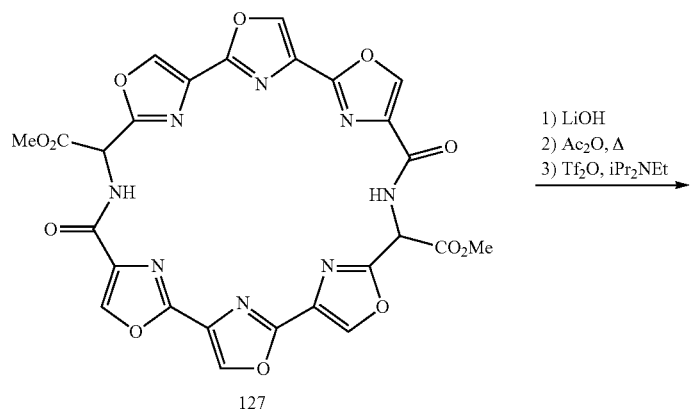
127
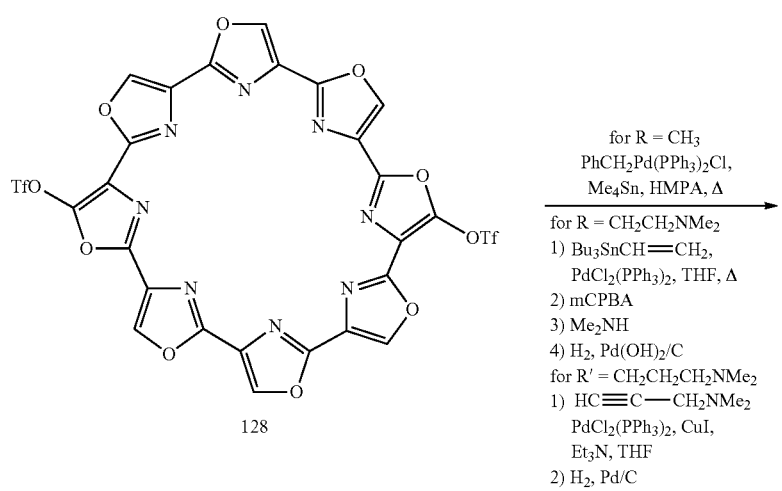
128

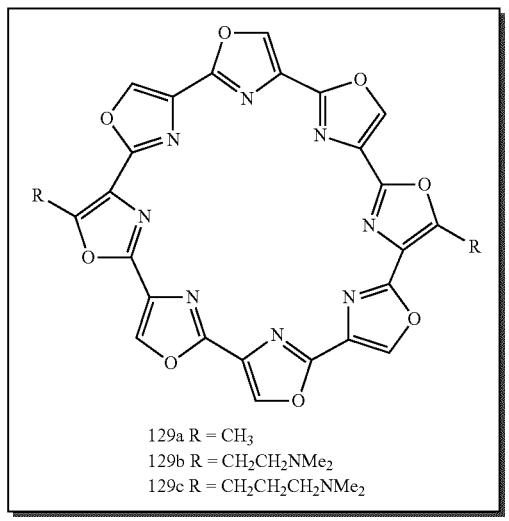

129a R = CH₃
129b R = CH₂CH₂NMe₂
129c R = CH₂CH₂CH₂NMe₂

Synthesis of Hexa-, Hepta, and Octa-oxazole Analogs Having Basic Side Chains

The presence of alkyl side chains possessing basic functional groups may stabilize the interaction between the substrate and the G-quadruplex structure by providing for hydrogen bonding with the phosphate backbone. The presence of these substituents should also improve water solubility by providing a handle for salt formation. Two such groups on non-adjacent oxazole rings may magnify the binding affinity for G-quadruplex relative to duplex DNA. Methods have been outlined for the synthesis of hexa-, hepta, and oct-oxazoles having a single 2-(N,N-dimethylamino)ethyl chain on rings B, C, or D of a hexa-oxazole (see Figure A), and B, C, E or G of hepta- and octa-octazoles. Several analogs having two 2-(N,N-dimethylamino)ethyl chains on rings B & G and C & G, or in the case of hepat and octa-oxazoles C & E or E & G. Similar methodology can be used to prepare macrocyclic hexa-, hepta- or octaoxazoles having one or two ω-aminoalkyl chains in which the amine is substituted with H, alkyl, acetyl, or Boc groups.

FIGURE A.

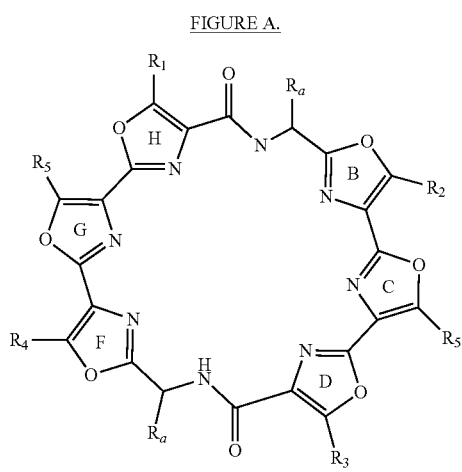

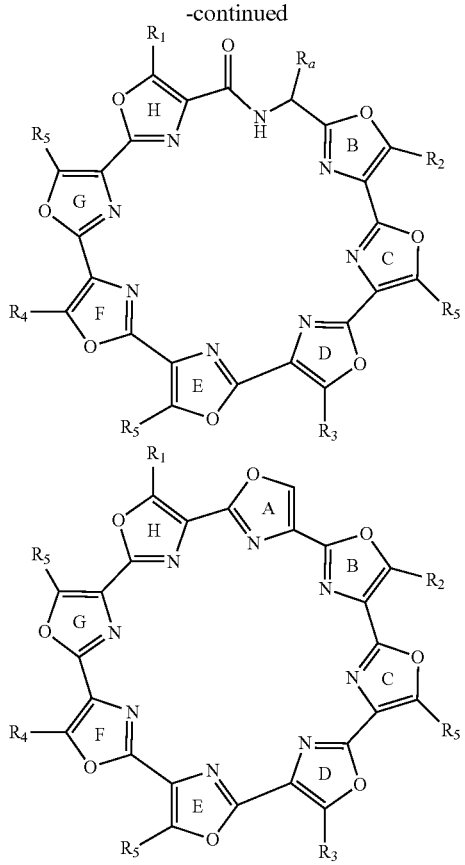

While the overall strategies for the synthesis of these analogs are the same to that used for hexa-, hepta- and octa-oxazoles and their intermediates, the presence of such aminoalkyl substituents at these various sites require the preparation of appropriately substituted teroxazoles. While there are various suitable methods available for the preparation of such teroxazole, representative methods are illustrated below for several such key intermediates (see Section A). In addition, one can generate an aminoalkyl oxazole from an appropriately substituted oxazole with a cyclic hexa- or hepta oxazole (see Section B). These methods are also illustrated below.

Section A. Synthesis of Teroxazole Intermediates:

Synthesis of the 4-[2-(N,N-dimethylamino)ethyl]teroxazole, Compound 133

Lithiation of 130 followed by reaction with 3-(dimethylamino)propionaldehyde will give alcohol 131. Mercury catalyzed hydrolysis of the dithiane to a ketone, followed by oxime formation and then reduction will lead to amino alcohol 132. Amidation with O-benzyl-NH(Fmoc)-L-serine, followed by Dess-Martin oxidation, oxazole formation, and removal of the Fmoc group will yield substituted teroxazole 133.

utility of a multi-functionalized central oxazole similar to that described in the synthesis above. To that end, the immediate product of reaction of aldehyde 134 with trimethylsilylacetylene, LiHMDS, and the acid chloride of 1,3-dithiane-2-carboxylic acid, after treatment with sodium hydride should be 5-(trimethylsilyl)methyl derivative 135. Treatment with bromine and CsF at low temperature, followed by a quench with excess cyclohexene to prevent ring bromination is expected to give bromomethyl derivative 136 directly. An alternative preparation of 136 from methyl derivative 130 is possible by treatment with N-bromosuccinimide and a free-radical initiator in a non-protic solvent, conditions under which the dithiane is stable. Stille coupling of 136 with 1-(N,N-dimethylamino)methyltributylstannane will lead to bisoxazole 137. This will be elaborated into teroxazole 138.

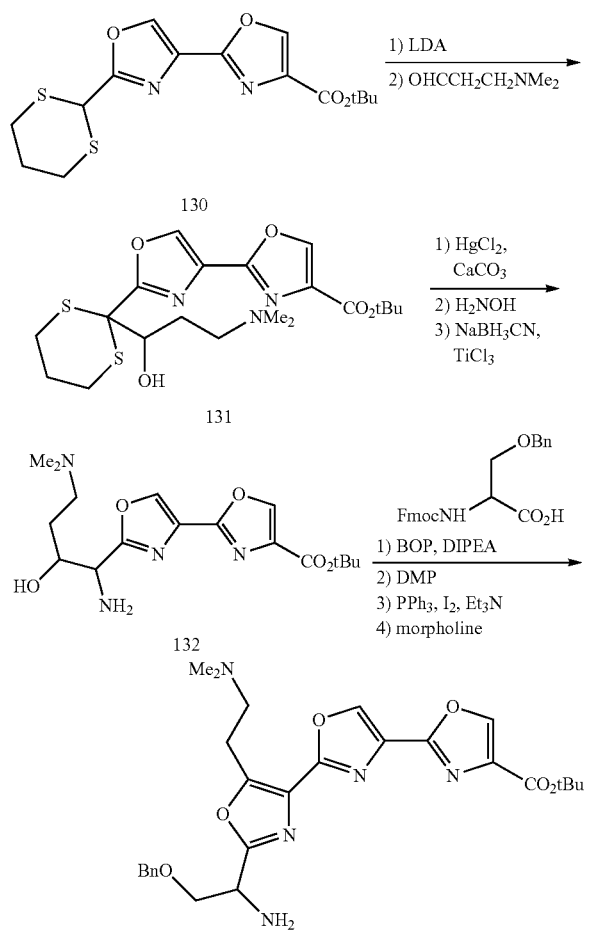

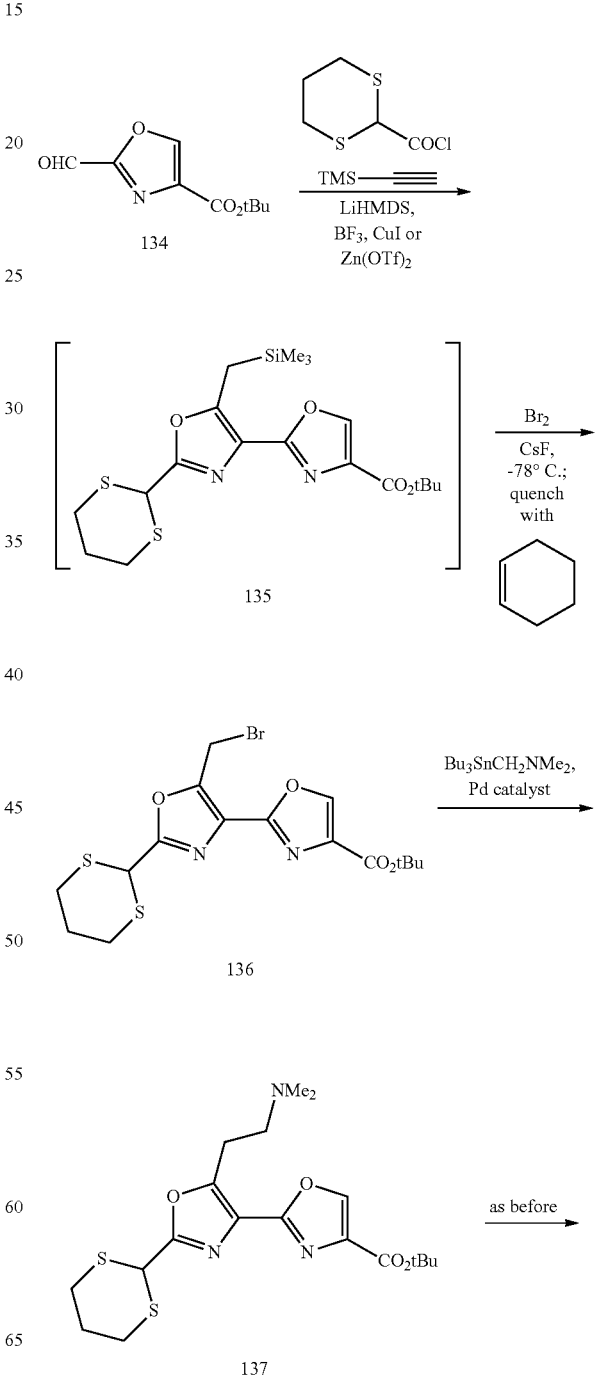

Synthesis of 4-[2-(N,N-dimethylamino)ethyl]teroxazole, Compound 138

There are at least two methods for the formation of a teroxazole which has an 2-N,N-dimethylaminoethyl intermediate on the central oxazole unit. The first seeks to expand the

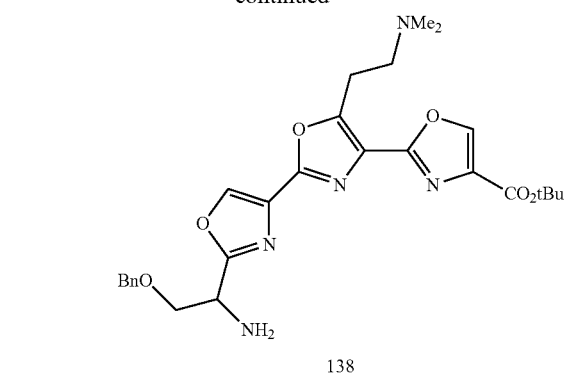

138

An alternate approach to 137 employs 3-dimethylamino-1-propyne as the acetylene in the multi-component coupling reaction, which should yield 137 directly upon workup of the reaction. Zinc triflate has been employed previously in Lewis acid catalyzed reactions in the presence of tertiary amines.

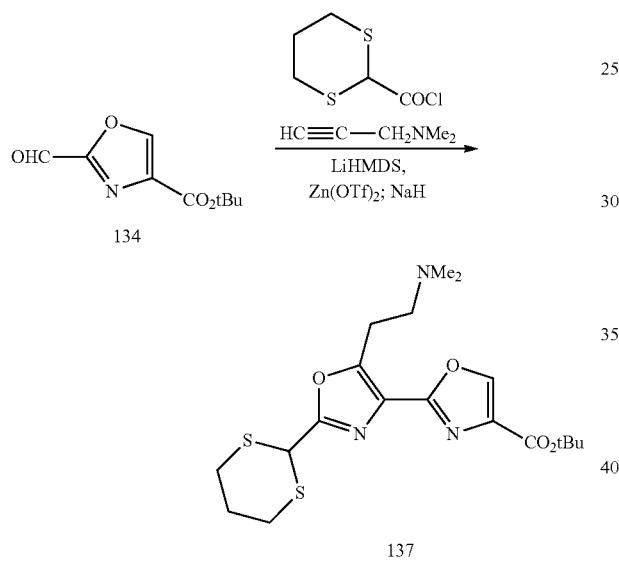

Synthesis of 4-[2-(N,N-dimethylamino)ethyl]teroxazole, Compound 143

Amide 139 will be oxidized to an aldehyde and converted into β-hydroxysilane 140 as described above. Oxidation to the ketone and cyclodehydration using Wipf's procedure will furnish teroxazole 141. Bromodesilylation and Stille coupling, as detailed previously, followed by ester hydrolysis will give 142.

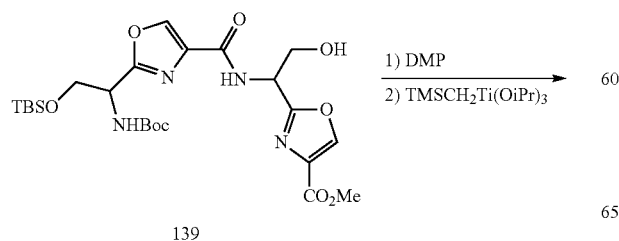

139

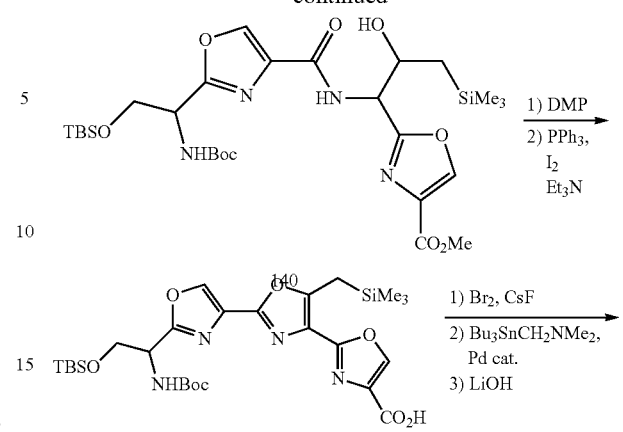

Section B. Methods to Convert a Hexa- or Hepta-Oxazole Macrolide into a Hepta- or Octa Oxazole, which Possesses a 4-[2-(N,N-Dimethylamino)ethyl] Substituent within the Newly Generated Oxazole Macrocycle 125 will be oxidized with Dess-Martin periodinane (DMP) and the resulting aldehyde reacted chemoselectively with (trimethylsilyl)methyl-titaniumtriisopropoxide to give alcohol 143. A second Dess-Martin oxidation followed by treatment with triphenylphosphine and iodine will form heptaoxazole 144. Replacement of the silane with bromine, and Stille coupling with 1-(N,N-dimethylamino)methyltributylstannane will furnish key intermediate 145 which will then be converted as described.

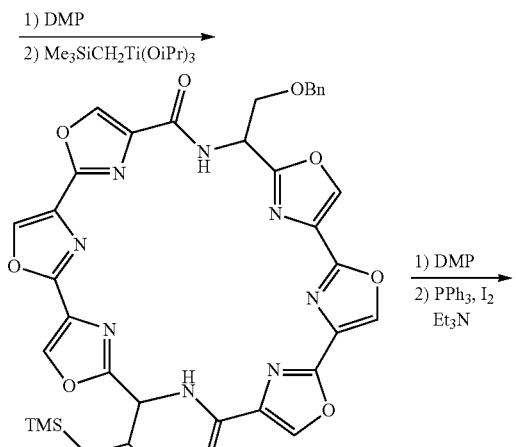

143

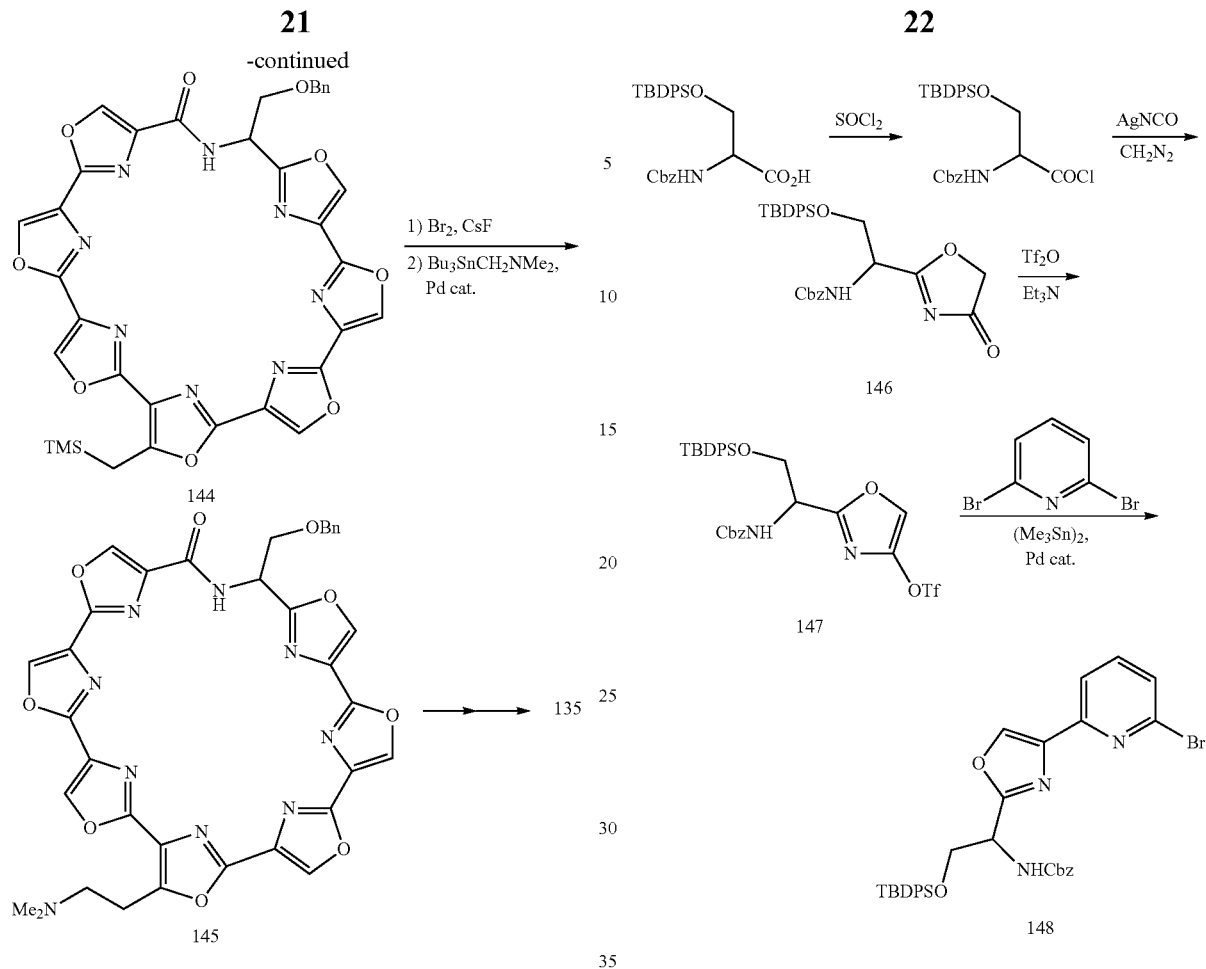

Synthesis of Hexa-, Hepta- and Octa-oxazoles with Two Basic Side Chains

Analogs having two side chains can be prepared from the appropriate teroxazoles. Some specific examples can be assembled from teroxazoles 138 and 142. Joining of teroxazoles 122 and 138 provides a suitable intermediate for the formation of a 4-substituted oxazole that will permit the formation of aminoalkyl substitutents on the rings of either a hepta- or octa-oxazole. Similar compounds can also be prepared from teroxazoles 123 and 142.

Mixed Torands
Series A

Representative macrocyclic torands 160-162 can be prepared as illustrated below. The synthesis of torands consisting of two pyridine rings are detailed. N-Cbz-O-TBDPS serine will be converted into an acid chloride and then reacted with silver isocyanate followed by treatment with diazomethane to give oxazolone 146. This will be treated immediately with triflic anhydride and base to form oxazole triflate 147. This will be joined with 2,6-dibromopyridine via a Stille coupling to give intermediate 148. In the event that both bromines on the pyridine undergo facile Stille coupling to give a 2,6-di (oxazolyl)pyridine derivative, Suzuki coupling of triflate 147 with 6-bromo-2-pyridylboronic acid will give 148 selectively. One could replace the pyridine in intermediate 148 with phenyl by using either 3-bromophenyl boronic acid in place of 6-bromo-2-pyridylboronic acid in the Suzuki coupling reaction.

The second oxazole coupling partner will be prepared by reaction of the zinc enolate of methyl N-Boc glycinate with 3-(N,N-dimethylamino)propionaldehyde. Alcohol 149 will be oxidized with Dess Martin periodinane and the Boc group removed with TFA to give ketone 150. Condensation with phosgene in the presence of base will give oxazolone 151, which will be converted into triflate 152 using the procedure of Panek.

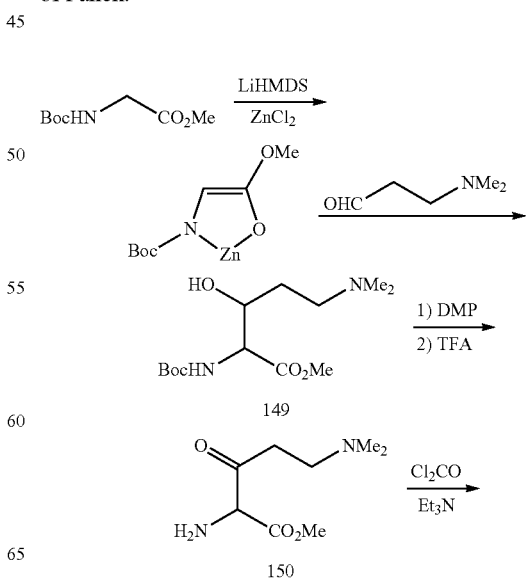

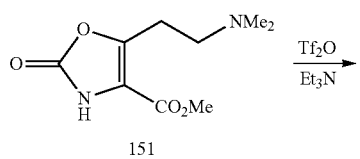

Stille coupling of triflate 152 with bromopyridine 148 in the presence of hexamethylditin will give bis(oxazolyl)pyridine 153. A portion of this will be hydrolyzed with LiOH and the TBDPS group will then be removed with tetrabutylammonium fluoride (TBAF) to give acid 154. The remainder of 153 will be converted into amine 155 by hydrogenolysis of the Cbz group.

BOP-mediated coupling of 154 and 155 will give amide 156. Hydrogenolysis of the Cbz group, hydrolysis of the ester and macrolactamization with BOP will give 157. Macrocyclic pentaoxazole 158 will be formed by cyclodehydration of the primary alcohol with DAST, dehydrogenation with bromotrichloromethane, and removal of the silyl group with TBAF.

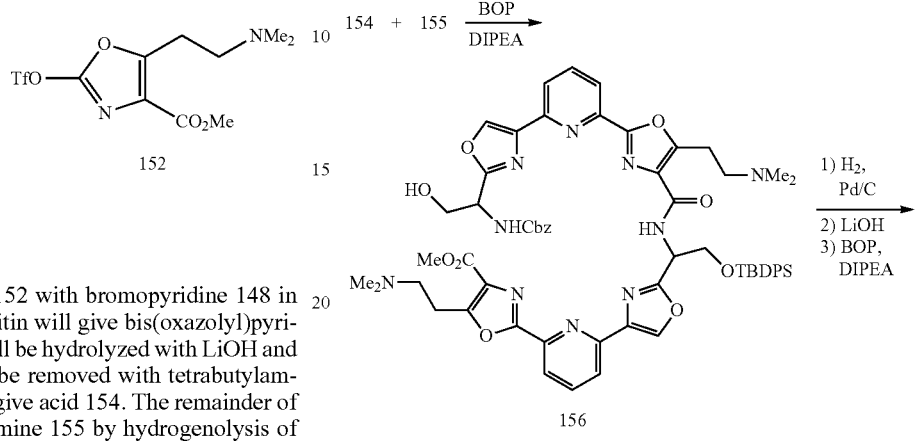

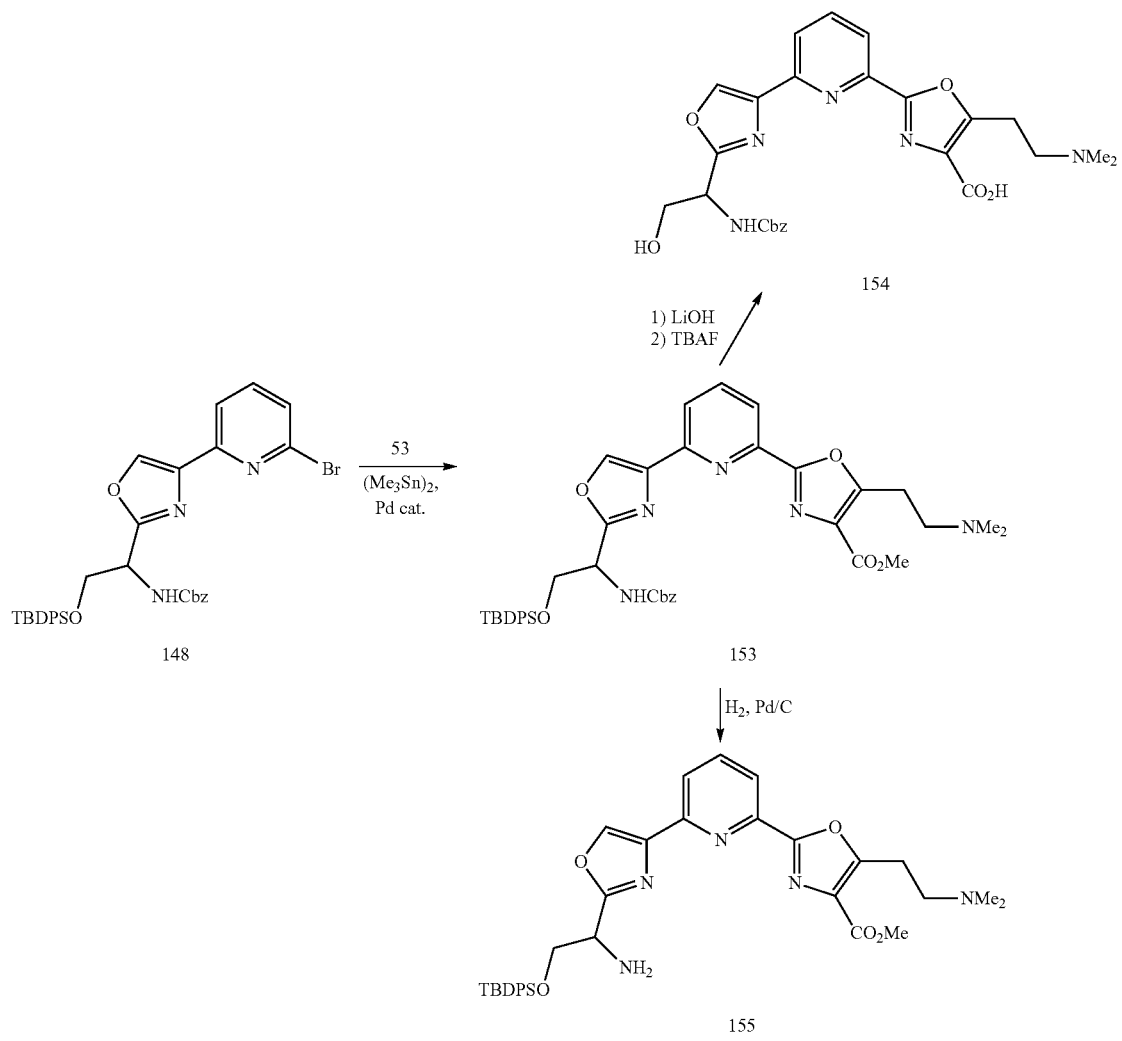

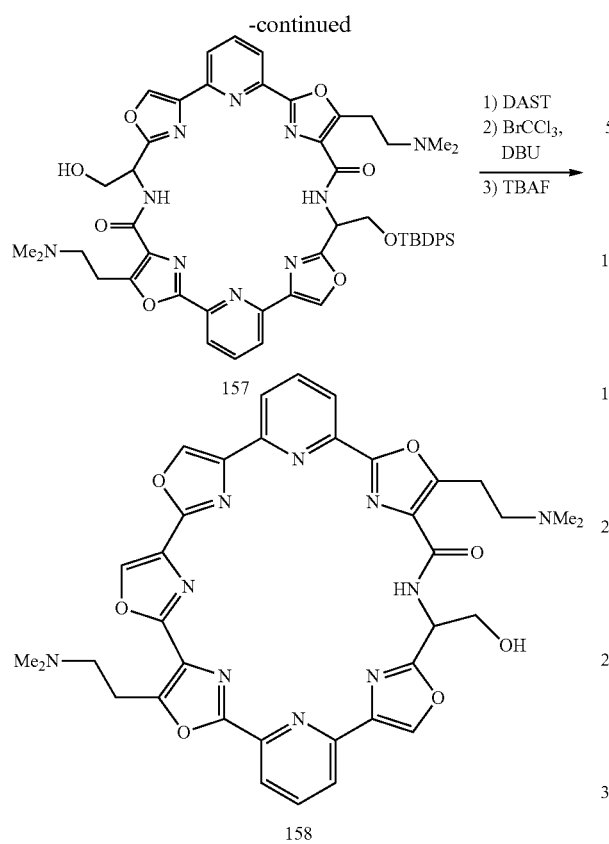

157

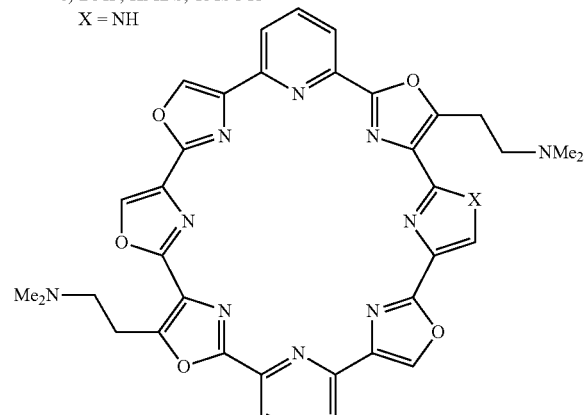

158

Series A analogs 159, 160, and 161 are prepared from common intermediate 158. Treatment with DAST and then bromotrichloromethane and DBU will give oxazole 159. Thiazole 160 will result from treatment of 158 with Lawesson's reagent, followed by DAST and BrCCl₃/DBU. Dess Martin oxidation of 158 and then reaction with HMDS in the presence of TMSOTf will give imidazole 161.

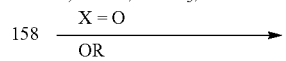

a) DAST; BrCCl₃, DBU
    X = O
OR
b) Lawesson's reagent,
    DAST; BrCCl₃, DBU
    X = S
OR
c) DMP; HMDS, TMSOTf
    X = NH

159 X = O
160 X = S
161 X = NH

Macrocycle 157 will serve as common intermediate to several Series A analogs such as 159, 162, and 163. Treatment of 157 with TBDPSCl and then Lawesson's reagent will give a bis(thiolactam). Removal of the silyl protecting groups with TBAF followed by treatment with DAST and then bromotrichloromethane and DBU will give symmetrical bis(thiazole) analog 162 (X,Y=S). For the symmetrical imidazole analog 163 (X,Y=NH) treatment of 158 with TBAF and then Dess-Martin oxidation will form an aldehyde intermediate that will be converted into an imidazole via the N-trimethylsilylimine using HMDS and TMSOTf. Unsymmetrical analog 166 (X=S, Y=NH) will be prepared from 157 by Dess-Martin oxidation of the primary alcohol and conversion into the imidazole with HMDS and TMSOTf. Treatment with Lawesson's reagent will then give a thiolactam. The silyl group (TBDPS) will be removed with TBAF and the thiazole will then be formed upon cyclodehydration with DAST followed by dehydrogenation with bromotrichloromethane and DBU.

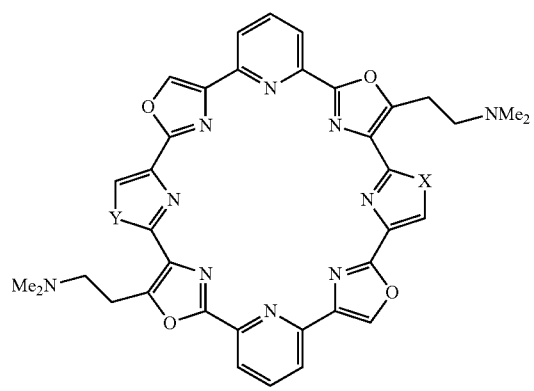

163 X = O, Y = O
164 X = S, Y = S
165 X = NH, Y = NH
166 X = O, Y = S
167 X = O, Y = NH
168 X = S, Y = NH

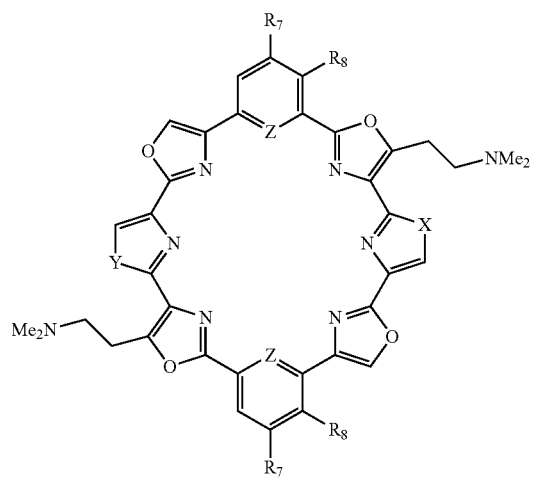

X = O, S, or N
Y = O, S, or N
Z = N or CH
R₇R₈ = Benzo

Mixed Torands
Series B

Commercially-available methyl 6-bromopyridine-2-carboxylate can be converted into an organozinc derivative using Rieke zinc. This can be coupled with benzyloxyacetyl chloride in the presence of copper cyanide to give ketone 169. Conversion into an oxime followed by reduction will give amine 170. One can then protect the amine as a 9-fluorenylmethyl carbamate (Fmoc) followed by hydroylsis of the ester with ultimate conversion of the hydrolysis product into acid chloride 171. This can be subjected to multi-component coupling with pyridyl aldehyde 172, 3-dimethylamino-1-propyne, and LiHMDS in the presence of zinc triflate, followed by treatment, in situ, with catalytic sodium hydride to provide oxazole 173. Benzyl 6-formyl-2-pyridinecarboxylate 172 can be prepared from 2,6-pyridinedicarboxylic acid by a known three-step procedure. A portion of 173 will be treated briefly with morpholine to remove the Fmoc group, to give amine 174. A second portion of 173 will be hydrolyzed to acid 175. Coupling of 174 and 175 with BOP will give amide 176. Hydrogenolysis of the remaining Fmoc group, the benzyl ester, and the benzyl alcohols with ammonium formate in dioxane-methanol, followed by macrocyclization with BOP will give bislactam 177 as a common intermediate for analogs 178-181. Compound 178 (X=O) can be prepared from 177 by treatment with DAST followed by bromotrichloromethane and DBU. Thiazole analogs 179 (X=S) can be prepared from 177 by treatment with Lawesson's reagent to form a bis (thiolactam). Cyclization with DAST and dehydrogenation with bromotrichloromethane and DBU will furnish macrocycle 179. For analog 180a 2,4-disubstituted imidazoles, alcohol 177 will be oxidized to the corresponding aldehyde with Dess-Martin periodinane. Reaction with hexamethyldisilazane (HMDS) the presence of trimethylsilyl trifluoromethanesulfonate (TMSOTf) should furnish macrocyclic bis(imidazole) 180 via the N-trimethylsilylimine. While β-amido ketones can be converted into 5-substituted imidazoles in the presence of ammonia and an acid catalysis, the analogous reaction of aldehydes to 5-unsubstituted imidazoles is not as well known. Evans reported in his synthesis of Diphthamide conversion of a serine derivative, via Swern oxidation to the aldehyde and imine formation with benzylamine. The N-benzylimidazole was then formed by cyclization using triphenylphosphine and hexachloroethane. Hydrogenolysis over palladium black then removed the benzyl group to give the 1H-imidazole. The reaction of HMDS with aldehydes in the presence of a Lewis acid results in the formation of N-trimethylsilylimines. These species behave as nucleophiles and can attack other carbonyl groups. It is proposed that the N-silylimine 182 derived from aldehyde 181 will attack the amide carbonyl in the presence of TMSOTf or another Lewis acid, and after N— to O— transfer of the silyl group, the electron pair from the amide nitrogen will eliminate the O-TMS group. A [1,3] sigmatropic hydrogen shift will complete the imidazole synthesis, with the driving force being establishment of aromaticity in the ring.

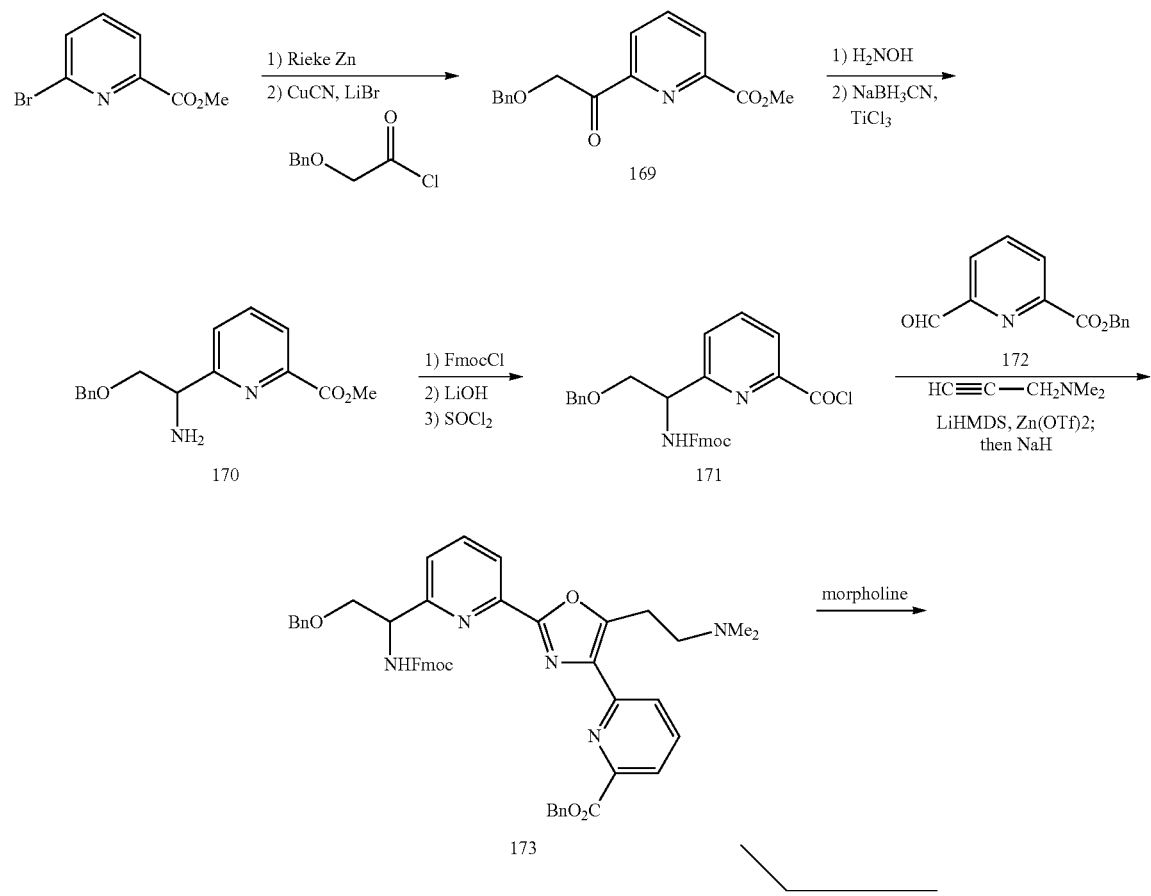

-continued
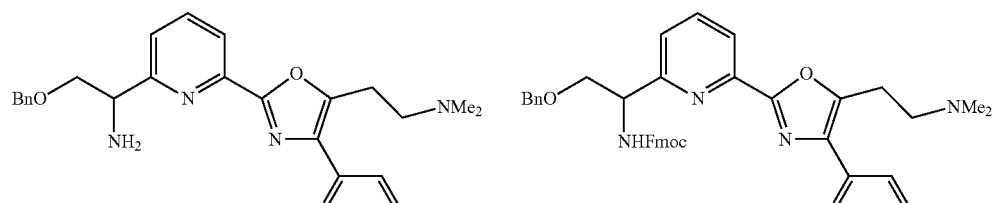
174
175
LiOH
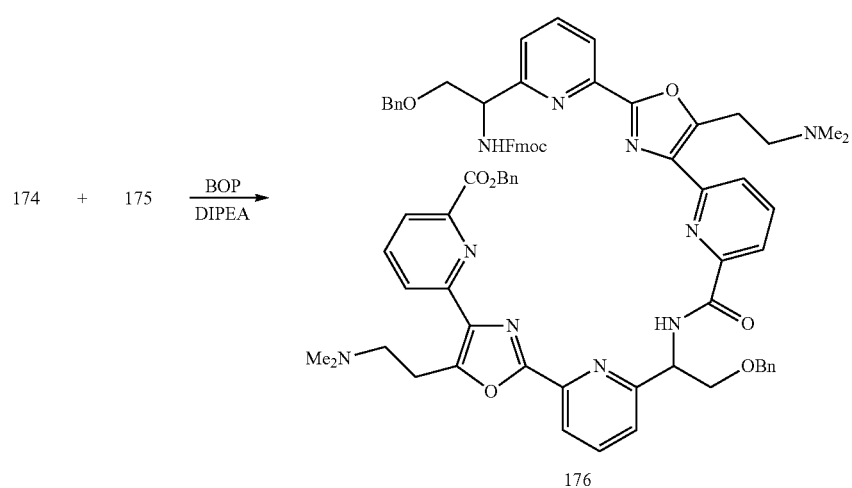
174 + 175 →[BOP, DIPEA]
176
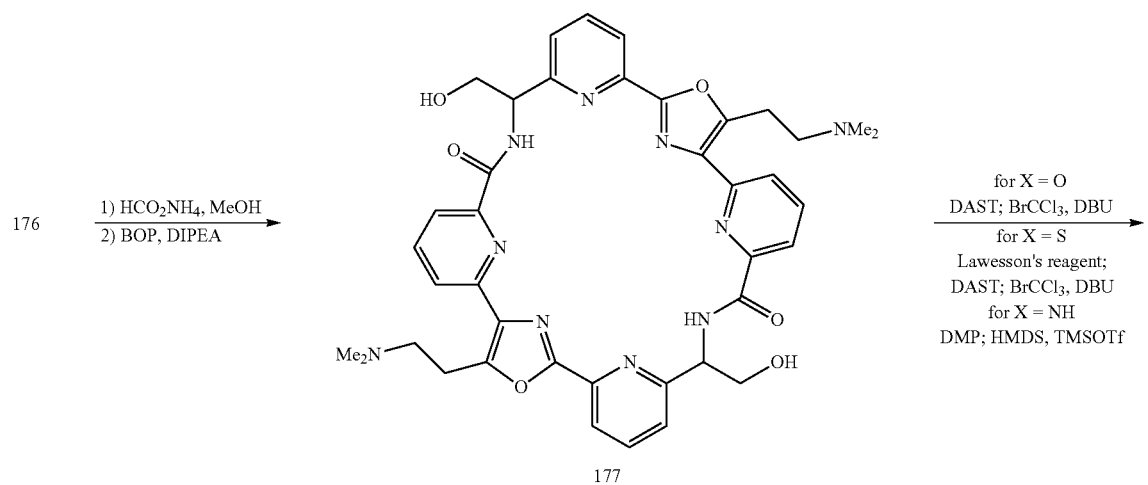
176 →[1) HCO$_2$NH$_4$, MeOH; 2) BOP, DIPEA]
177
for X = O
DAST; BrCCl$_3$, DBU
for X = S
Lawesson's reagent;
DAST; BrCCl$_3$, DBU
for X = NH
DMP; HMDS, TMSOTf

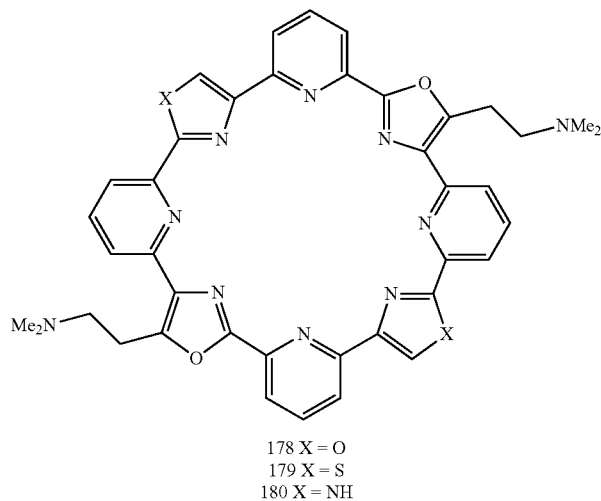

178 X = O
179 X = S
180 X = NH

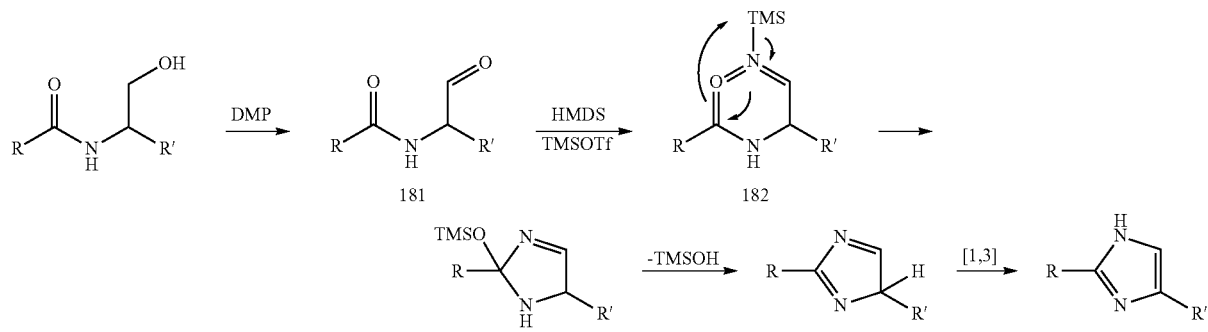

As noted in Series A, one can develop torands wherein two alternating phenyls can replace the pyridyl moiety by using commercially-available 3-bromobenzoic acid methyl ester in place of methyl 6-bromopyridine-2-carboxylate or by using 3-formylbenzoic acid benzyl ester place of benzyl 6-formyl-2-pyridinecarboxylate. One can also replace all four pyridine moieties within these torands by using both commercially-available 3-bromobenzoic acid methyl ester in place of methyl 6-bromopyridine-2-carboxylate and 3-formylbenzoic acid benzyl ester place of benzyl 6-formyl-2-pyridinecarboxylate. Use of appropriately substituted naphthalene and isoquinoline derivatives provides a convenient route wherein $R_6$ and $R_7$ or $R_7$ and $R_8$ represent a benzo-fused ring in the general structure provided below for these mixed torands.

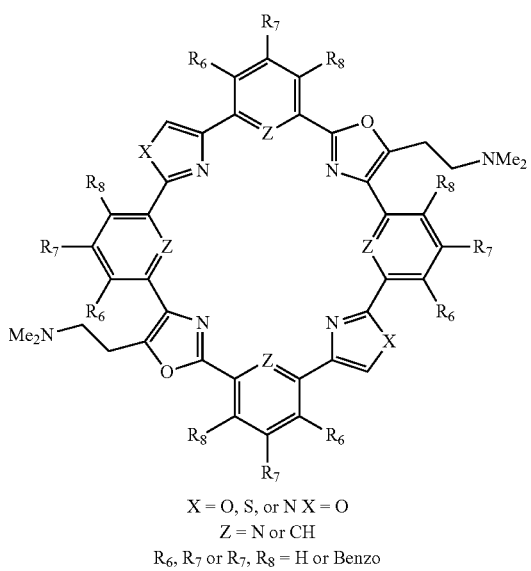

X = O, S, or N X = O
Z = N or CH
$R_6$, $R_7$ or $R_7$, $R_8$ = H or Benzo

Hydroxyhepta-Oxazoles and Hydroxyocta-Oxazoles

These useful torands can be prepared by a modification in the cyclization conditions used to form one or more oxazoles within a preformed macrocycle.

A. Hydroxyhepta-Oxazoles

Using the methods previously outlined, suitably substituted teroxazoles will be coupled using BOP or similar acylation catalyst. After protecting group removal, cyclization with BOP will give the macrocyclic hexaoxazole analogs. When group R' is a carboxylic acid group, treatment with acetic anhydride or similar dehydrating agent will provide the cyclic hydroxyheptaoxazole or its 5-oxazolone tautomer. A substituent can be appended to the hydroxy group using a base such as triethylamine and an alkyl halide or alkyl sulfonate.

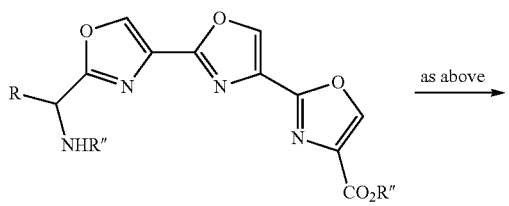

R = CH$_2$OH, iPr, CH$_2$iPr, CH$_2$Ph, CH$_2$CH$_2$CH$_2$CH$_2$NMe$_2$
R' = H, OH
R'' = Boc, Cbz, H

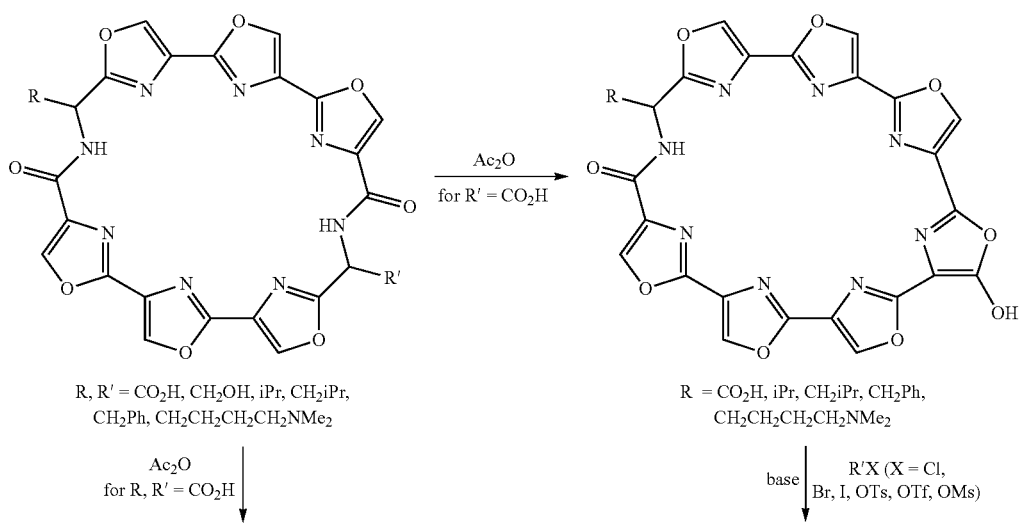

R, R' = CO$_2$H, CH$_2$OH, iPr, CH$_2$iPr, CH$_2$Ph, CH$_2$CH$_2$CH$_2$CH$_2$NMe$_2$

Ac$_2$O for R' = CO$_2$H

R = CO$_2$H, iPr, CH$_2$iPr, CH$_2$Ph, CH$_2$CH$_2$CH$_2$CH$_2$NMe$_2$

Ac$_2$O for R, R' = CO$_2$H base | R'X (X = Cl, Br, I, OTs, OTf, OMs)

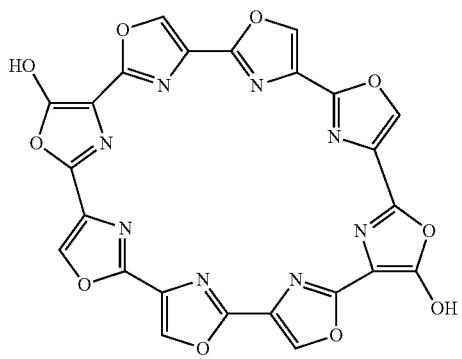

RX or R'X
(X = Cl, Br, I, OTs, OTf, OMs)

| base

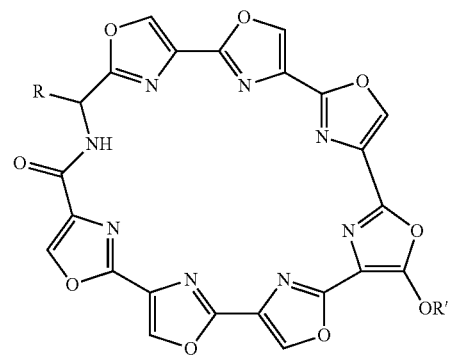

R = CO$_2$OH, iPr, CH$_2$iPr, CH$_2$Ph, CH$_2$CH$_2$CH$_2$CH$_2$NMe$_2$
R' = CH$_2$(CH$_2$)$_n$NMe$_2$
(n = 1, 2, 3), alkyl, H

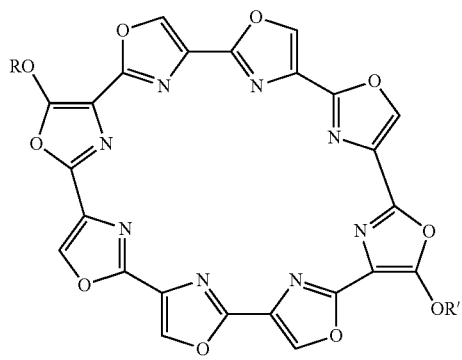

R = CH$_2$(CH$_2$)$_n$NMe$_2$
(n = 1, 2, 3) alkyl, H

B. Hydroxyocta-Oxazoles

Starting from a teroxazole in which group R is a protected carboxyl group, a cyclic hexaoxazole having identical groups R and R' will be prepared using methods described previously. Removal of the protecting groups will lead to the bis(carboxylic acid) derivative which will be treated with acetic anhydride or similar dehydrating agent to give the symmetrical dihydroxyoctaoxazole compound or the bis(5-oxazolone) tautomers. Substituents can be appended to the hydroxy groups using a base such as triethylamine and an alkyl halide or alkyl sulfonate. Unsymmetrical analogs can be prepared starting from teroxazoles having differently protected carboxyl groups. Following the same synthetic pathway the differentially protected dihydroxyoctaoxazole can be prepared. Selective removal of one protecting group followed by attachment of a substituent to the hydroxy group will give the monoderivatized analog. Removal of the second protecting group and attachment of a different substituent will give the unsymmetrical octaoxazole derivative.

Macrocyclic Imido-Polyoxazoles

Starting from a macrocyclic hexaoxazole, prepared as described above, having at least one serine residue (R or R'=CH$_2$OH) treatment with an oxidizing agent such as Dess Martin periodinane (DMP) or iodoxybenzoic acid (IBX) at reflux in a solvent such as methylene chloride, chloroform, benzene, or toluene results in oxidative cleavage to form an imide. If R and R' are both CH$_2$OH similar treatment will form the macrocyclic bis(imide)

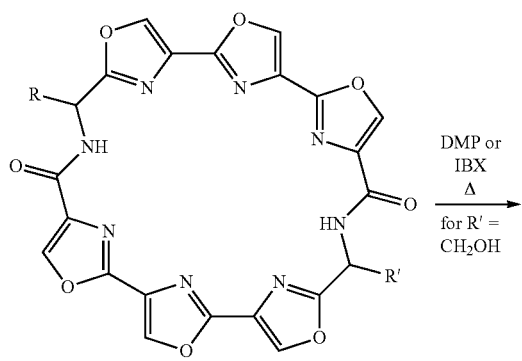

R, R' = CH$_2$OH, iPr, CH$_2$iPr, CH$_2$Ph, CH$_2$CH$_2$CH$_2$CH$_2$NMe$_2$

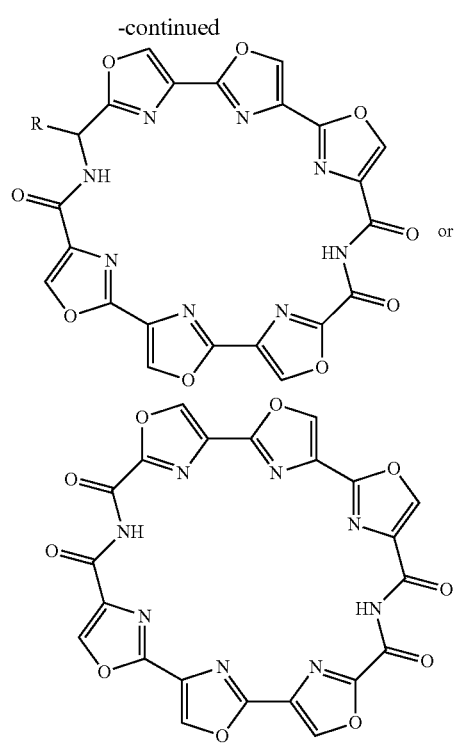

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion.

Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), a vegetable oil, a nontoxic glyceryl ester, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of cancer. Accordingly, in one embodiment the invention also provides a composition comprising a compound of formula I, or a pharmaceutically acceptable salt thereof, at least one other therapeutic agent, and a pharmaceutically acceptable diluent or carrier. The invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal to treat cancer.

The ability of a compound of the invention to stabilize G-quadroplex DNA may be determined using pharmacological models which are well known to the art, or using Test A described below.

Test A. Stabilization of G-Quadruplex DNA

Analyses can be performed to determine the ability of the agents to bind and thermally stabilize the duplex, triplex, and quadruplex forms of nucleic acids. Toward this end, the UV absorbances of the nucleic acids as a function of temperature in the absence and presence of HXDV was monitored. The melting of duplex and triplex nucleic acids is generally associated with a hyperchromic shift at 260 nm (76,77), while the melting of quadruplex nucleic acids is associated with a hypochromic shift at 295 nm (26,78). Thus, the temperature-dependent absorbances of duplexes and triplexes were monitored at 260 nm, with corresponding quadruplex absorbances being monitored at 295 nm. ST DNA, p(rA)·p(rU), p(rA)·p(dT), p(dA)·2p(dT), p(rA)·2p(rU), d(T$_2$AG$_3$)$_4$, and r(UG$_4$U) were used as representative models of a DNA duplex, an RNA duplex, a hybrid DNA·RNA duplex, a DNA triplex, an RNA triplex, a DNA quadruplex, and an RNA quadruplex, respectively. All the UV melting studies were conducted at pH 7.5 in the presence of potassium ions. Representative compounds of Formula I were evaluated and were found to stabalize G-quadroplex DNA.

The ability of compounds (e.g., 219) to stabilize G-quadroplex DNA may also be determined using Test B described below.

Test B. Temperature-Dependent Spectrophotometry

Temperature-dependent absorption experiments were conducted on an AVIV Model 14DS Spectrophotometer (Aviv Biomedical, Lakewood, N.J.) equipped with a thermoelectrically controlled cell holder. Quartz cells with a pathlength of 1.0 cm were used for all the absorbance studies. Temperature-dependent absorption profiles were acquired at either 260 (for duplex and triplex) or 295 (for quadruplex) nm with a 5 sec averaging time. The temperature was raised in 0.5° C. increments, and the samples were allowed to equilibrate for 1.5 mM at each temperature setting. In the quadruplex melting studies, the concentrations of d(T$_2$AG$_3$)$_4$, 9AP, 15AP, and 21AP were 5 µM in strand (120 µM in nucleotide), while the concentration of r(UG$_4$U) was 20 µM in strand (120 µM in nucleotide). When present in these quadruplex studies, compound 219 concentration was 20 µM. In the duplex and triplex melting studies, the nucleic acid concentration was 15 µM in base pair (30 µM in nucleotide) or 15 µM in base triple (45 µM in nucleotide) and the HXDV concentration, when present, was 15 µM. The buffer for all the UV melting experiments contained 10 mM EPPS (pH 7.5). In addition, sufficient KCl was added to each solution to bring the total K$^+$ concentration to either 150 mM for d(T$_2$AG$_3$)$_4$ and p(rA)·p(dT), 2 mM for r(UG$_4$U), 50 mM for ST DNA, 250 mM for p(dA)·2p(dT), or 20 mM for p(rA)·2p(rU). Prior to their use in UV melting experiments, all nucleic acid solutions are preheated at 90° C. for 5 min and slowly cooled to room temperature over a period of 4 hr.

The anti-proliferative activity of a compound of the invention may be determined using pharmacological models which are well known to the art, or using Test C described below.

Test C. Evaluation of G-quadruplex stabilizers using the MTT Assay.

Cell lines were selected based upon one or more factors including data on their relative telomerase activity, varied organ sites, available comparative data, and their ability to form solid tumors in athymic nude mice. The advantage of an MTT assay is that the cytotoxic/cytostatic activities can be readily determined. Cells were cultured for 4 days at 37° C. followed by addition of MTT (3-[4,5-dimethylthiozol-2-yl]-2,5-diphenyltetrazolium bromide (Sigma) (0.1 mg/ml). Cells were treated with MTT for 3 hrs and then dissolved in 100 µl 100% DMSO. Absorbance was measured at OD$_{570}$ using a microplate reader (Model 3550 UV from BIO-RAD). The MTT value was normalized to OD$_{570}$ of cells treated with Cellfectin alone. Stock solutions of each compound were prepared. MTT assays were performed using spectrometric analysis and 96 well plates. Representative compounds of Formula I were evaluated and were found to demonstrate anti-proliferative activity in Test C.

The invention will now be illustrated by the following non-limiting Examples.

EXAMPLES

Example 1

Synthesis of Compound 15

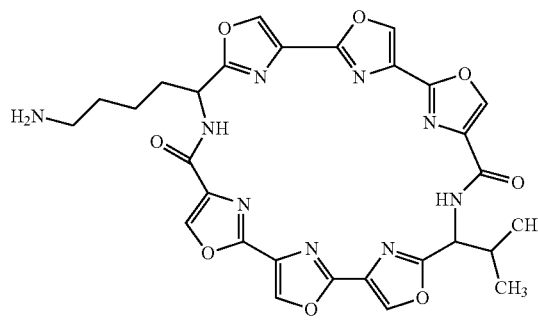

A representative compound of the invention (Compound 15) was prepared as illustrated and described below.

a. Synthesis of Compound 1 (NBoc-Cbz Lysine)

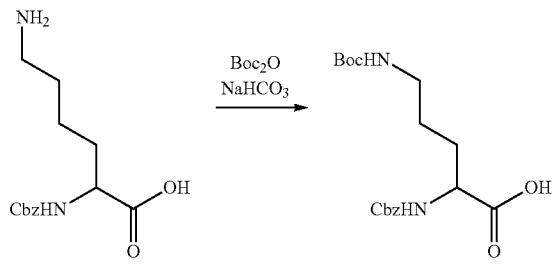

N-α-Cbz-(S)-Lysine (5 g, 17.85 mmol) was dissolved in a mixture of THF (50 mL) and water (50 mL). To this sodium bicarbonate (3 g, 35.5 mmol, 2 eq) and a solution of Boc$_2$O (9 g, 41 mmol, 2.3 eq) in THF (50 mL). After stirring at room temperature overnight, the THF was removed under reduced pressure and the resulting aqueous solution was neutralized with 2N HCl. This was extracted with ethyl acetate and the combined organic layers were washed with brine. The organic layer was dried with sodium sulfate and concentrated to a clear oil. Removal of excess Boc$_2$O by Kugelrhor distillation resulted in a thick clear oil weighing 6.8 g, 100%. $^1$H NMR (CDCl$_3$) δ 11.6 (s, 1H), 7.32 (s, 5H), 6.36 (s, 1H), 5.75 (d, 1H, J=8), 5.09 (s, 2H), 4.37 (m, 1H), 3.06 (m, 2H), 1.78 (m, 2H), 1.53 (s, 4H), 1.42 (s, 9H). $^{13}$C NMR (CDCl$_3$) δ 174.8, 155.4, 135.4, 127.6, 127.3, 127.2, 78.6, 66.1, 52.9, 39.2, 31.0, 28.6, 27.5, 26.6, 21.4 b. Synthesis of Compound 2

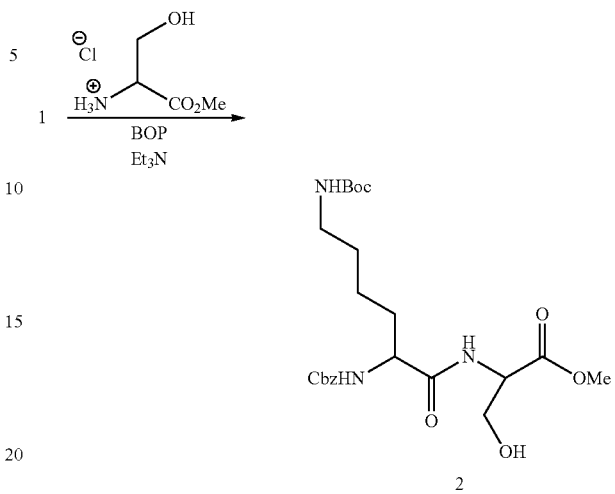

(DL)-serine methyl ester hydrochloride (2.78 g, 17.85 mmol 1 eq), BOP (7.9 g, 17.85 mmol, 1 eq) and 1 (6.8 g, 17.85 mmol) were dissolved in dry CH$_3$CN (100 mL). To this triethylamine (6.2 mL, 44.6 mmol, 2.5 eq) was added and the reaction stirred at room temperature overnight. The solvent was then removed in vacuo and the residue was taken up in ethyl acetate. This was washed successively with brine, 2N HCl, 0.5 N NaHCO$_3$, water and brine. The organic layer was dried with sodium sulfate and concentrated to a clear oil weighing 8.6 g, 100%. $^1$H NMR (CDCl$_3$) δ 7.50 (m, 1H), 7.31 (s, 5H), 6.12 (m, 1H), 5.06 (m, 3H), 4.63 (m, 1H), 4.30 (m, 1H), 3.94 (m, 2H), 3.71 (s, 3H), 3.07 (m, 2H), 1.63 (m, 2H), 1.43 (m, 11H). $^{13}$C NMR (CDCl$_3$) δ 171.6, 170.3, 170.0, 155.7, 135.3, 127.6, 127.2, 127.1, 78.3, 66.1, 61.6, 53.8, 51.7, 51.7, 39.0, 31.4, 31.2, 28.5, 27.5, 21.5. IR (thin film, NaCl) 3336, 3068, 3014, 2981, 2937, 2866, 1693, 1525, 1455, 1392, 1366, 1250, 1170, 1061, 912, 849, 755, 698, 666 cm$^{-1}$ c. Synthesis of Compound 3 (Lysine Oxazoline)

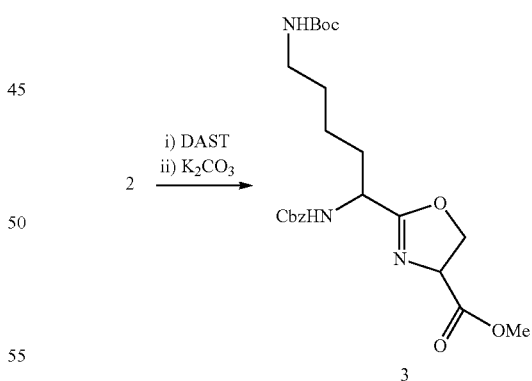

Compound 2 (8.6 g, 17.85 mmol) was dissolved in dry CH$_2$Cl$_2$ (40 mL) and placed under argon. After cooling to −78° C., DAST (3.5 mL, 26.8 mmol, 1.5 eq) was added. After stirring at low temperature for 4 hours, solid K$_2$CO$_3$ (3.7 g, 26.8 mmol, 1.5 eq) was added and the reaction warmed to room temperature. The reaction mixture was poured into saturated NaHCO$_3$ and the layers were separated. The aqueous layer was further extracted with CH$_2$Cl$_2$ and the combined organic layers were dried with sodium sulfate. Removal of solvent under reduced pressure afforded the oxazoline as an orange oil weighing 8.3 g, 99%. $^1$H NMR (CDCl$_3$) 7.34 (s, 5H), 5.67 (t, 1H, J=9), 5.10 (s, 2H), 4.73 (m, 2H) 4.46 (m, 3H), 3.77 (s, 3H), 3.00 (m, 2H), 1.75 (m, 2H), 1.42 (s, 13H). $^{13}$C NMR (CDCl$_3$) δ 170.4, 170.3, 169.2, 168.8, 155.2, 154.9, 135.4, 127.6, 127.2, 78.1, 69.4, 69.2, 66.9, 66.8, 66.0, 51.8, 48.2, 39.3, 31.9, 31.8, 28.6, 27.5, 21.3, 21.1. IR (thin film, NaCl) 3349, 3069, 3034, 2981, 2953, 2866, 2249, 1705, 1666, 1519, 1455, 1439, 1392, 1366, 1337, 1249, 1174, 1060, 988, 912, 848, 777, 733, 698, 647 cm$^{-1}$ d. Synthesis of Compound 4 (Lysine Oxazole)

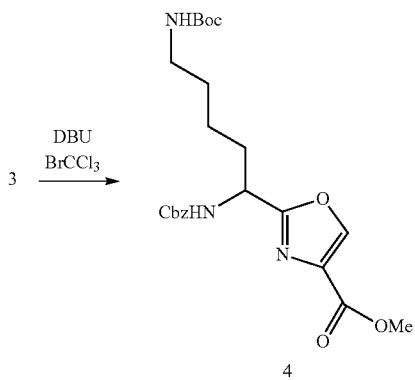 [SMILES: COC(=O)c1coc(C(CCCCNC(=O)OC(C)(C)C)NC(=O)OCc2ccccc2)n1]

Compound 3 (8.3 g, 17.85 mmol) was dissolved in dry CH$_2$Cl$_2$ (40 mL) and placed under argon. This was cooled to 0° C. and treated dropwise with DBU (5.3 mL, 35.7 mmol, 2 eq) and BrCCl$_3$ (4.2 mL, 42.8 mmol, 2.4 eq) successively. The reaction mixture turned from orange to dark brown in color and was allowed to warm to room temperature overnight. It was then poured into a solution of saturated ammonium chloride and extracted with CH$_2$Cl$_2$. The organic layers were dried with sodium sulfate and concentrated to a brown oil. This was flash chromatographed on SiO$_2$ with 1-5% methanol/chloroform which gave the product as an amber oil weighing 7.0 g, 85%. $^1$H NMR (CDCl$_3$) δ 8.18 (s, 1H), 7.31 (m, 6H), 5.71 (d, 1H, J=8), 5.10 (s, 2H), 5.00 (m, 1H), 4.61 (M, 1H), 3.90 (s, 3H), 3.08 (m, 2H), 1.90 (m, 2H), 1.41 (m, 12H). $^{13}$C NMR (CDCl$_3$) δ 164.1, 160.5, 155.2, 154.9, 143.1, 135.3, 132.4, 127.6, 127.3, 127.2, 78.3, 76.4, 66.3, 51.3, 48.5, 39.1, 32.7, 28.6, 27.5, 21.5 IR (thin film, NaCl) 3337, 3167, 3069, 3034, 2975, 2952, 2866, 2250, 1705, 1585, 1523, 1455, 1439, 1392, 1366, 1325, 1249, 1170, 1111, 1044, 1002, 912, 863, 805, 733, 698, 647 cm$^{-1}$ e. Synthesis of Compound 5 (Lysine Oxazole Acid)

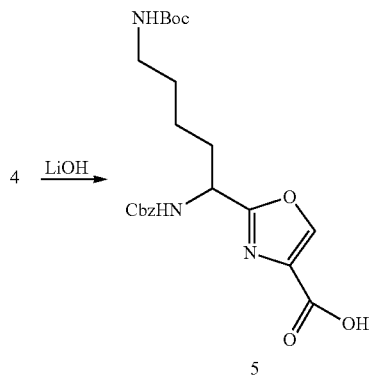 [SMILES: "LiOH" ; CC(C)(C)OC(=O)NCCCCC(NC(=O)OCc1ccccc1)c1nc(C(=O)O)co1]

Compound 4 (7.0 g, 15.23 mmol) was dissolved in a 3:1 mixture of THF and water (40 mL) and cooled to 0° C. To this LiOH (767 mg, 18.3 mmol, 1.2 eq) was added and the reaction warmed to room temperature overnight. After removing the solvent under vacuum, 1N HCl (22 mL) was added until the pH was slightly acidic. This was extracted with ethyl acetate and the combined organic layers were washed with brine. After drying with sodium sulfate, the organic phase was concentrated to a pale yellow, sticky solid weighing 5.9 g, 87%. Melting point 65-67° C. $^1$H NMR (CDCl$_3$) δ 12.39 (s, 1H), 8.17 (s, 1H), 7.25 (m, 6H), 6.52 (m, 1H), 5.08 (m, 3H), 4.69 (m, 1H), 3.09 (m, 2H), 1.92 (m, 2H), 1.42 (s, 12H). $^{13}$C NMR (CDCl$_3$) δ 165.1, 162.7, 155.3, 143.7, 135.3, 132.5, 128.2, 127.6, 127.3, 127.2, 124.4, 78.5, 66.2, 48.5, 39.1, 32.7, 28.5, 27.5, 21.6. IR (thin film, NaCl) 3321, 2934, 2551, 2250, 1701, 1527, 1455, 1367, 1251, 1164, 1111, 1045, 982, 911, 860, 732, 697, 947 cm$^{-1}$. HRMS (FAB) m/z calcd for C$_{22}$H$_{29}$N$_3$O$_7$Li (M+Li) 455.2194; found, 455.2179 f. Synthesis of Compound 6 (TIPS Bisoxazole)

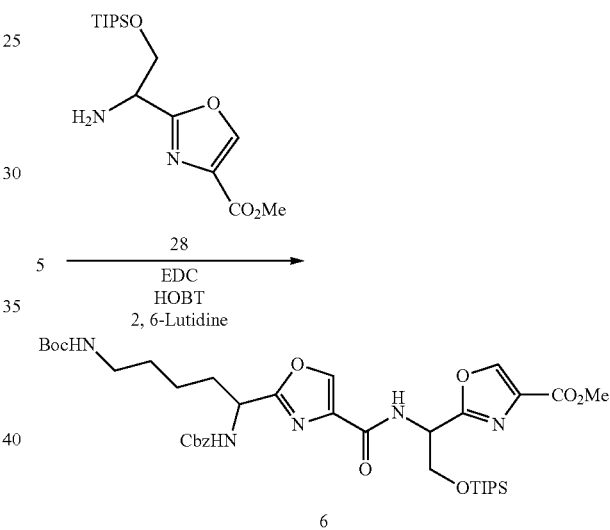

The TIPS oxazole 28 (3.58 g, 10.47 mmol) was dissolved in dry CH$_2$Cl$_2$ (20 mL) and placed under argon. To this was added freshly distilled 2,6-lutidine (6.1 mL, 52.4 mmol, 5 eq) and the flask was cooled to 0° C. Then a solution of 5 (4.68 g, 10.47 mmol, 1 eq), EDC (4.02 g, 20.94 mmol, 1.2 eq) and HOBT (2.83 g, 20.94 mmol, 1.2 eq) in CH$_2$Cl$_2$ (40 mL) was added. The reaction warmed to room temperature overnight and then the solvent was removed under reduced pressure. The residue was taken up in ethyl acetate and washed successively with saturated NaHCO$_3$, 5% HCl, water and brine. The organic phase was dried over sodium sulfate and concentrated to an orange oil weighing 7.04 g, 87%. $^1$H NMR (CDCl$_3$) δ 8.20 (s, 1H), 8.10 (s, 1H), 7.39 (d, 1H, J=8), 7.35 (s, 6H), 5.66 (d, 1H, J=8), 5.46 (dt, 1H, J=5, 8), 5.11 (s, 2H), 4.97 (dt, 1H J=7, 7), 4.67 (dd, 1H J=4, 10), 4.20 (m, 3l1), 3.79 (s, 3H), 3.90 (m, 2H), 1.90 (m, 2H), 1.42 (m, 11H), 1.02 (m, 21H) $^{13}$C NMR (CDCl$_3$) δ 163.0, 162.5, 160.6, 159.2, 155.2, 154.9, 143.2, 140.6, 135.3, 134.7, 132.6, 127.6, 127.3, 127.3, 97.4, 78.5, 66.3, 63.9, 51.2, 48.4, 39.2, 32.5, 28.7, 27.5, 21.5, 17.2, 16.9, 12.1, 11.5, 10.9. IR (thin film, NaCl) 3295, 3034, 2944, 2866, 2250, 1712, 1599, 1520, 1461, 1391, 1366, 1324, 1249, 1204, 1171, 1115, 1045, 998, 912, 883, 843, 803, 733, 684, 647 cm$^{-1}$. HRMS (FAB) m/z calcd for C$_{38}$H$_{57}$N$_5$O$_{10}$SiLi (M+Li) 778.4029; found 778.4053 g. Synthesis of Compound 7 (Lysine Bisoxazole)

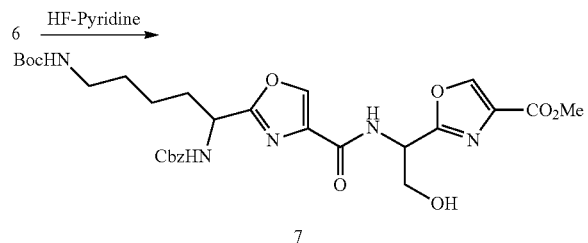

Compound 6 (7.2 g, 9.3 mmol) was dissolved in THF (50 mL) and pyridine (10 mL). This was treated dropwise with HF-pyridine complex (3 mL) during which a gas was evolved. The reaction stirred at room temperature for 18 hours and then slowly poured into saturated NaHCO$_3$. This was extracted with chloroform and dried with sodium sulfate. After concentrating and azeotroping with toluene, the product was obtained as an orange oil weighing 5.76 g, 100%. $^1$H NMR (CDCl$_3$) δ 9.09 (d, 1H, J=7), 8.26 (s, 1H), 8.21 (s, 1H), 7.30 (m, 6H), 6.63 (d, 1H, J=9), 5.46 (m, 1H), 5.08 (s, 2H), 4.68 (m, 2H), 4.26 (m, 2H), 3.86 (s, 3H), 3.07 (m, 2H), 1.43 (s, 12H). $^{13}$C NMR (CDCl$_3$) δ 162.9, 162.8, 160.8, 155.2, 143.4, 143.2, 135.4, 134.4, 132.1, 128.2, 127.7, 127.3, 127.2, 124.4, 78.3, 66.2, 63.8, 61.9, 51.5, 51.3, 49.4, 47.5, 39.3, 32.2, 31.2, 28.5, 27.5, 21.7. IR (thin film, NaCl) 3307, 3034, 2945, 2867, 2250, 1712, 1599, 1519, 1456, 1392, 1367, 1324, 1249, 1170, 1113, 1001, 911, 863, 805, 732, 697, 647 cm$^{-1}$ h. Synthesis of Compound 8

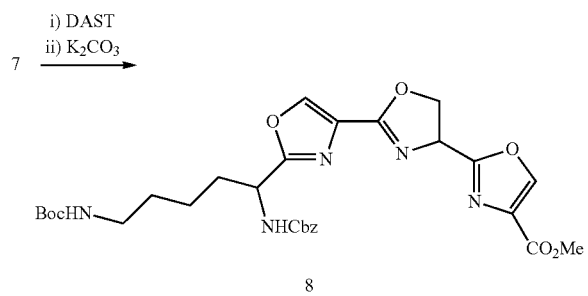

Compound 7 (2.76 g, 9.3 mmol) was dissolved in dry CH$_2$Cl$_2$ (40 mL) and placed under argon. After cooling to −78° C., DAST (1.8 mL, 13.95 mmol, 1.5 eq) was added and the reaction stirred at low temperature for 4 hours. This was followed by addition of solid K$_2$CO$_3$ (1.9 g, 13.95 mmol, 1.5 eq) and the mixture warmed to room temperature. The solution was poured into saturated NaHCO$_3$ and extracted with CH$_2$Cl$_2$. The combined organic layers were dried with sodium sulfate and concentrated to afford an orange oil weighing 5.58 g, 100%. $^1$H NMR (CDCl$_3$) δ 8.25 (s, 1H), 8.20 (s, 1H), 8.11 (d, 1H, J=3), 7.91 (d, 1H, J=10), 7.33 (s, 5H), 5.71 (d, 1H, J=9), 5.53 (m, 1H), 5.10 (s, 2H), 4.87 (m, 2H), 4.62 (m, 1H), 3.91 (s, 3H), 3.07 (m, 2H), 1.85 (m, 2H), 1.41 (s, 14H). $^{13}$C NMR (CDCl$_3$) δ 164.5, 163.0, 162.5, 162.1, 160.4, 159.3, 155.2, 144.0, 143.2, 140.9, 135.3, 134.7, 132.4, 129.1, 127.6, 127.3, 127.2, 78.3, 69.8, 66.2, 63.8, 62.8, 51.3, 48.4, 39.2, 35.5, 32.9, 28.7, 27.5, 21.5, 12.8. IR (thin film, NaCl) 3323, 3155, 3034, 2944, 2867, 2248, 1713, 1584, 1522, 1456, 1391, 1366, 1322, 1249, 1171, 1111, 1044, 995, 914, 885, 804, 775, 733, 698, 646 cm$^{-1}$.

i. Synthesis of Compound 9 (Lysine Teroxazole)

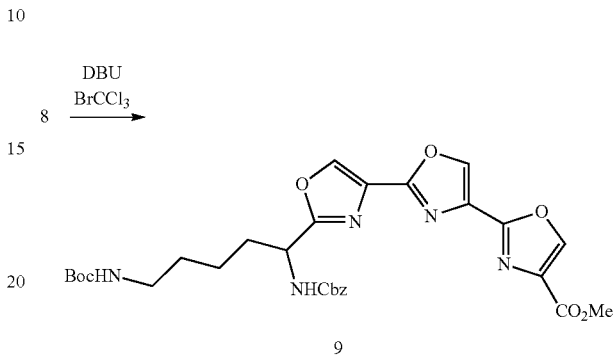

Compound 8 (5.58 g, 9.3 mmol) was dissolved in dry CH$_2$Cl$_2$ (40 mL) and placed under argon. The flask was cooled to 0° C. and DBU (2.8 mL, 18.6 mmol, 2 eq) and BrCCl$_3$ (2.2 mL, 22.3 mmol, 2.4 eq) were both added dropwise. This warmed to room temperature overnight and was then poured into saturated ammonium chloride solution. The layers were separated and the aqueous extracted with CH$_2$Cl$_2$. The combined organic layers were dried with sodium sulfate and concentrated to a brown oil. Flash chromatography on SiO$_2$ with 1-2% methanol/chloroform afforded a thick yellow oil. The product obtained from the column was recrystallized from benzene to give white sand like crystals weighing 2.52 g, 46%. Melting point 135-137° C.; Optical rotation [α]$_D^{22}$=−37° (c=1 g/100 mL in CHCl$_3$). $^1$H NMR (CDCl$_3$) δ 8.44 (s, 1H), 8.34 (s, 1H), 8.31 (s, 1H), 7.35 (m, 5H), 5.68 (d, 1H, J=8), 5.12 (s, 2H), 5.04 (m, 1H), 4.61 (m, 1H), 3.95 (s, 3H), 3.10 (m, 2H), 1.98 (m, 2H), 1.41 (s, 14H) $^{13}$C NMR (CDCl$_3$) δ 164.7, 160.4, 155.2, 155.1, 155.0, 154.5, 143.4, 143.0, 139.8, 138.7, 138.5, 135.2, 133.6, 130.0, 128.9, 127.6, 127.4, 127.3, 127.3, 78.3, 66.3, 57.6, 51.4, 48.6, 39.1, 32.7, 28.7, 27.5, 21.5. IR (nujol) 3325, 3156, 3117, 1721, 1689, 1644, 1578, 1518, 1377, 1327, 1247, 1116, 999, 976, 816, 805, 775, 725 cm$^{-1}$ HRMS (FAB) m/z calcd for C$_{29}$H$_{33}$N$_5$O$_9$Li (M+Li) 602.2433; found 602.2436 j. Synthesis of Compound 10 (Lysine Teroxazole Acid)

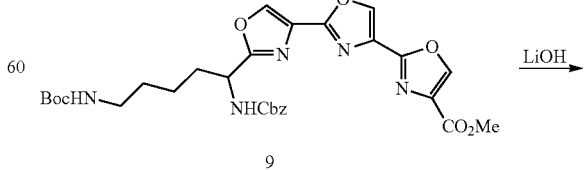

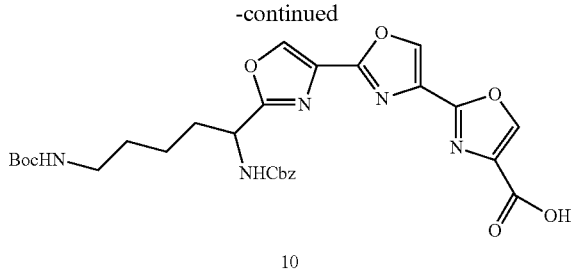

10

Compound 9 (1.9 g, 3.2 mmol) was dissolved in a 3:1 mixture of THF and water (60 mL) and cooled to 0° C. Then LiOH (161 mg, 3.83 mmol, 1.2 eq) was added and the reaction warmed to room temperature overnight. The solvent was removed under vacuum and the residue was taken up in water. The pH was acidified with 1N HCl (15 mL) and a white solid precipitated. The precipitate was filtered and the filtrate was extracted with ethyl acetate. The organic phase was washed with brine and dried with sodium sulfate. The solvent was removed to give a white solid weighing 1.90 g, 100%. Melting point 164-166° C. $^1$H NMR (DMSO) δ 9.14 (s, 1H), 9.11 (s, 1H), 8.45 (s, 1H), 8.28 (d, 1H, J=8), 7.56 (s, 5H), 6.99 (m, 1H), 5.25 (s, 2H), 4.96 (m, 1H), 3.08 (m, 2H), 2.06 (m, 2H), 1.55 (s, 14H). $^{13}$C NMR (DMSO) δ 165.5, 155.9, 155.4, 140.6, 140.4, 139.8, 136.8, 128.8, 128.3, 128.1, 127.7, 125.2, 77.3, 65.6, 49.0, 31.8, 29.0, 28.2, 22.5, 21.0, 17.6. IR (nujol) 3337, 2367, 2334, 1681, 1523, 1381, 1364, 1255, 1167, 1109 cm$^{-1}$ k. Synthesis of Compound 11 (Protected Linear Hexaoxazole Lysine-Valine)

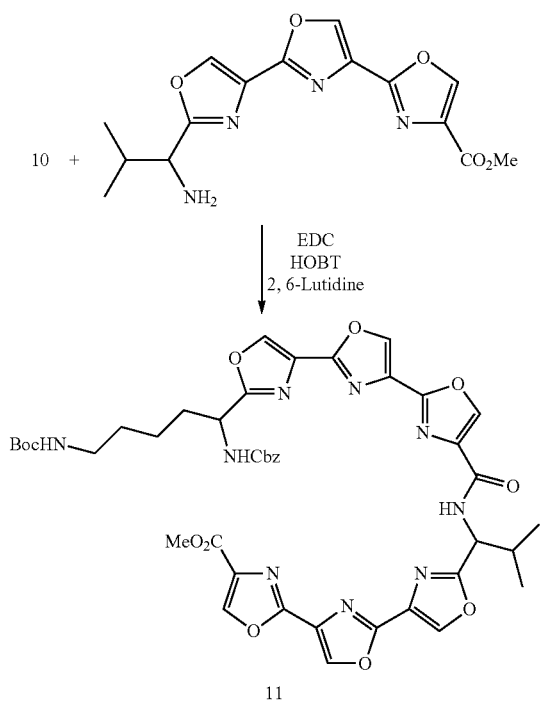

11

The valine teroxazole (200 mg, 0.6 mmol), lysine teroxazole 10 (350 mg, 0.6 mmol), EDC (230 mg, 1.2 mmol, 2 eq), HOBT (162 mg, 1.2 mmol, 2 eq) and 2,6-lutidine (0.1 mL, 0.6 mmol, 10 eq) were dissolved in dry DMF (100 mL) and placed under argon. The reaction stirred at room temperature overnight. The solvent was then removed under vacuum and the resulting residue was dissolved in ethyl acetate. This was washed successively with saturated NaHCO$_3$, 5% HCl, water and brine. The organic phase was dried with sodium sulfate and concentrated to give an orange solid weighing 456 mg, 85%. Melting point 240-243° C.; Optical rotation $[\alpha]_D^{23}$=+14.9° (c=1 g/100 mL in CHCl$_3$). $^1$H NMR (CDCl$_3$) δ 8.44 (s, 1H), 8.33 (m, 5H), 7.61 (d, 1H, J=10), 7.35 (s, 5H), 5.65 (d, 1H, J=8), 5.36 (m, 1H), 5.13 (s, 2H), 5.05 (m, 1H), 4.60 (m, 1H), 3.95 (s, 3H), 3.11 (m, 2H), 2.43 (m, 1H), 2.01 (m, 2H), 1.42 (s, 13H), 1.09 (d, 3H, J=7), 1.02 (d, 3H, J=7). $^{13}$C NMR (CDCl$_3$) δ 164.7, 163.8, 160.4, 159.0, 155.2, 143.0, 140.8, 138.7, 138.6, 138.5, 138.3, 136.0, 133.6, 130.1, 130.0, 129.0, 128.9, 127.6, 127.3, 127.3, 78.3, 66.3, 51.6, 51.4, 48.6, 39.1, 32.8, 31.9, 28.7, 27.5, 21.5, 18.1, 17.6. IR (nujol) 3392, 3367, 3148, 1720, 1683, 1649, 1594, 1571, 1519, 1377, 1310, 1284, 1247, 1171, 1114, 1000, 914, 874, 808, 775, 723, 696 cm$^{-1}$. HRMS (FAB) m/z calcd for C$_{43}$H$_{45}$N$_9$O$_{13}$Li (M+Li) 902.3291; found, 902.3264.

l. Synthesis of Compound 12 (Linear Hexaoxazole Amine Lysine-Valine)

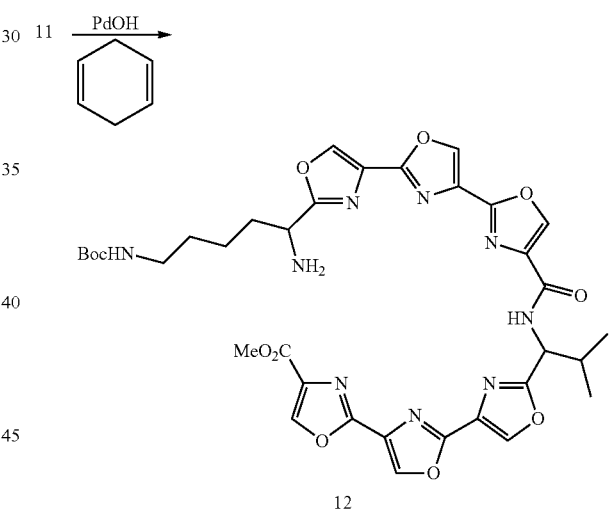

12

Compound 11 (450 mg, 0.5 mmol) was dissolved in a 10% mixture of ethanol in THF (75 mL) and refluxed with 20% PdOH on carbon (150 mg) and 1,4-cyclohexadiene (2 mL) for 3 days. The reaction was cooled to room temperature and filtered through Celite, washing with 10% methanol/CH$_2$Cl$_2$ (200 mL). This was concentrated to a cream colored solid weighing 380 mg, 100%.

Melting point 157-160° C. $^1$H NMR (CDCl$_3$) δ 8.45 (s, 1H), 8.33 (m, 5H), 7.65 (d, 1H, J=10), 5.36 (m, 1H), 5.03 (m, 1H), 4.65 (m, 1H), 9.95 (s, 3H), 3.11 (m, 2H), 2.43 (m, 1H), 2.01 (m, 2H), 1.43 (s, 13H), 1.09 (d, 3H, J=7), 1.03 (d, 3H, J=6) $^{13}$C NMR (CDCl$_3$) δ 163.8, 160.4, 159.0, 155.2, 150.6, 143.0, 140.8, 138.6, 138.5, 136.0, 135.0, 133.6, 130.0, 129.0, 127.4, 124.6, 78.2, 51.6, 51.4, 39.5, 33.3, 31.9, 29.4, 27.5, 20.3, 18.1, 17.6. IR (nujol) 3647, 3356, 3178, 3144, 3118, 1721, 1657, 1600, 1571, 1518, 1377, 1364, 1282, 1167, 1113, 999, 973, 914, 860, 775, 724 cm$^{-1}$ m. Synthesis of Compound 13 (Liner Hexaoxazole De-Esterified Lysine-Valine)

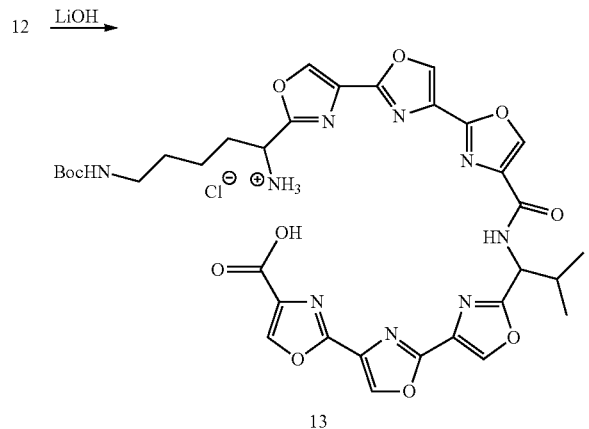

13

Compound 12 (380 mg, 0.5 mmol) was dissolved in a 3:1 mixture of THF and water (28 mL) and cooled to 0° C. Then LiOH (25 mg, 0.6 mmol, 1.2 eq) was added and the reaction warmed to room temperature overnight. The solvent was removed and the residue was dissolved in water. The pH was acidified with 1N HCl and a white solid precipitated. This was filtered and the filtrate was concentrated. After azeotroping the aqueous layer and triturating with ethanol, the product was obtained as a white solid weighing 378 mg, 100%. Melting point 265° C.

$^1$H NMR (DMSO) δ 9.02 (m, 3H), 8.88 (m, 3H), 6.76 (m, 1H), 5.06 (m, 1H), 4.33 (m, 1H), 2.87 (m, 2H), 1.86 (m, 2H), 1.33 (s, 13H), 1.02 (d, 3H, J=7), 0.92 (d, 3H, J=7). $^{13}$C NMR (CDCl$_3$+CD$_3$OD) 163.8, 142.8, 128.1, 127.3, 124.5, 124.3, 33.3, 29.4, 28.4, 27.2, 23.4, 20.1. IR (nujol) 3359, 3178, 3142, 1688, 1658, 1519, 1377, 1281, 1170, 1115, 974, 915, 725 cm$^{-1}$ n. Synthesis of Compound 14 (Boc Protected Cyclic Hexaoxazole Lysine-Valine)

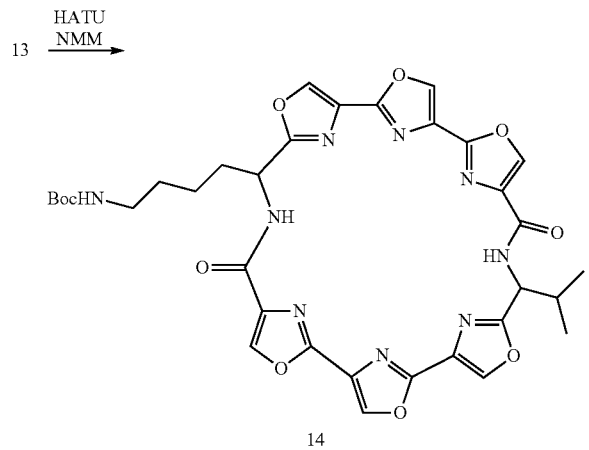

14

Compound 13 (20 mg, 0.0255 mmol) was dissolved in a mixture of dry DMF (10 mL) and dry CH$_2$Cl$_2$ (20 mL) and placed under argon. The flask was cooled to 0° C. and N-methylmorpholine (6 μL, 0.056 mmol, 2.2 eq) and a solution of HATU (12 mg, 0.031 mmol, 1.2 eq) in DMF (1 mL) were added. This stirred at 0° C. for 4 hours then warmed to room temperature overnight. The solvent was removed under reduced pressure and the residue was chromatographed with 1% methanol/chloroform on SiO$_2$ which afforded 10 mg of product as a white solid, 54%. Melting point 207-210° C. Optical rotation [α]$_D^{24}$=−22.8° (c=0.25 g/100 mL in CHCl$_3$). $^1$H NMR (CDCl$_3$) δ 8.56 (d, 1H, J=8), 8.84 (d, 1H, J=8), 8.22 (m, 6H), 5.42 (dt, 1H J=6, 8), 5.33 (dd, 1H, J=5, 8) 4.57 (m, 1H), 3.08 (m, 2H), 2.38 (m, 1H), 2.04 (m, 2H), 1.46 (m, 13H), 1.06 (d, 3H, J=7), 0.98 (d, 3H, J=7)

$^{13}$C NMR (CDCl$_3$) δ 164.0, 163.6, 159.0, 155.1, 153.9, 140.0, 138.2, 138.0, 137.4, 136.3, 130.2, 128.9, 52.2, 47.0, 44.8, 39.8, 33.9, 33.1, 28.7, 27.5, 21.2, 17.6, 17.3 IR(thin film, NaCl) 3380, 3146, 2966, 2937, 2866, 1678, 1594, 1509, 1366, 1249, 1169, 1106, 972, 916, 723 cm$^{-1}$. HRMS (FAB) m/z calcd for C$_{34}$H$_{35}$N$_9$O$_{10}$Li (M+Li) 736.2662; found, 736.2665 o. Synthesis of Compound 15 (Cyclic Lysine-Valine Amine TFA Salt)

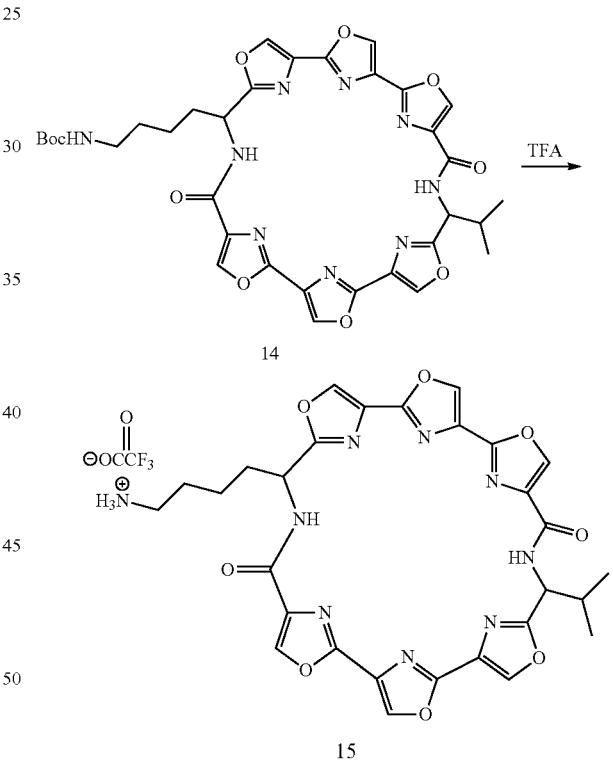

Compound 14 (21 mg, 0.029 mmol) was dissolved in CH$_2$Cl$_2$ (2 mL) and cooled to 0° C. Then TFA (2 mL) was added and this stirred at low temperature for 1.5 hours. The solvent was then removed in vacuo and the residue was azeotroped with benzene twice. The residue was then taken up in chloroform and 1 drop of methanol and the product was precipitated by adding hexane. After removal of the organic solvent via pipette, the product was obtained as a white solid weighing 21 mg, 100%. Melting point 297-300° C.; Optical rotation [α]$_D^{24}$=−20.6 (c=0.18 g/100 mL in 10% MeOH/CHCl$_3$). $^1$H NMR (CDCl$_3$) δ 8.31 (m, 8H), 5.37 (m, 2H), 2.44 (m, 1H), 1.93 (m, 2H), 1.29 (m, 2H), 0.98 (m, 8H)

$^{13}$C NMR (CDCl$_3$+CD$_3$OD) δ 164.9, 164.0, 159.3, 155.6, 153.8, 140.4, 139.8, 139.2, 138.5, 138.3, 136.0, 135.6, 129.5, 128.2, 128.1, 63.0 52.6, 39.3, 32.5, 32.0, 26.2, 20.1, 17.5, 17.3. IR (thin film, NaCl) 3389, 2360, 2340, 1666, 1589, 1458, 1104 cm$^{-1}$. HRMS (FAB) m/z calcd for C$_{29}$H$_{27}$N$_9$O$_8$Li (free base) (M+Li) 636.2137; found, 636.2139

The intermediate Compound 28 used in step f above was prepared as follows.

p. Synthesis of Compound 23

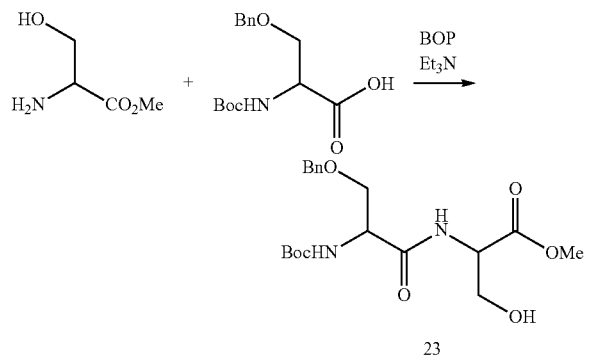

Boc-O-benzyl-L-serine (4.13 g, 14 mmol), serine methyl ester (2.18 g, 14 mmol) and BOP (6.19 g, 14 mmol) were dissolved in CH$_3$CN (40 mL). Then triethylamine (4.2 mL, 30.8 mmol, 2.2 eq) was added. The reaction stirred overnight at room temperature. The solvent was removed and the residue was dissolved in CH$_2$Cl$_2$ and washed successively with brine, 2N HCl, 0.5 N NaHCO$_3$, water and brine. The organic extract was dried over Na$_2$SO$_4$ and concentrated to a clear oil weighing 5.54 g, 100%. $^1$H NMR (CDCl$_3$) δ 7.31 (s, 6H), 5.49 (d, 1H, J=6), 4.64 (m, 1H), 4.55 (s, 2H), 4.31 (m, 1H), 3.88 (dd, 1H J=5, 10), 3.75 (s, 3H), 3.63 (dd, 1H J=6, 10), 2.96 (br s, 1H), 1.44 (s, 9H). $^{13}$C NMR (CDCl$_3$) δ 170.5, 170.3, 155.5, 137.2, 128.3, 127.8, 127.8, 127.7, 80.5, 73.3, 69.8, 69.4, 62.6, 62.4, 60.3, 54.8, 52.5, 28.1. IR (thin film NaCl) 3419, 3065, 3032, 2979, 2954, 2871, 2251, 1670, 1498, 1455, 1439, 1392, 1368, 1248, 1167, 1105, 1027 cm$^{-1}$. HRMS (FAB) m/z calcd for C$_{19}$H$_{28}$N$_2$O$_7$Li (M+Li) 403.2057; found, 403.2052.

q. Synthesis of Compound 24 (Serine Oxazoline)

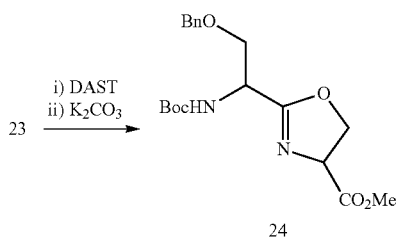 [SMILES: COC(=O)C1COC(C(COCc2ccccc2)NC(=O)OC(C)(C)C)=N1]

Compound 23 (5.54 g, 14 mmol) was dissolved in CH$_2$Cl$_2$ (20 mL) and placed under argon. After cooling to −78° C., DAST (2.8 mL 21.4 mmol, 1.5 eq) was added and the reaction stirred at low temperature for 2.5 hours. Then K$_2$CO$_3$ 2.9 g, 21.4 mmol, 1.5 eq) was added and the reaction warmed to room temperature. This was poured into saturated NaHCO$_3$. The layers were separated and the aqueous was extracted with CH$_2$Cl$_2$. The organic extracts were dried over Na$_2$SO$_4$ and concentrated to an orange oil weighing 5.28 g, 99%. $^1$H NMR (CDCl$_3$) δ 7.50 (m, 5H), 5.66 (m, 1H), 4.99 (dd, 1H, J=8, 10), 4.71 (m, 5H), 3.96 (m, 5H), 1.64 (s, 9H). $^{13}$C NMR (CDCl$_3$) δ 170.2, 167.4, 154.3, 136.9, 134.2, 127.5, 126.8, 126.6, 79.0, 72.2, 69.2, 69.0, 67.2, 67.1, 52.5, 51.7, 48.5, 24.7. IR (neat NaCl) 3384, 3063, 3030, 2977, 2870, 1709, 1666, 1506, 1454, 1367, 1322, 1166, 1109, 1051 cm$^{-1}$ r. Synthesis of Compound 25 (Boc-O-Benzyl Serine Oxazole)

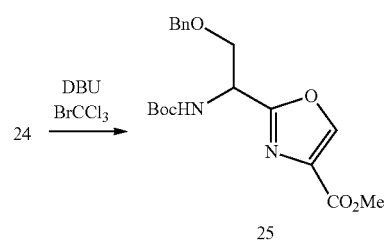 [SMILES: COC(=O)c1coc(C(COCc2ccccc2)NC(=O)OC(C)(C)C)n1]

Oxazoline 24 (5.28 g, 14 mmol) in CH$_2$Cl$_2$ (20 mL) was placed under argon and cooled to 0° C. DBU (3.2 mL, 2 mmol, 1.6 eq) was added dropwise and the solution turned yellow. Then BrCCl$_3$ (2.2 mL, 22.4 mmol) was added dropwise and the solution became brown. This warmed to room temperature overnight and then poured into saturated ammonium chloride. The aqueous layer was extracted with CH$_2$Cl$_2$. The organic layers were dried over Na$_2$SO$_4$ and concentrated to a brown oil. This was flash chromatographed on SiO$_2$ with 15-50% EtOAc/hexane. The product was obtained as a clear oil 3.10 g, 59%. [α]$^{25}$$_D$ −33.35 (c=2 g/100 mL in EtOH). $^1$H NMR (CDCl$_3$) δ 8.36 (s, 1H) 7.41 (m, 5H), 5.76 (d, 1H, J=8), 5.30 (m, 1H), 4.66 (s, 2H), 4.07 (m, 3H), 3.97 (m, 2H), 1.61 (s, 9H). $^{13}$C NMR (CDCl$_3$) δ 163.4, 161.3, 154.9, 144.0, 137.2, 133.3, 128.2, 127.7, 127.4, 80.1, 73.1, 70.3, 52.0, 49.2, 28.1. IR (thin film NaCl) 3351, 3163, 3064, 3031, 2978, 2953, 2870, 2251, 1717, 1585, 1499, 1454, 1439, 1392, 13677, 1324, 1251, 1202, 1168, 1112, 1047, 1001 cm$^{-1}$ s. Synthesis of Compound 26 (Boc Serine Oxazole Alcohol)

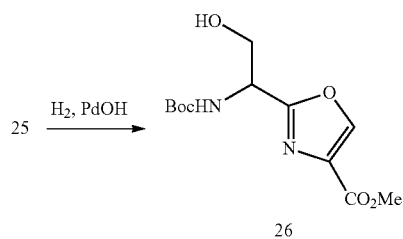 [SMILES: COC(=O)c1coc(C(CO)NC(=O)OC(C)(C)C)n1]

Compound 25 (3.10 g, 8.24 mmol) was dissolved in methanol (50 mL) and 20% palladium hydroxide on carbon (500 mg) was added to the reaction vessel. This was hydrogenated in a Parr hydrogenator at 40 psi for 72 hours. The reaction mixture was filtered through Celite while washing with methanol. The filtrate concentrated to a clear oil weighing 1.71 g, 75% (some material lost in hydrogenator). $^1$H NMR (CDCl$_3$) δ 8.21 (s, 1H), 5.67 (s, 1H), 5.02 (s, 1H), 3.96 (m, 5H), 1.45 (s, 9H). $^{13}$C NMR (CDCl$_3$) δ 143.5, 79.7, 62.8, 51.4, 49.8, 27.4 IR (thin film, NaCl) 3364, 2979, 2251, 1716, 1585, 1519, 1456, 1440, 1393, 1368, 1324, 1252, 1168, 1112, 1061, 1001, 915, 861, 804, 774, 733 cm$^{-1}$ t. Synthesis of Compound 27 (Boc-O-TIPS Serine Oxazole)

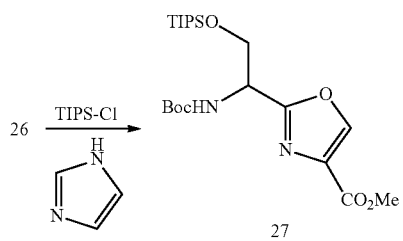

Compound 26 (1.71 g, 6 mmol) was dissolved in dry DMF (15 mL) and imidazole (1.02 g, 15 mmol, 2.5 eq) was added to the flask. This was placed under argon and treated with TIPS-Cl (1.52 mL, 7.2 mmol, 1.2 eq). The reaction stirred at room temperature overnight and then poured into water. This was extracted with ethyl acetate and the combined organic layers were washed with brine and dried with sodium sulfate. Concentration afforded yellow oil that was flash chromatographed on SiO$_2$ with 5-15% ethyl acetate/hexane. This was concentrated to a clear oil weighing 1.9 g, 72%. $^1$H NMR (CDCl$_3$) δ 8.20 (s, 1H), 5.58 (d, 1H, J=8), 5.03 (m, 1H), 4.09 (dq, 2H, J=3, 19), 3.92 (s, 3H), 1.17 (m, 3H), 1.07 (s, 9H), 1.02 (m, 18H). $^{13}$C NMR (CDCl$_3$) δ 169.3, 169.1, 163.0, 160.7, 143.1, 132.5, 79.3, 64.1, 51.3, 50.4, 27.4, 17.0, 11.5. IR (thin film NaCl) 3447, 3353, 3159, 3112, 2944, 2892, 2867, 2756, 2723, 2251, 1720, 1585, 1500, 1463, 1391, 1367, 1324, 1250, 1171, 1113, 1068, 998, 920, 882, 804, 766, 733, 684, 660 cm$^{-1}$ u. Synthesis of Compound 28 (TIPS Serine Oxazole Amine)

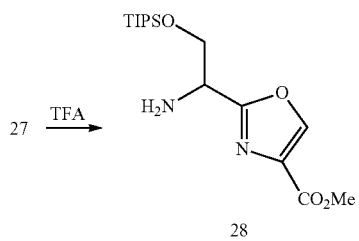

Compound 27 (1.9 g, 4.3 mmol) was dissolved in CH$_2$Cl$_2$ (5 mL) and cooled to 0° C. Then TFA (5 mL) was added and the reaction stirred under a drying tube for 2 hours. The reaction mixture was concentrated and azeotroped with benzene twice. The residue was dissolved in CH$_2$Cl$_2$ and poured into saturated NaHCO$_3$. The layers were separated and the aqueous layer was extracted with CH$_2$Cl$_2$. The combined organic layers were dried with sodium sulfate and concentrated to a pale yellow oil weighing 1.43 g, 97%. $^1$H NMR (CDCl$_3$) δ 8.21 (s, 1H), 4.21 (t, 1H, J=5), 4.04 (d, 1H, J=5), 3.92 (s, 3H), 3.74 (d, 1H, J=3), 2.23 (s, 2H), 1.02 (m, 21H). $^{13}$C NMR (CDCl$_3$) δ 165.7, 160.8, 143.1, 132.3, 65.5, 55.6, 51.5, 16.9, 10.9. IR (thin film, NaCl) 3376, 3315, 3168, 2944, 2893, 2866, 2762, 2726, 2625, 2247, 1744, 1673, 1583, 1514, 1463, 1439, 1384, 1367, 1345, 1323, 1203, 1110, 1069, 998, 918, 883, 841, 803, 769, 733, 683, 660, 647 cm$^{-1}$ Example 2

Synthesis of Compound 16

Cyclic Lysine-Valine Dimethyl Amine

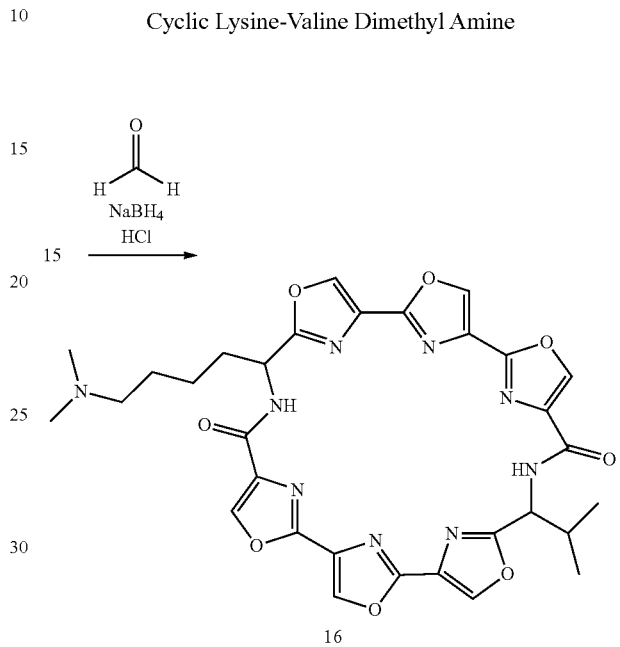

Compound 15 (21 mg, 0.029 mmol) was dissolved in methanol (1 mL) and water (1 mL) with 1 drop of HCl. This was cooled to 0° C. and 37% aqueous formaldehyde (30 μL, 0.3 mmol, 10 eq) was added. After stirring for 5 minutes, sodium borohydride (11 mg, 0.29 mmol, 10 eq) was slowly added to avoid excessive foaming. Then additional formaldehyde (30 μL, 0.3 mmol, 10 eq) was added and the pH was adjusted to 3 with concentrated HCl. After stirring at 0° C. for 8 hours, the pH was neutralized with 3N NaOH and the reaction mixture was concentrated. The residue was triturated with ethanol and filtered to remove precipitated NaCl. The residue was dissolved in 10 mL of methanol and half of the solution was stirred with Amberlyst A-15 resin. After stirring for 1 hour the solvent was removed and the resin was washed with methanol. The resin was then stirred with a solution of methanolic ammonia to release the product from the resin. After stirring for 2 hours the resin was filtered and the filtrate was concentrated to give 2 mg of product. The other half of the methanol solution was concentrated and triturated with 30% hexane/chloroform. The organic solvent was removed by pipette to give the product as a white solid weighing 10 mg. Total product obtained was 12 mg, 67%. Melting point 308-310° C. (decomposed). Optical rotation [α]$_D^{24}$=+19° (c=0.5 g/100 mL in 20% CHCl$_3$/MeOH). $^1$H NMR (CDCl$_3$) δ 8.76 (d, 1H, J=8), 8.41 (d, 1H, J=8), 8.23 (m, 6H), 5.48 (dt, 1H, J=6, 7), 5.34 (dd, 1H, J=5, 8), 2.96 (m, 2H), 2.88 (s, 3H), 2.11 (m, 3H), 1.90 (m, 5H), 0.99 (m, 8H). $^{13}$C NMR (CDCl$_3$+CD$_3$OD) δ 164.9, 140.2, 139.0, 138.5, 138.2, 128.2, 52.3, 39.7, 32.3, 17.8, 17.5 IR (thin film, NaCl) 3388, 2959, 2926, 1660, 1595, 1458, 1107 cm$^{-1}$. HRMS (FAB) m/z calcd for C$_{31}$H$_{31}$N$_9$O$_8$Li (M+Li) 658.2368; found, 658.2373

Example 3

Synthesis of Compound 17

Cyclic Lysine-Valine Acetyl Amide

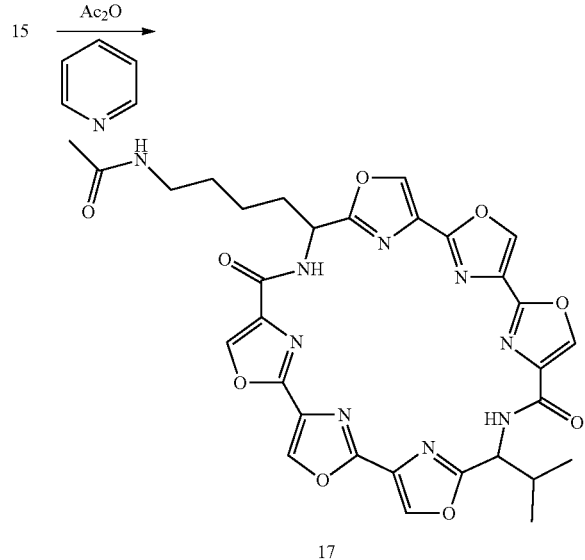

Compound 15 (12.8 mg, 0.017 mmol) was treated with a mixture of acetic anhydride (1 mL) and dry pyridine (1 mL). This stirred at room temperature under a drying tube for 6 hours. The solvent was then removed by azeotroping with toluene twice. The residue was chromatographed on $SiO_2$ with 1% $MeOH/CHCl_3$ to afford 8 mg of white solid, 72%. Melting point 222-224° C.; Optical rotation $[\alpha]_D^{24}=-37.4°$ (c=0.605 g/100 mL in 10% $MeOH/CHCl_3$). $^1H$ NMR ($CDCl_3$) δ 8.60 (d, 1H, J=8), 8.48 (d, 1H, J=8), 8.23 (m, 6H), 5.78 (br s, 1H), 5.43 (dt, 1H, J=6, 7), 5.33 (dd, 1H, J=5, 8), 3.22 (m, 2H), 2.40 (m, 1H), 1.75 (m, 5H), 1.44 (m, 4H), 1.05 (d, 3H, J=7), 0.99 (d, 3H, J=7). IR (thin film, NaCl) 3368, 3153, 3047, 2964, 2930, 2871, 2359, 2340, 1660, 1597, 1510, 1468, 1441, 1372, 1359, 1269, 1190, 1105, 974, 915, 878, 810, 774, 722, 695 cm$^{-1}$

Example 4

Synthesis of Compound 50

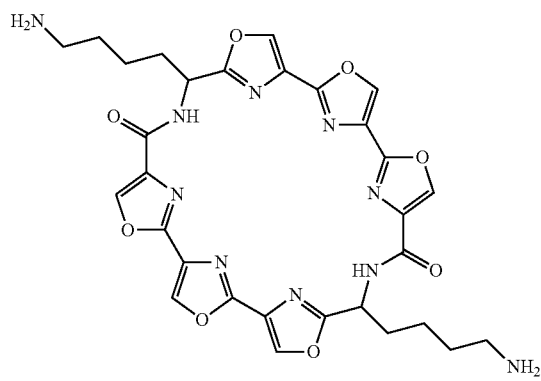

a. Synthesis of Compound 18 (Lysine Amine Teroxazole)

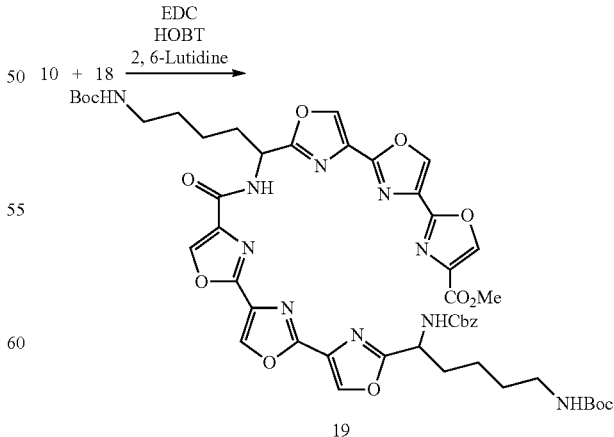

Compound 8 (620 mg, 1.04 mmol) was dissolved in a mixture of THF (35 mL) and ethanol (10 mL) and stirred with 20% palladium hydroxide on carbon (100 mg) and $H_2$ (1 atm) overnight. Starting material was still present so additional palladium hydroxide (50 mg) was added and stirred again overnight, but the reaction was still not complete. Added an additional 20 mg of palladium hydroxide and stirred overnight again after which the reaction was finally complete. The mixture was filtered through Celite washing with 10% methanol/$CH_2Cl_2$. This was concentrated to a thick yellow oil. Impurities formed due to the long reaction time were removed by recrystallizing the product from benzene to give 325 mg of a pale yellow solid, 68%. Melting point 135-139° C. $^1H$ NMR ($CDCl_3$) δ 8.39 (m, 3H), 4.90 (m, 1H) 3.95 (m, 3H), 3.08 (m, 2H), 2.17 (m, 2H), 1.90 (m, 2H), 1.40 (s, 14H)

$^{13}C$ NMR ($CDCl_3$) δ 160.3, 155.3, 143.2, 138.6, 133.4, 129.7, 78.1, 68.9, 51.4, 39.2, 32.1, 27.5, 21.7. IR (nujol) 3353, 3144, 2361, 1715, 1690, 1573, 1521, 1377, 1326, 1282, 1251, 1170, 1114, 1001, 973, 915, 805, 776, 725 cm$^{-1}$ HRMS (FAB) m/z calcd for $C_{21}H_{27}N_5O_7Li$ (M+Li) 468.2065; found, 468.2082 b. Synthesis of Compound 19 (Linear Protected Dilysine Hexaoxazole)

Compound 10 (327 mg, 0.56 mmol), Compound 18 (260 mg, 0.56 mmol), EDC (216 mg, 1.13 mmol, 2 eq) and HOBT (152 mg, 1.13 mmol, 2 eq) were dissolved in dry DMF (100 mL) and placed under argon. This was cooled to 0° C. and 2,6-lutidine (0.33 mL, 2.8 mmol, 5 eq) was added. This warmed to room temperature overnight after which the solvent was removed under reduced pressure. The residue was dissolved in CH$_2$Cl$_2$ and washed successively with saturated NaHCO$_3$, 5% HCl and brine. The aqueous layers were all back extracted with ethyl acetate. The combined organic layers were dried with sodium sulfate and concentrated to an orange solid. This was recrystallized from benzene to give 133 mg of product, 23%. Melting point 186-189° C.; Optical rotation $[\alpha]_D^{23}=-3.15°$ (c=1.65 g/100 mL in CHCl$_3$). $^1$H NMR (CDCl$_3$) δ 8.44 (m, 2H), 8.32 (m, 4H), 7.54 (d, 1H, J=9), 7.35 (m, 5H), 5.51 (m, 2H), 5.13 (s, 2H), 5.04 (m, 1H), 4.58 (m, 2H), 3.95 (s, 3H), 3.10 (m, 4H), 2.05 (m, 4H), 1.46 (m, 26H). $^{13}$C NMR (CDCl$_3$) δ 164.7, 164.0, 158.9, 155.1, 143.0, 140.8, 138.8, 138.5, 135, 130.0, 127.6, 127.3, 78.3, 66.4, 51.4, 48.6, 46.0, 39.1, 32.8, 28.7, 27.5, 21.9, 21.5. IR (nujol) 3408, 3364, 3159, 1715, 1690, 1644, 1600, 1574, 1522, 1377, 1364, 1282, 1170, 1114, 1001, 976, 915, 725 cm$^{-1}$.

c. Synthesis of Compound 20 (Linear Dilysine Hexaoxazole Amine)

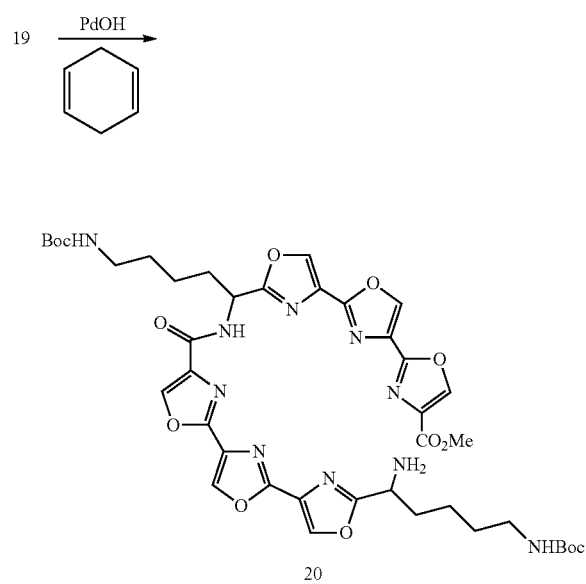

Compound 19 (130 mg, 0.13 mmol) was dissolved in 30% ethyl acetate in methanol (130 mL) and refluxed with 20% palladium hydroxide (25 mg) and 1,4-cyclohexadiene (2 mL) overnight. Then additional palladium hydroxide (40 mg) and 1,4-cyclohexadiene (1 mL) were added and refluxed for 48 hours. After adding more palladium hydroxide (50 mg) and refluxing overnight the reaction was cooled and filtered though Celite washing with 20% methanol/CH$_2$Cl$_2$. This was concentrated to a white solid weighing 111 mg, 98%. Melting point 170-173° C. $^1$H NMR (CDCl$_3$+CD$_3$OD) δ 8.65 (m, 3H), 8.56 (m, 2H), 8.50 (s, 1H), 5.45 (dt, 1H, J=1, 8), 4.56 (m, 1H), 3.95 (s, 3H), 3.08 (m, 4H), 2.14 (m, 6H), 1.48 (m, 28H) $^{13}$C NMR (CDCl$_3$+CD$_3$OD) δ 165.2, 161.5, 160.8, 144.6, 142.2, 141.1, 140.5, 140.2, 133.9, 130.6, 129.6, 129.5, 125.1, 78.9, 51.9, 39.9, 32.7, 35.5, 29.9, 29.2, 27.9, 22.8, 22.2. IR (nujol) 3360, 3151, 2362, 2334, 1715, 1682, 1660, 1519, 1455, 1365, 1282, 1251, 1167, 115, 973, 914, 725 cm$^{-1}$.

d. Synthesis of Compound 21 (Linear Dilysine Hexaoxazole Fully Deprotected)

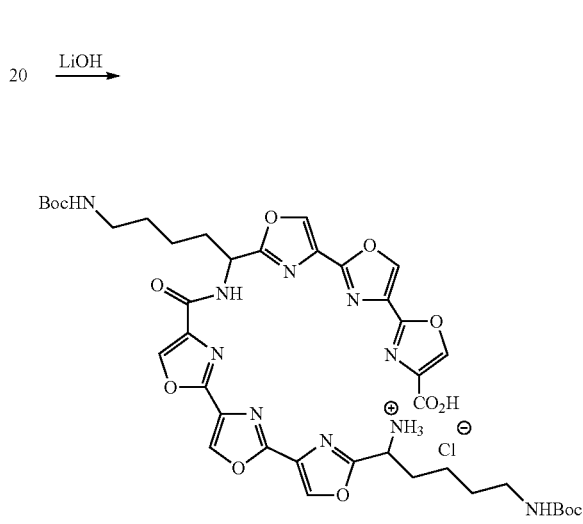

Compound 20 (111 mg, 0.12 mmol) was dissolved in a 3:1 mixture of THF and water (13 mL) and cooled to 0° C. Then LiOH (10 mg, 0.24 mmol, 2 eq) was added and the reaction warmed to room temperature overnight. The solvent was then removed and the aqueous solution was acidified with 1N HCl (1 mL). This was concentrated and azeotroped with toluene to give 110 mg of the hydrochloride salt as a white solid, 99%. Melting point 265-269° C. $^1$H NMR (DMSO) δ 9.06 (m, 3H), 8.97 (m, 2H), 8.90 (s, 1H), 8.75 (br s, 2H), 6.79 (m, 1H), 5.25 (m, 1H), 4.46 (m, 2H), 2.82 (m, 8H), 1.99 (m, 6H), 1.60 (m, 6H), 1.34 (m, 18H) $^{13}$C NMR (CDCl$_3$+CD$_3$OD) δ 168.6, 164.2, 159.5, 155.3, 155.2, 155.1 153.6, 142.3, 139.3, 135.4, 129.5, 129.5, 128.7, 128.4, 127.5, 124.5, 78.4, 39.1, 33.4, 32.1, 30.3, 29.3, 28.4, 27.3, 25.9, 21.8, 21.2. IR (nujol) 3396, 2367, 2360, 1633, 1375, 1260, 1105 cm$^{-1}$ e. Synthesis of Compound 22 (Cyclic Boc-Dilysine Hexaoxazole)

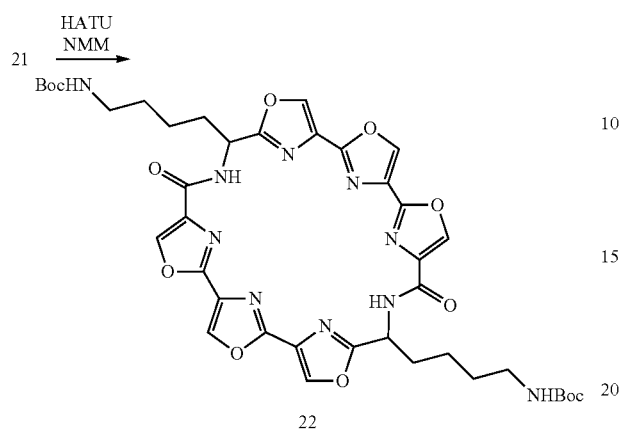

Compound 21 (100 mg, 0.12 mmol) was dissolved in dry DMF (60 mL) and CH$_2$Cl$_2$ (120 mL) and placed under argon. After cooling to 0° C., N-methylmorpholine (30 μL, 0.26 mmol, 2.2 eq) and a solution of HATU (55 mg, 0.14 mmol, 1.2 eq) in DMF (1 mL) were added. This warmed to room temperature overnight and the solvent was then removed. This was chromatographed with 1-2% MeOH/CHCl$_3$ on SiO$_2$ to give 7 mg of product as a white solid, 7%. Melting point 168° C.; Optical rotation $[\alpha]_D^{24}$=−6.0° (c=0.25 g/100 mL in 10% MeOH/CHCl$_3$) $^1$H NMR (CDCl$_3$) δ 8.54 (d, 1H, J=7), 8.30 (d, 1H, J=8), 8.22 (m, 6H), 7.35 (s, 1H), 5.46 (m, 2H), 4.55 (s, 1H), 3.07 (m, 4H), 1.99 (m, 6H), 1.29 (m, 24H) $^{13}$C NMR (CDCl$_3$) δ 153.8, 142.5, 140.4, 138.3, 137.5, 46.9, 39.5, 34.2, 28.7, 27.5, IR (thin film, NaCl) 3383, 3326, 3145, 2929, 2866, 1673, 1595, 1510, 1455, 1366, 1271, 1251, 1170, 1107, 973, 916, 724 cm$^{-1}$ f. Synthesis of Compound 50

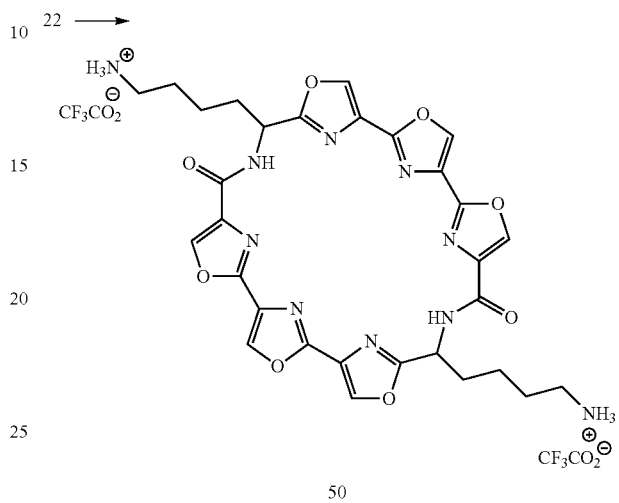

Compound 22 will be converted to Compound 50 by removing the protecting groups.

Example 5

Synthesis of Compounds 111a-111e

Compounds 111a-111e were prepared as illustrated below.

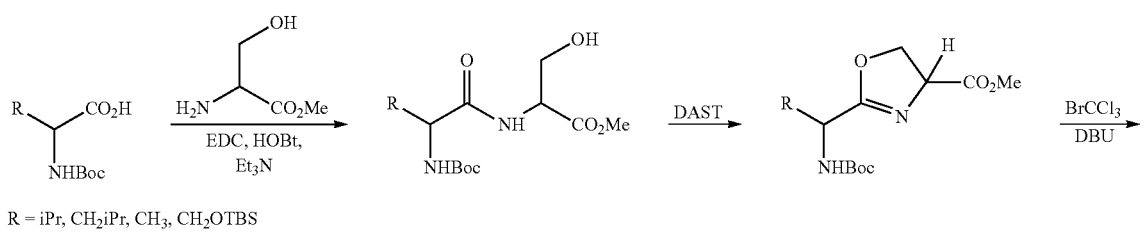

R = iPr, CH$_2$iPr, CH$_3$, CH$_2$OTBS

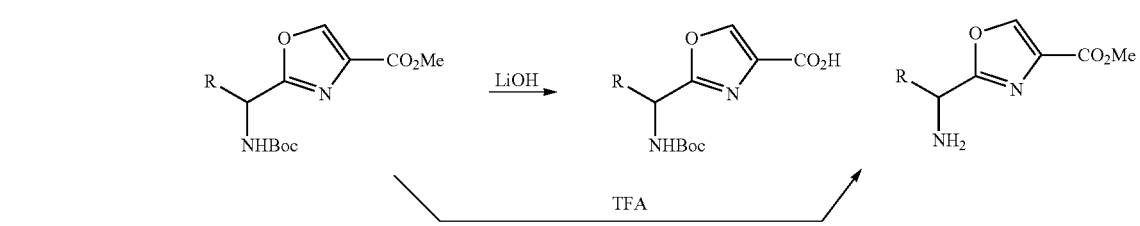

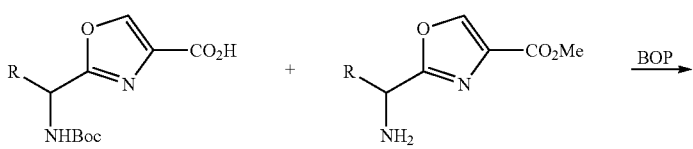

61 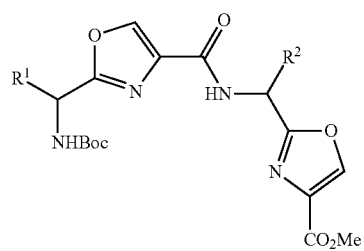 →LiOH→ 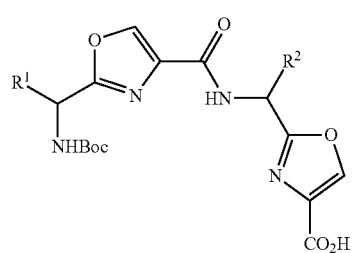 
62 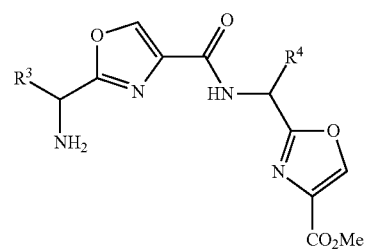
-continued
+ TFA ↗
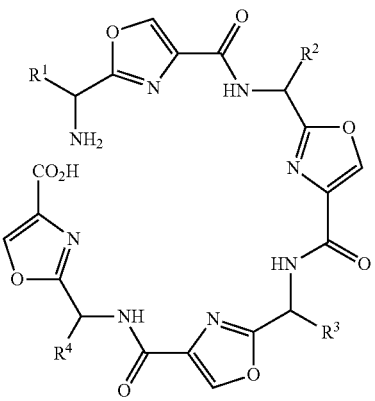 →BOP, DIPEA→
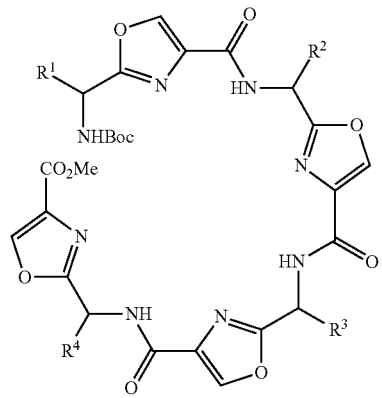 →1) TFA 2) LiOH→ (10) →BOP DIPEA→
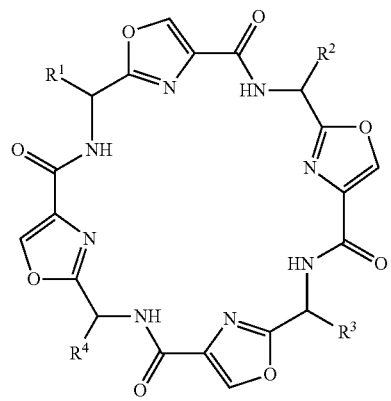
111a R¹, R², R³, R⁴ = iPr
111b R¹, R² = iPr, R³, R⁴ = CH₂iPr
111c R¹, R³ = iPr, R², R⁴ = CH₂iPr
111d R¹, R², R³, R⁴ = CH₂iPr
111e R¹, R², R³, R⁴ = CH₃
111f R¹, R³ = iPr, R², R⁴ = CH₂OTBDPS
111g R¹, R³ = CH₂OTBS, R³, R⁴ = CH₂OTBDPS
111h R¹ = iPr, R² = CH₂OTBS, R³, R⁴ = CH₂OTIPS Compound 111a:

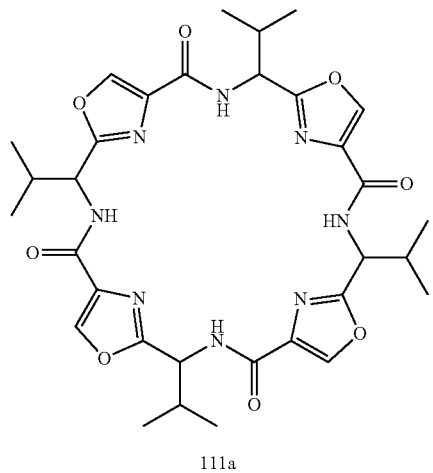

Yellow solid; mp. 122-128° C.; $^1$H NMR δ 8.15 (s, 4H), 7.27 (d, 4H, J=9.4), 5.26 (m, 4H), 2.34 (m, 4H), 1.08 (d, 12H, J=6.6), 0.98 (d, 12H, j=6.6); $^{13}$C NMR δ 163.8, 159.8, 141.6, 135.8, 51.7, 32.9, 19.0, 18.7; HRMS (M+Li$^+$) Calcd for $C_{32}H_{40}N_8O_8$(Li): 671.3129; Found: 671.3148.

Compound 111b:

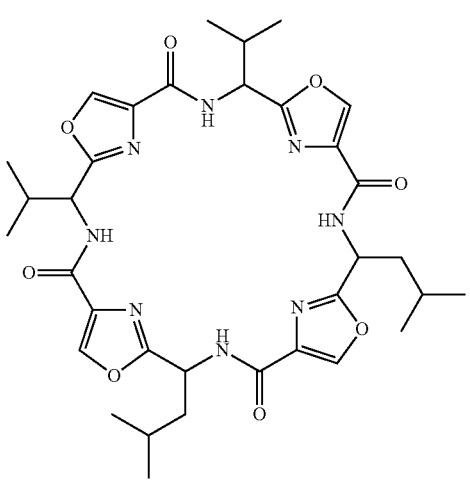

Yellowish white solid; mp. 132° C.-134° C.; $^1$H NMR δ 8.14 (s, 2H), 8.11 (s, 2H), 7.31 (d, 2H, J=9.6), 7.14 (d, 2H, J=9.6), 5.51 (m, 2H), 5.23 (dd, 2H, J=10, 7), 2.28 (m, 2H), 1.94 (m, 6H), 1.02 (d, 12H, J=6.2), 0.93 (d, 12H, J=6.2); $^{13}$C NMR δ 164.4, 163.9, 160.2, 159.8, 159.5, 141.7, 141.6, 135.8, 135.6, 51.8, 45.5, 44.3, 42.9, 33.1, 32.4, 24.9, 24.8, 22.7, 22.6, 22.3, 22.1, 21.9, 19.0, 18.9, 18.5; HRMS (FAB) calcd for $C_{34}H_{44}N_8O_8$(Na): 715.3180; Found: 715.3174.

Compound 111c:

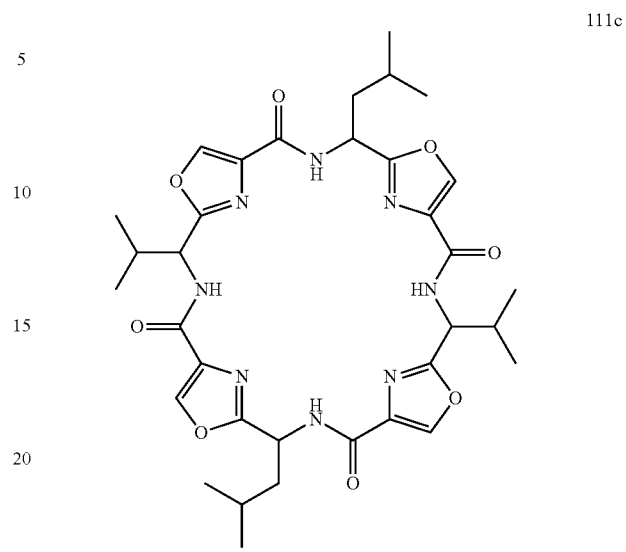

Yellowish white solid; mp. 124-128° C.; $^1$H NMR δ 8.12 (s, 4H), 7.21 (m, 4H), 5.25 (m, 4H), 2.30 (m, 2H), 1.86 (m, 6H), 0.96 (d, 12H, J=6.6), 0.94 (d, 12H, J=6.6); $^{13}$C NMR δ 164.7, 164.6, 163.8, 163.7, 160.1, 159.8, 159.6, 141.7, 141.6, 135.7, 135.5, 52.5, 51.6, 45.4, 44.6, 44.5, 43.4, 42.4, 32.8, 32.4, 24.9, 24.7, 22.6, 22.5, 22.3, 22.2, 22.1, 21.9, 19.1, 18.6; HRMS (FAB) calcd for $C_{34}H_{44}N_8O_8$(Na): 715.3180; Found: 715.3148.

Compound 111d:

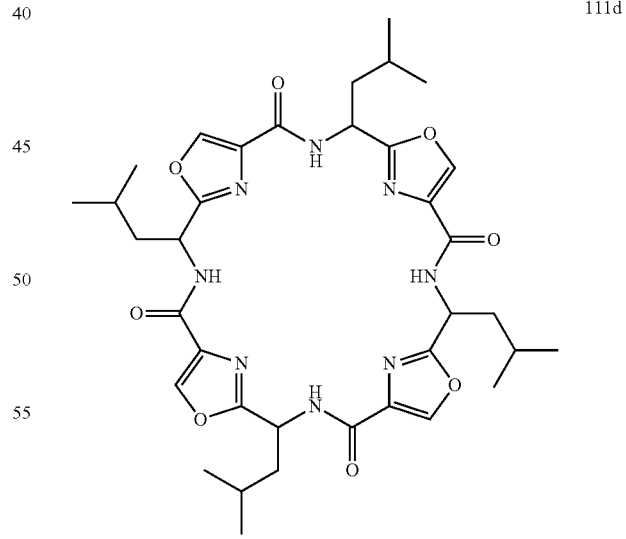

White solid; mp. 122° C.-128° C.; $^1$H NMR (CDCl$_3$) δ 8.14 (s, 4H), 7.21 (d, 4H, J=9.2), 5.51 (m, 4H), 1.80 (m, 12H), 1.02 (d, 12H, J=6.6), 0.99 (d, 12H, J=6.6); $^{13}$C NMR δ 164.6, 159.6, 141.6, 135.7, 44.6, 43.5, 24.9, 22.7, 22.3; HRMS (FAB) Calcd for $C_{36}H_{48}N_8O_8$(Li): 727.3755; Found: 727.3756.

Example 6

Synthesis of Compound 219 a. Synthesis of Compound 201 (N-Boc Serine Amide)

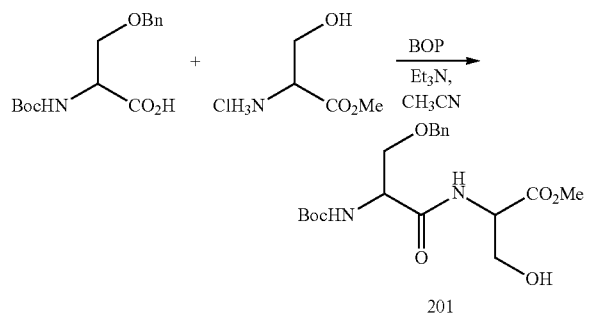

Dry acetonitrile (200 mL) was added to a mixture of N-Boc-O-Benzyl serine (5.9 g, 20 mmol) and serine methyl ester hydrochloride (3.1 g, 20 mmol) and stirred for 5 min. BOP (8.84 g, 20 mmol) and triethylamine (6.2 mL, 44 mmol) were added and the mixture was stirred at room temperature for 12 h. The mixture was then evaporated under reduced pressure and diluted with EtOAc and brine. The phases were separated and then aqueous phase was extracted with EtOAc. The combined organic phases were then washed successively with 1N HCl, saturated NaHCO$_3$, and brine and then dried over Na$_2$SO$_4$, filtered and evaporated to give the amide as a colorless oil, 7.92 g (100%); $^1$H NMR (CDCl$_3$) δ 7.56 (d, 1H, J=7.6), 7.24 (m, 5H), 5.89 (d, 1H, J=5.8), 4.59 (m, 1H), 4.46 (s, 2H), 4.40 (m, 1H), 3.98 (m, 4H), 3.62 (s, 3H), 1.38 (s, 9H); $^{13}$C-NMR δ 170.8, 155.9, 137.7, 128.4, 127.8, 80.3, 73.3, 70.2, 69.9, 62.5, 62.4, 60.4, 54.9, 54.6, 52.5, 28.3, 20.9, 14.2.

b. Synthesis of Compound 202 (N-Boc Serine Oxazoline Methyl Ester)

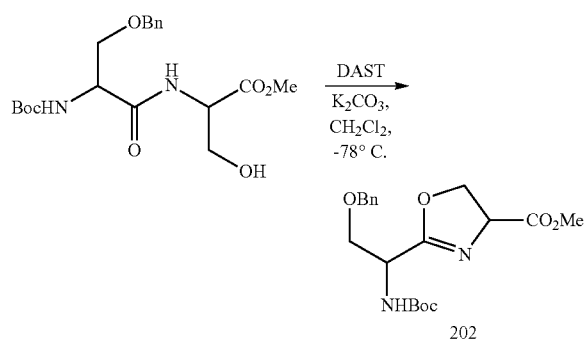

A solution of 201 (7.92 g, 20 mmol) in CH$_2$Cl$_2$ (40 mL) was cooled to −78° C. under nitrogen and treated with DAST (4.34 mL, 33.1 mmol). After stirring for 1.5 h anhydrous K$_2$CO$_3$ was added and the mixture was then allowed to warm to room temperature. The mixture was poured into saturated NaHCO$_3$ and extracted several times with CH$_2$Cl$_2$. The combined extracts were dried over Na$_2$SO$_4$, filtered and concentrated to give oxazoline 202 as a red-yellow oil, 6.05 g (80%, crude); $^1$H NMR (CDCl$_3$) δ 7.29 (m, 5H), 5.51 (d, 2H, J=8.0), 3.76 (s, 3H), 1.43 (s, 9H); $^{13}$C-NMR δ 171.2, 168.4, 155.3, 137.9, 128.4, 127.7, 127.6, 80.0, 73.3, 73.2, 70.3, 68.1, 68.0, 52.7, 49.5, 28.4.

c. Synthesis of Compound 203 (N-Boc Serine Oxazole Methyl Ester)

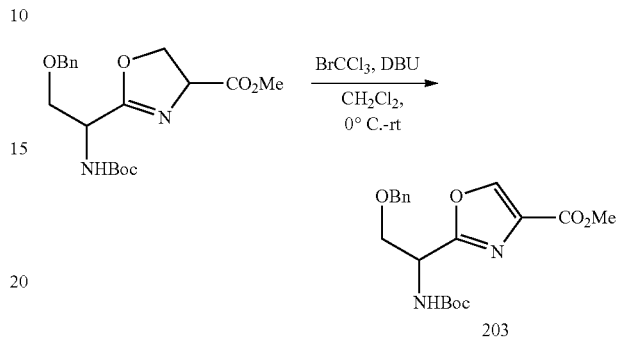

A solution of the crude oxazoline (6.05 g, 16 mmol) in dry CH$_2$Cl$_2$ (50 mL) was stirred under nitrogen at 0° C. as dry DBU (3.7 mL, 25.6 mmol) was added over 2 min followed by BrCCl$_3$ (2.6 mL, 25.6 mmol) which was then added over 5 min. the reaction was stirred at 0° C. for 5 h and was then poured into saturated NH$_4$Cl. The mixture was extracted with CH$_2$Cl$_2$ and the combined extracts were dried over Na$_2$SO$_4$, filtered, and evaporated. The product was purified by flash chromatography on silica gel eluting with 2:3 EtOAc/hexane to give the oxazole as a colorless oil, 4.51 g (75%); $^1$H NMR (CDCl$_3$) δ 8.14 (s, 1H), 7.42 (m, 5H), 5.66 (d, 1H, J=8.8), 5.08 (m, 1H), 4.43 (s, 2H), 3.82 (s, 3H), 3.71 (m, 2H), 1.38 (s, 9H); $^{13}$C NMR δ 163.6, 161.5, 155.2, 144.3, 137.4, 133.4, 128.4, 127.8, 127.6, 80.2, 73.2, 70.4, 52.1, 49.4, 28.3.

d. Synthesis of Compound 204 (Amino Oxazole)

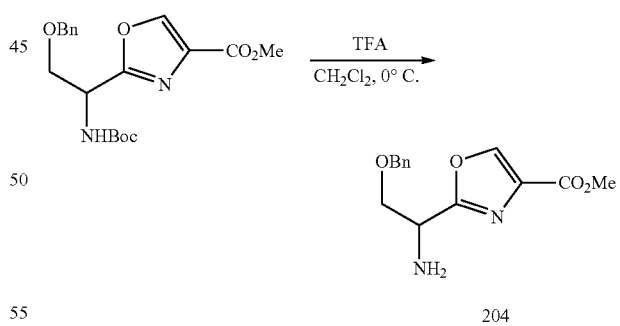

A solution of the Boc derivative (4.51 g, 12 mmol) in CH$_2$Cl$_2$ (10 mL) was cooled to 0° C. under protection from moisture by a drying tube. TFA (10 mL) was added and the solution was stirred for 1.5 h. Solvents were evaporated under reduced pressure and residual TFA was removed as an azeotrope with benzene. The residue was taken up in CH$_2$Cl$_2$ and washed with saturated NaHCO$_3$ and was then dried over Na$_2$SO$_4$, filtered, and evaporated to give the amine as a yellow-red oil, 3.24 g (98%); $^1$H NMR (CDCl$_3$) δ 8.19 (s, 1H), 7.29 (m, 5H), 4.54 (s, 2H), 4.31 (dd, 1H, J=5.9, 4.8), 3.90 (s, 3H), 3.81 (m, 2H), 1.98 (s, 2H); $^{13}$C-NMR δ 166.6, 162.1, 144.6, 138.2, 133.7, 128.9, 128.3, 128.1, 73.8, 72.9, 52.7, 50.9.

e. Synthesis of Compound 205 (N-Boc Valine Amide)

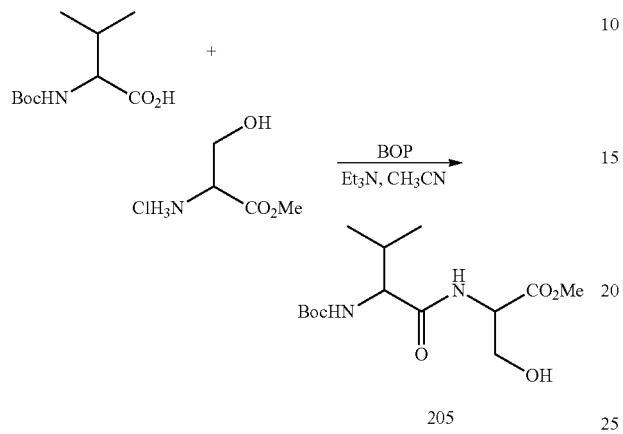

Dry acetonitrile (100 mL) was added to a mixture of N-Boc-L-valine (2.17 g, 10 mmol) and serine methyl ester hydrochloride (1.86 g, 12 mmol) and stirred for 5 min. BOP (4.42 g, 10 mmol) and triethylamine (3.1 mL, 22 mmol) were added and the mixture was stirred at room temperature for 12 h. The mixture was then evaporated under reduced pressure and diluted with EtOAc and brine. The phases were separated and then aqueous phase was extracted with EtOAc. The combined organic phases were then washed successively with 1N HCl, saturated NaHCO$_3$, and brine and then dried over Na$_2$SO$_4$, filtered and evaporated to give the amide as a colorless oil, 3.18 g (100%); $^1$H NMR (CDCl$_3$) δ 7.45 (dd, 1H, J=1.4), 5.58 (d, 1H, J=8.8), 4.45 (m, 1H), 4.37 (m, 1H), 3.79 (m, 2H), 3.54 (s, 3H), 1.88 (m, 1H), 1.23 (s, 9H), 0.74 (d, 6H, J=6.6); $^{13}$C-NMR δ 172.3, 171.0, 162.9, 156.0, 79.4, 62.3, 54.6, 52.3, 31.3, 28.2, 17.7, 17.4.

f. Synthesis of Compound 207 (N-Boc Valine Oxazoline)

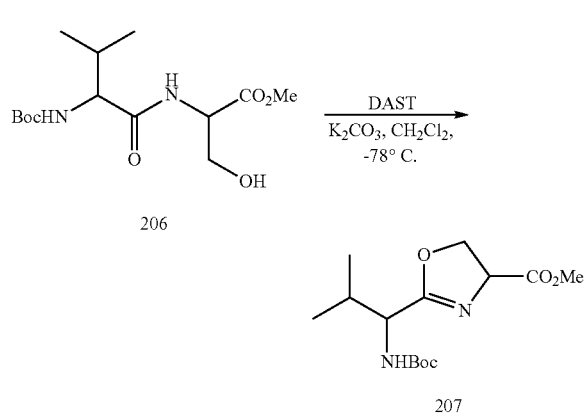

A solution of 206 (2.54 g, 8 mmol) in CH$_2$Cl$_2$ (16 mL) was cooled to −78° C. under nitrogen and treated with DAST (1.7 mL, 13.2 mmol). After stirring for 1.5 h anhydrous K$_2$CO$_3$ (1.32 g) was added and the mixture was then allowed to warm to room temperature. The mixture was poured into saturated NaHCO$_3$ and extracted several times with CH$_2$Cl$_2$. The combined extracts were dried over Na$_2$SO$_4$, filtered and concentrated to give oxazoline 207 as a red-yellow oil, 2.36 g (98%, crude); $^1$H NMR (CDCl$_3$) δ 5.12 (d, 1H, J=8.4), 4.70 (m, 1H), 4.41 (m, 3H), 3.74 (s, 3H), 2.02 (m, 1H), 1.24 (s, 9H), 0.74 (d, 6H, J=6.6); $^{13}$C-NMR δ 171.3, 169.5, 155.5, 79.6, 69.8, 67.8, 54.1, 52.6, 31.8, 28.3, 17.7, 17.3.

g. Synthesis of Compound 208 (N-Boc Valine Oxazole)

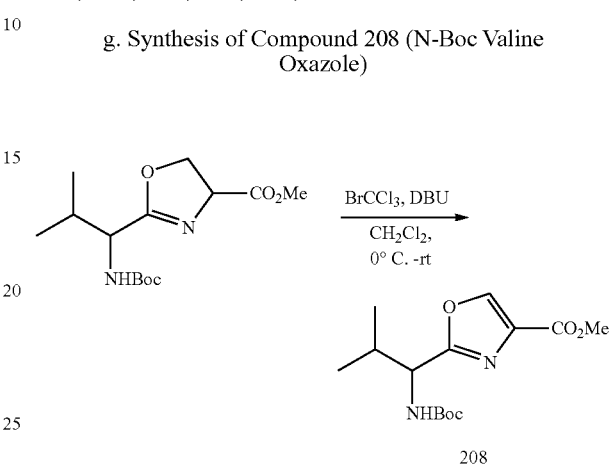

A solution of the crude oxazoline (2.36 g, 7.9 mmol) in dry CH$_2$Cl$_2$ (24 mL) was stirred under nitrogen at 0° C. as dry DBU (1.8 mL, 12.5 mmol) was added over 2 min followed by BrCCl$_3$ (1.2 mL, 12.5 mmol) which was then added over 5 min. The reaction was stirred at 0° C. for 5 h and was then poured into saturated NH$_4$Cl. The mixture was extracted with CH$_2$Cl$_2$ and the combined extracts were dried over Na$_2$SO$_4$, filtered, and evaporated. The product was purified by flash chromatography on silica gel eluting with 2:3 EtOAc/hexane to give the oxazole as a white solid, 2.36 g (75%); mp 125-129° C.; $^1$H NMR (CDCl$_3$) δ 8.1 (s, 1H), 5.31 (d, 1H, J=9.2), 4.63 (dd, 1H, J=9, 6), 3.73 (s, 3H), 2.04 (m, 1H), 1.25 (s, 9H), 0.74 (d, 6H, J=6.6); $^{13}$C NMR δ 165.0, 161.5, 155.3, 143.9, 133.0, 79.7, 54.2, 52.0, 32.8, 28.2, 18.6, 17.9.

h. Synthesis of Compound 209 (N-Boc Valine Oxazole Carboxylic Acid)

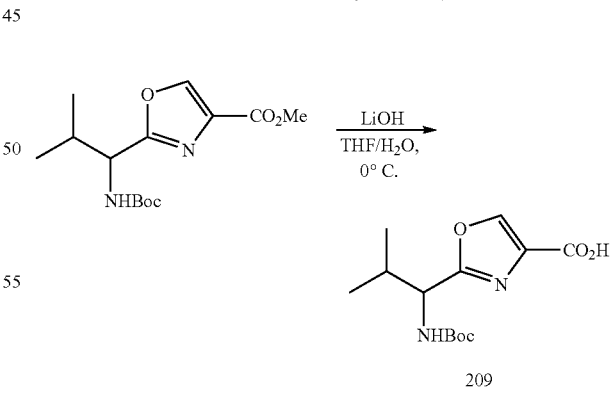

A solution of the ester (0.8 g, 2.68 mmol) in 3:1 THF/H$_2$O (32 mL) was stirred at 0° C. as LiOH (134 mg, 3.19 mmol) was added in one portion. The reaction mixture was stirred for 10 h and was then evaporated under reduced pressure to remove THF. The aqueous solution was brought to pH 3 with 1N HCl and was then extracted with EtOAc. The organic phase was washed with brine and dried over Na$_2$SO$_4$, filtered and evaporated to give the carboxylic acid as a white solid, 0.67 g (88%); mp 157-160° C.; $^1$H NMR (CDCl$_3$) δ 8.2 (s, 1H), 6.34 (d, 1H, J=8.4), 4.78 (t, 1H, J=8.3), 2.16 (m, 1H), 1.33 (s, 9H), 0.87 (dd, 6H, J=14, 7); $^{13}$C NMR δ 166.4, 163.9, 155.9, 144.3, 133.8, 79.9, 54.6, 32.8, 28.3, 18.8, 18.3.

i. Synthesis of Compound 210 (N-Boc Valine O-Benzyl Bisoxazole Amide)

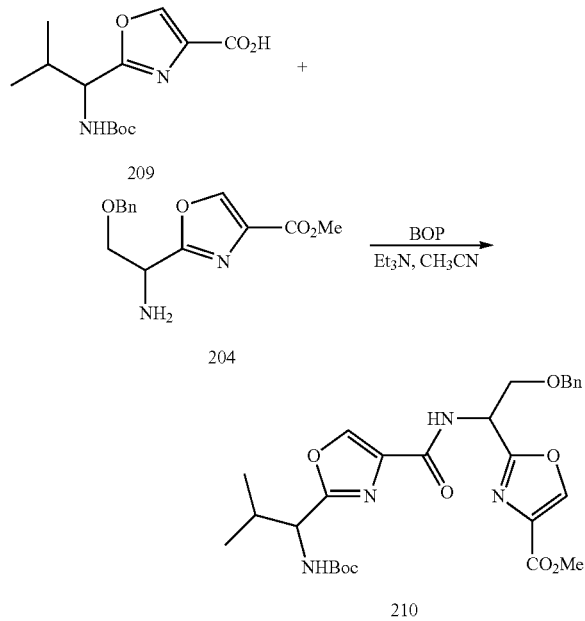

Dry acetonitrile (100 mL) was added to a mixture of amine 204 (3.24 g, 11.7 mmol) and acid 209 (3.33 g, 11.7 mmol) and stirred for 5 min. BOP (5.17 g, 11.7 mmol) and triethylamine (3.6 mL, 25.7 mmol) were added and the mixture was stirred at room temperature for 12 h. The mixture was then evaporated under reduced pressure and diluted with EtOAc and brine. The phases were separated and then aqueous phase was extracted with EtOAc. The combined organic phases were washed successively with 1N HCl, saturated NaHCO$_3$, and brine and then dried over Na$_2$SO$_4$, filtered and evaporated to give the amide as a colorless oil, 4.76 g (90%); $^1$H NMR (CDCl$_3$) δ 8.34 (s, 1H), 8.22 (s, 1H), 7.91 (d, 1H, J=8.4), 7.42 (m, 5H), 5.73 (m, 1H), 5.53 (m, 1H), 4.87 (m, 1H), 4.68 (s, 2H), 4.18 (m, 2H), 4.01 (s, 3H), 2.28 (m, 1H), 1.58 (s, 9H), 1.08 (d, 3H, J=6.6), 1.04 (d, 3H, J=7.0); $^{13}$C-NMR δ 163.2, 161.9, 161.8, 160.5, 159.5, 154.5, 143.4, 140.6, 136.4, 134.4, 132.5, 127.5, 126.9, 126.7, 79.1, 72.2, 68.9, 53.4, 51.2, 46.4, 31.7, 27.4, 17.9, 17.2.

j. Synthesis of Compound 211 (N-Boc Valine Serine Amide)

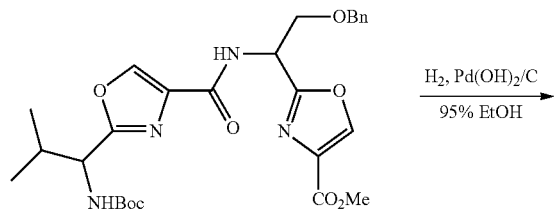

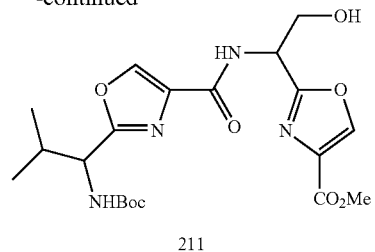

A solution of benzyl ether 9 (5.72 g, 10.6 mmol) in 95% EtOH (75 mL) was treated with 20% Pd(OH)$_2$/C (572 mg) and shaken in a Parr apparatus under 35 psi H$_2$ for 30 h at room temperature. The catalyst was filtered through a pad of Celite and the solvent was evaporated to give the alcohol as a colorless oil, 4.54 g (95%); $^1$H NMR (CDCl$_3$) δ 8.69 (d, 1H, J=8.2), 8.36 (s, 1H), 8.29 (s, 1H), 6.19 (d, 1H, J=6.2), 5.66 (m, 1H), 4.77 (m, 1H), 4.33 (m, 2H), 3.97 (s, 3H), 2.25 (m, 1H), 1.55 (s, 9H), 1.04 (d, 3H, J=6.6), 0.89 (d, 3H, J=6.6); $^{13}$C-NMR δ 163.2, 162.9, 161.9, 160.7, 160.5, 160.4, 154.7, 143.5, 140.9, 140.5, 134.2, 132.1, 127.4, 79.2, 61.7, 53.4, 51.4, 49.1, 48.3, 31.7, 30.8, 27.4, 18.2, 17.9, 17.3, 17.1.

k. Synthesis of Compound 212 (N-Boc Valine Dihydroteroxazole)

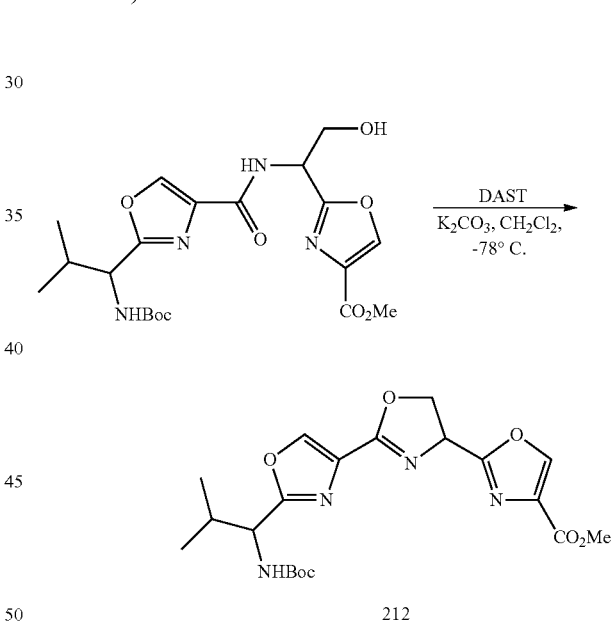

A solution of 211 (4.54 g, 10 mmol) in CH$_2$Cl$_2$ (20 mL) was cooled to −78° C. under nitrogen and treated with DAST (2.17 mL, 16.6 mmol). After stirring for 1.5 h anhydrous K$_2$CO$_3$ was added and the mixture was then allowed to warm to room temperature. The mixture was poured into saturated NaHCO$_3$ and extracted several times with CH$_2$Cl$_2$. The combined extracts were dried over Na$_2$SO$_4$, filtered and concentrated to give crude oxazoline 212 as a red-yellow foam, 3.44 g (79%, crude); $^1$H NMR (CDCl$_3$) δ 8.30 (s, 1H), 8.18 (s, 1H), 5.59 (m, 2H), 4.84 (m, 3H), 3.91 (s, 3H), 2.19 (m, 1H), 1.42 (s, 9H), 0.91 (d, 6H, J=6.8); $^{13}$C-NMR δ 164.4, 162.1, 162.0, 160.3, 159.2, 154.3, 143.9, 140.7, 132.3, 128.7, 78.7, 69.7, 53.2, 51.2, 31.9, 27.2, 17.7, 16.9.

l. Synthesis of Compound 213 (N-Boc Valine Teroxazole Ester)

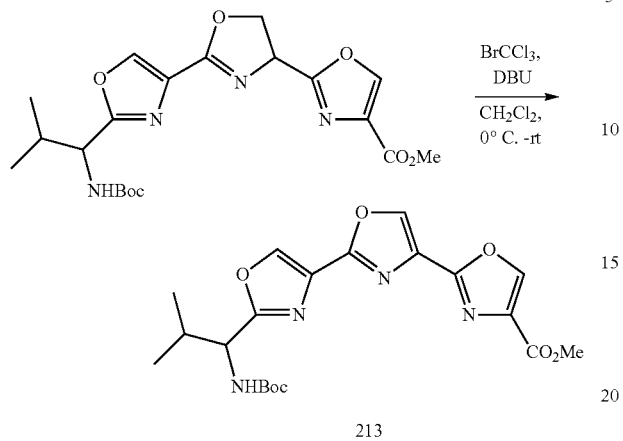

213

A solution of the crude oxazoline (3.44 g, 7.9 mmol) in dry CH$_2$Cl$_2$ (24 mL) was stirred under nitrogen at 0° C. as dry DBU (1.8 mL, 12.5 mmol) was added over 2 min followed by BrCCl$_3$ (1.2 mL, 12.5 mmol) which was then added over 5 min. The reaction was stirred at 0° C. for 5 h and was then poured into saturated NH$_4$Cl. The mixture was extracted with CH$_2$Cl$_2$ and the combined extracts were dried over Na$_2$SO$_4$, filtered, and evaporated. The product was purified by flash chromatography on silica gel eluting with 2:3 EtOAc/hexane to give the oxazole as a white solid, 1.64 g (48%); mp 214-224° C.; $^1$H NMR (CDCl$_3$) δ 8.58 (s, 1H), 8.48 (s, 1H), 8.46 (s, 1H), 5.53 (d, 1H, J=9.0), 4.95 (m, 1H), 4.08 (s, 3H), 2.35 (m, 1H), 1.56 (s, 9H), 1.07 (d, 6H, J=6.6); $^{13}$C NMR δ 164.8, 160.4, 154.5, 143.1, 138.5, 133.4, 129.9, 128.7, 79.1, 53.4, 51.4, 31.9, 27.4, 17.8, 17.1.

m. Synthesis of Compound 214 (N-Boc Valine Teroxazole Carboxylic Acid)

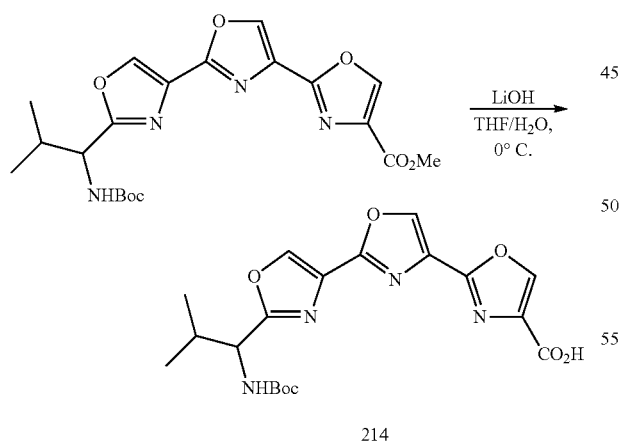

214

A solution of the ester (0.82 g, 1.9 mmol) in 3:1 THF/H$_2$O (32 mL) was stirred at 0° C. as LiOH (126 mg, 3 mmol) was added in one portion. The reaction mixture was stirred for 10 h and was then evaporated under reduced pressure to remove THF. The aqueous solution was brought to pH 3 with 1 N HCl and was then extracted with EtOAc. The organic phase was washed with brine and dried over Na$_2$SO$_4$, filtered and evaporated to give the carboxylic acid as a white solid, 0.77 g (98%); mp 225° C. (dec.); $^1$H NMR (CDCl$_3$) δ 8.44 (s, 1H), 8.39 (s, 1H), 8.32 (s, 1H), 5.39 (d, 1H, J=8.4), 4.85 (m, 1H), 2.25 (m, 1H), 1.44 (s, 9H), 0.95 (d, 6H, J=6.0); $^{13}$C NMR δ 164.8, 160.4, 154.5, 143.1, 138.5, 133.4, 129.9, 128.7, 80.1, 51.4, 31.9, 27.4, 17.8, 17.1.

n. Synthesis of Compound 215 (Amino Valine Teroxazole Ester)

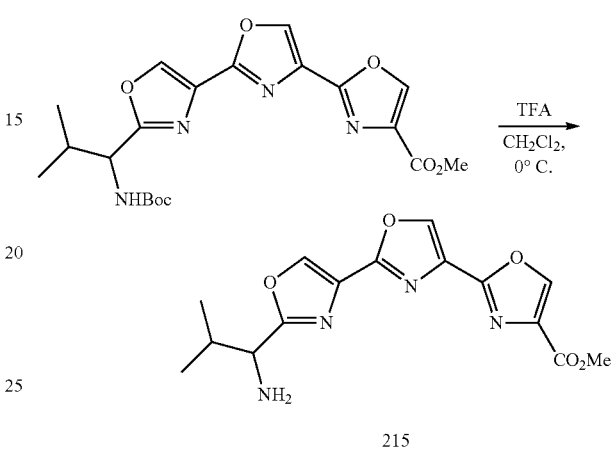

215

A solution of the N-Boc derivative (0.82 g, 1.9 mmol) in CH$_2$Cl$_2$ (10 mL) was cooled to 0° C. under protection from moisture by a drying tube. TFA (10 mL) was added and the solution was stirred for 1.5 h. Solvents were evaporated under reduced pressure and residual TFA was removed as an azeotrope with benzene. The residue was taken up in CH$_2$Cl$_2$ and washed with saturated NaHCO$_3$ and was then dried over Na$_2$SO$_4$, filtered, and evaporated to give the amine as a yellow-white solid, 0.62 g (98%); $^1$H NMR (CDCl$_3$) δ 8.52 (s, 1H), 8.42 (s, 2H), 3.98 (s, 3H), 3.90 (m, 1H), 2.34 (m, 1H), 0.97 (d, 6H, J=6.6); $^{13}$C-NMR δ 163.5, 160.2, 155.1, 154.4, 154.1, 142.9, 138.6, 138.4, 133.4, 129.8, 128.8, 55.8, 51.9, 33.4, 18.9, 17.8.

o. Synthesis of Compound 216 (N-Boc Divaline Hexaoxazole Ester)

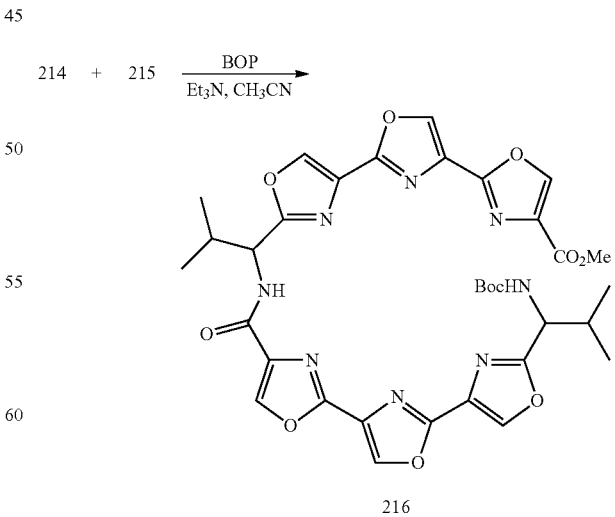

216

Dry DMF (100 mL) was added to a mixture of amine 215 (0.61 g, 1.84 mmol) and acid 214 (0.77 g, 1.84 mmol) and stirred for 5 min. BOP (0.81 g, 1.84 mmol) and triethylamine (0.6 mL, 4.3 mmol) were added and the mixture was stirred at room temperature for 12 h. The mixture was then evaporated under reduced pressure and diluted with EtOAc and brine. The phases were separated and then aqueous phase was extracted with EtOAc. The combined organic phases were then washed successively with 1N HCl, saturated NaHCO$_3$, and brine and then dried over Na$_2$SO$_4$, filtered and evaporated to give the amide as a white solid, 0.72 g (53%); mp 216-220° C.; $^1$H NMR (CDCl$_3$) δ 8.39 (s, 1H), 8.30 (s, 1H), 8.29 (s, 4H), 7.55 (d, 1H, J=9.4), 5.32 (m, 2H), 4.76 (m, 2H), 3.88 (s, 3H), 2.28 (m, 2H), 1.38 (s, 9H), 0.99 (d, 6H, J=6.6), 0.89 (d, 6H, J=6.6); $^{13}$C-NMR δ 165.1, 164.8, 163.7, 160.4, 158.9, 155.1, 143.9, 143.0, 140.8, 138.5, 135.8, 133.4, 129.8, 128.9, 79.2, 69.7, 62.6, 53.4, 51.4, 31.9, 27.4, 18.0, 17.8, 17.5, 17.1.

p. Synthesis of Compound 217 (Amino Divaline Hexaoxazole Ester)

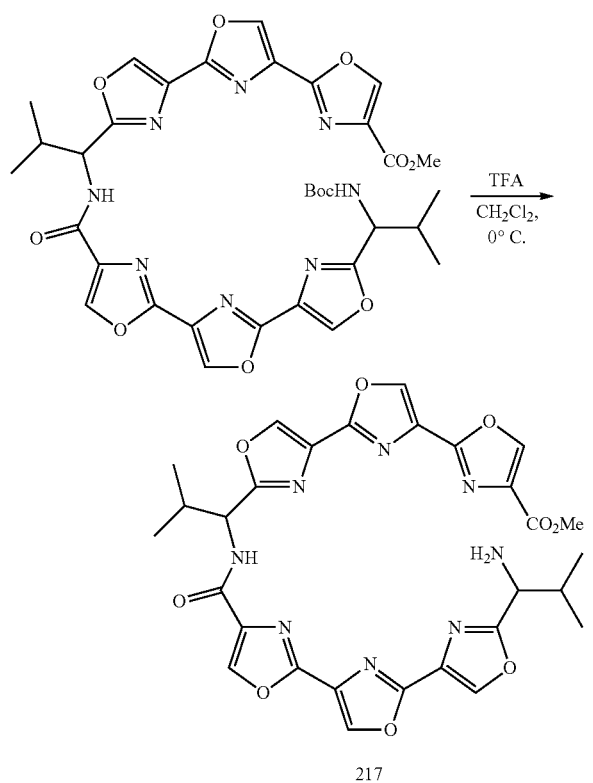

217

A solution of the N-Boc derivative (0.715 g, 0.97 mmol) in CH$_2$Cl$_2$ (10 mL) was cooled to 0° C. under protection from moisture by a drying tube. TFA (10 mL) was added and the solution was stirred for 1.5 h. Solvents were evaporated under reduced pressure and residual TFA was removed as an azeotrope with benzene. The residue was taken up in CH$_2$Cl$_2$ and washed with saturated NaHCO$_3$ and was then dried over Na$_2$SO$_4$, filtered, and evaporated to give the amine as a yellow-white solid, 0.55 g (90%); mp 267-268° C.; $^1$H NMR (CDCl$_3$) δ 8.39 (s, 2H), 8.33 (s, 1H), 8.32 (s, 1H), 8.29 (s, 2H), 7.61 (d, 1H, J=9.6), 5.29 (m, 1H), 4.59 (m, 1H), 3.89 (s, 3H), 2.21 (m, 2H), 1.03 (d, 6H, J=7.0), 0.95 (d, 6H, J=7.0); $^{13}$C-NMR δ 167.4, 163.8, 160.4, 159.0, 155.5, 154.5, 153.8, 143.6, 143.1, 140.8, 138.5, 138.3, 135.9, 133.5, 129.9, 128.9, 128.5, 54.9, 51.5, 32.5, 31.8, 18.0, 17.6, 17.1.

q. Synthesis of Compound 218 (Amino Divaline Hexaoxazole Carboxylic Acid)

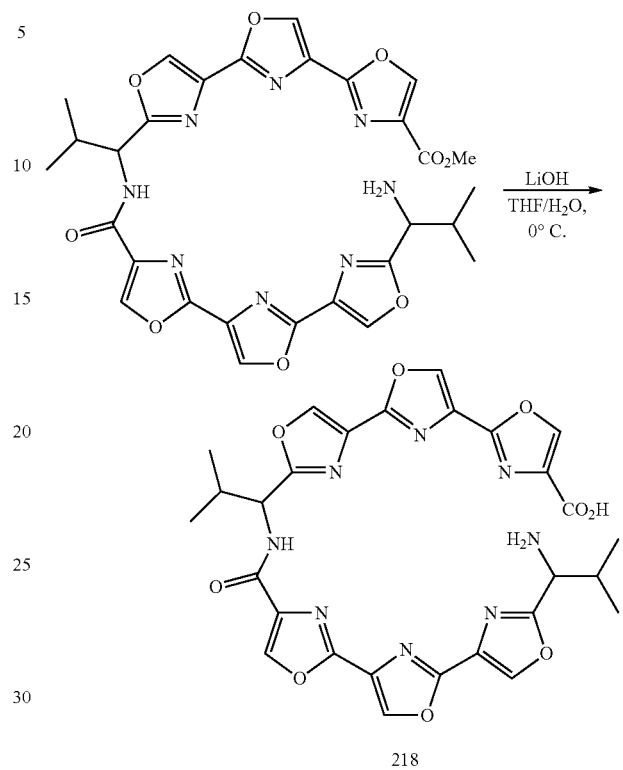

218

A solution of the ester (0.55 g, 0.87 mmol) in 3:1 THF/H$_2$O (32 mL) was stirred at 0° C. as LiOH (126 mg, 3 mmol) was added in one portion. The reaction mixture was stirred for 10 h and was then evaporated under reduced pressure to remove THF. The aqueous solution was brought to pH 3 with 1N HCl and was then extracted with EtOAc. The organic phase was washed with brine and dried over Na$_2$SO$_4$, filtered and evaporated to give the carboxylic acid as a pale yellow solid, 0.51 g (95%); mp 252-255° C. (dec.); $^1$H NMR (CD$_3$OD) δ 9.01 (s, 1H), 8.98 (s, 1H), 8.92 (s, 1H), 8.90 (s, 1H), 8.82 (s, 1H), 8.78 (s, 1H), 4.87 (m, 2H), 2.66 (m, 2H), 1.36 (d, 6H, J=7.0), 1.28 (d, 6H, J=7.0); $^{13}$C NMR δ 165.6, 162.3, 160.9, 160.8, 156.1, 144.7, 142.3, 141.7, 140.6, 140.4, 136.4, 134.3, 130.4, 130.3, 129.7, 129.3, 124.7, 53.9, 53.5, 53.0, 31.7, 29.5, 18.2, 17.7, 17.5, 16.7.

r. Synthesis of Compound 219

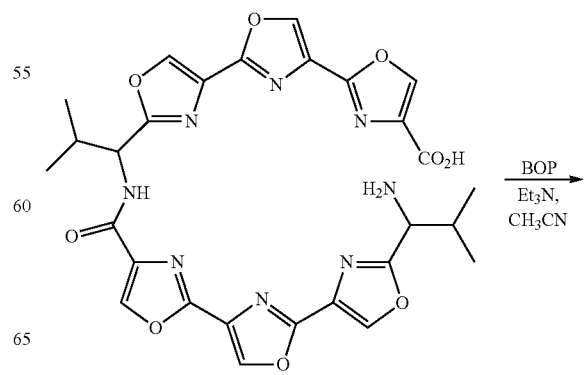

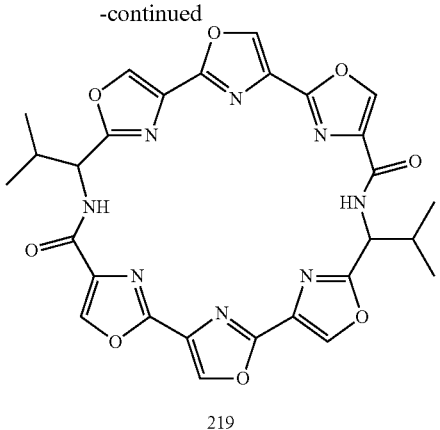

219

Amino acid 218 (0.51 g, 0.82 mmol) was dissolved in dry DMF (130 mL, 0.006 M solution) and stirred for 5 min. BOP (0.365 g, 0.82 mmol) and triethylamine (0.38 mL, 2.72 mmol) was added and the mixture was stirred at room temperature for 12 h. The solvent was evaporated under reduced pressure and the residue was diluted with EtOAc (75 mL) and brine (20 mL). The phases were separated and the aqueous was extracted with EtOAc. The combined organic layers were washed successively with 1N HCl, saturated NaHCO$_3$, and then brine. The solution was dried over Na$_2$SO$_4$, filtered, and evaporated to give compound 219 as a white solid, 0.22 g (45%); mp 246° C. (dec.); $^1$H NMR (CDCl$_3$) δ 8.51 (d, 2H, J=8), 8.20 (m, 6H), 5.30 (dd, 2H, J=8, 5), 2.40 (m, 2H), 1.04 (d, 6H, J=7), 0.98 (d, 6H, J=7); $^{13}$C NMR δ 163.7, 159.1, 155.3, 153.8, 140.0, 138.2, 137.6, 136.2, 130.2, 128.8, 52.3, 33.2, 17.7, 17.5; HRMS (FAB) Calcd for C$_{28}$H$_{24}$N$_8$O$_8$(H$^+$): 601.1795; Found: 601.1808.

Example 7

Synthesis of Compound 220

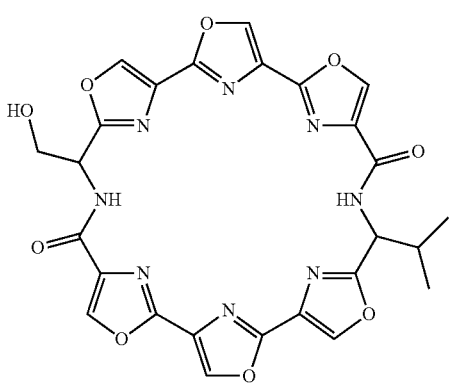

220

Using procedures similar to those described herein above, compound 220 was prepared: Off-white solid; mp. 108-110° C.; $^1$H NMR (CDCl$_3$) δ 8.47 (t, 1H, J=7.9), 8.21 (s, 3H), 8.17 (s, 3H), 5.28 (m, 2H), 4.23 (m, 1H), 3.99 (m, 1H), 2.34 (m, 1H), 0.99 (m, 27H); $^{13}$C NMR δ 163.5, 163.3, 159.0, 155.3, 153.8, 140.0, 138.3, 138.2, 137.6, 136.1, 135.9, 130.1, 128.9, 128.7, 64.1, 52.2, 51.6, 49.3, 33.0, 17.6, 17.3, 16.9, 10.9; HRMS (FAB) calcd. for C$_{35}$H$_{40}$N$_8$O$_9$Si(Li): 751.2848; Found: 751.2852.

Example 8

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

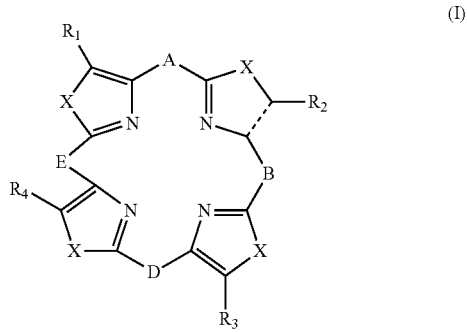

(I)

wherein:
each B and E is independently —C(=O)NH—CH($R_a$)— or —C(=O)—NH—C(=O)—;
A is a group of formula:

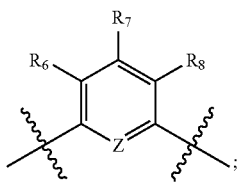

D is a group of formula:

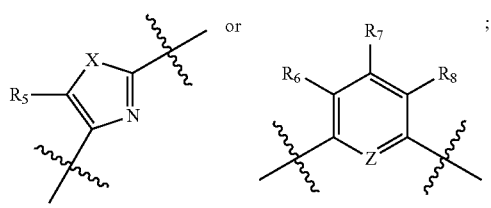

each $R_1$, $R_2$, $R_3$, $R_4$, and $R_5$ is independently H, ($C_1$-$C_6$)alkyl, or ($C_1$-$C_6$)alkoxy, wherein each ($C_1$-$C_6$)alkyl and ($C_1$-$C_6$)alkoxy is optionally substituted with OH, ($C_1$-$C_6$)alkoxy, ($C_1$-$C_6$)alkylthio, aryl, $NR_cR_d$, or —C(=O)$NR_cR_d$;

each $R_6$, $R_7$, and $R_8$ is independently H; or each $R_6$ and $R_7$ together with the atoms to which they are attached form a benzo ring and $R_8$ is H; or $R_6$ is H and $R_7$ and $R_8$ together with the atoms to which they are attached form a benzo ring;
each X is independently NH, S, or O;
each Z is independently N or CH;
the bond represented by — is a single or a double bond;
each $R_a$ is independently H, aryl, or ($C_1$-$C_6$)alkyl that is optionally substituted with OH, ($C_1$-$C_6$)alkoxy, ($C_1$-$C_6$)alkylthio, aryl, $NR_eR_f$, or —C(=O)$NR_eR_f$;
each $R_c$ and $R_d$ is independently H or ($C_1$-$C_6$)alkyl; or $R_c$ and $R_d$ together with the nitrogen to which they are attached form a pyrrolidino, piperidino, piperazino, morpholino, thiomorpholino, or azepino ring; and
each $R_e$ and $R_f$ is independently H or ($C_1$-$C_6$)alkyl; or $R_e$ and $R_f$ together with the nitrogen to which they are attached form a pyrrolidino, piperidino, piperazino, morpholino, thiomorpholino, or azepino ring;
or a salt thereof.

2. The compound of claim 1 which is a compound of formula (II):

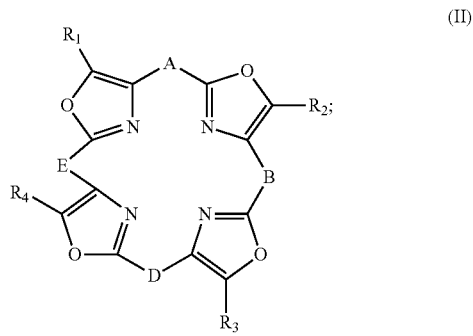

(II)

or a pharmaceutically acceptable salt thereof.

3. The compound of claim 1 wherein each X is O; and the bond represented by — is a double bond.

4. The compound of claim 1 wherein B and E are each independently —C(=O)NH—CH($R_a$)—.

5. The compound of claim 1 wherein each $R_1$, $R_2$, $R_3$, $R_4$, and $R_5$ is independently H or ($C_1$-$C_6$)alkyl that is substituted with OH, ($C_1$-$C_6$)alkoxy, ($C_1$-$C_6$)alkylthio, aryl, $NR_cR_d$, or —C(=O)$NR_cR_d$.

6. The compound of claim 1 wherein each $R_1$, $R_2$, $R_3$, $R_4$, and $R_5$ is independently H or ($C_2$-$C_6$)alkyl that is optionally substituted with OH, ($C_1$-$C_6$)alkoxy, ($C_1$-$C_6$)alkylthio, aryl, $NR_cR_d$, or —C(=O)$NR_cR_d$.

7. The compound of claim 1 wherein each Z is N.

8. The compound of claim 1 wherein each Z is CH.

9. The compound of claim 1 wherein each A and D is independently a group of the formula:

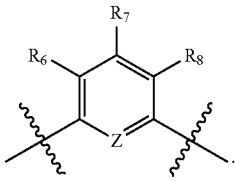

10. The compound of claim 9 wherein the bond represented by — is a double bond.

11. The compound of claim 10 wherein each X is O.

12. The compound of claim 9 wherein each Z is N.

13. The compound of claim 9 wherein each Z is CH.

14. The compound of claim 9 wherein each $R_a$ is H, methyl, isopropyl, 2-methylpropyl, benzyl, 3-(N,N-dimethylamino)propyl, or 4-(N,N-dimethylamino)butyl.

15. A pharmaceutical composition comprising a compound of formula I as described in claim 1; or a pharmaceutically acceptable salt thereof; and a pharmaceutically acceptable carrier.

16. A method to stabilize G-quadruplex DNA comprising contacting the G-quadruplex DNA with a compound of formula I as described in claim 1, or a salt thereof.

* * * * *

UNITED STATES PATENT AND TRADEMARK OFFICE
CERTIFICATE OF CORRECTION

PATENT NO. : 8,518,928 B2  
APPLICATION NO. : 13/308197  
DATED : August 27, 2013  
INVENTOR(S) : Lavoie et al.

Page 1 of 1

It is certified that error appears in the above-identified patent and that said Letters Patent is hereby corrected as shown below:

In the Claims

In column 79, lines 7 and 8,

Replace:

(N,N-dimethylamino)propyl, or 4-(N,N-dimethylamino)butyl.

With:

(*N,N*-dimethylamino)propyl, or 4-(*N,N*-dimethylamino)butyl.

Signed and Sealed this  
Twenty-fifth Day of March, 2014

Michelle K. Lee  
*Deputy Director of the United States Patent and Trademark Office*